US010525462B2

(12) United States Patent
Brown et al.

(10) Patent No.: US 10,525,462 B2
(45) Date of Patent: Jan. 7, 2020

(54) METHODS, DEVICES, AND SYSTEMS FOR SORTING PARTICLES

(71) Applicants: GEORGIA TECH RESEARCH CORPORATION, Atlanta, GA (US); Robert Clark, Charleston, SC (US)

(72) Inventors: Kenneth R. Brown, Atlanta, GA (US); Robert Clark, Charleston, SC (US); Alexa Harter, Atlanta, GA (US); Kellie McConnell, Roswell, GA (US); Brian McMahon, Stone Mountain, GA (US); Christine K. Payne, Atlanta, GA (US); Gang Shu, Atlanta, GA (US); Curtis Volin, Marietta, GA (US)

(73) Assignees: GEORGIA TECH RESEARCH CORPORATION, Atlanta, GA (US); Robert Clark, Charleston, SC (US)

( * ) Notice: Subject to any disclaimer, the term of this patent is extended or adjusted under 35 U.S.C. 154(b) by 331 days.

(21) Appl. No.: 15/493,893

(22) Filed: Apr. 21, 2017

(65) Prior Publication Data
US 2017/0304818 A1    Oct. 26, 2017

Related U.S. Application Data

(60) Provisional application No. 62/325,523, filed on Apr. 21, 2016.

(51) Int. Cl.
| | |
|---|---|
| *G01N 27/453* | (2006.01) |
| *B01L 3/00* | (2006.01) |
| *G01N 33/50* | (2006.01) |
| *C12Q 1/04* | (2006.01) |
| *G01N 27/447* | (2006.01) |

(52) U.S. Cl.
CPC ......... *B01L 3/502* (2013.01); *B01L 3/502792* (2013.01); *C12Q 1/04* (2013.01); *G01N 27/44782* (2013.01); *G01N 33/5005* (2013.01); *B01L 2200/0652* (2013.01); *B01L 2400/0415* (2013.01); *B01L 2400/0427* (2013.01)

(58) Field of Classification Search
CPC ....... B01L 2400/0427; B01L 3/502784; B01L 3/502792
See application file for complete search history.

(56) References Cited

U.S. PATENT DOCUMENTS

| | | | |
|---|---|---|---|
| 3,826,899 A | 7/1974 | Ehrlich et al. | |
| 4,499,052 A | 2/1985 | Fulwyler | |
| 4,667,830 A | 5/1987 | Nozaki et al. | |
| 5,968,739 A | 10/1999 | Anderson et al. | |
| 6,596,143 B1 * | 7/2003 | Wang .................... | B01D 57/02 204/450 |

(Continued)

FOREIGN PATENT DOCUMENTS

WO    2005108963    11/2005

OTHER PUBLICATIONS

Ateya et al., The good, the bad, and the tiny: a review of microflow cytometry. Anal Bioanal. Chem. 2008, 391,1485.

(Continued)

*Primary Examiner* — Alexander S Noguerola
(74) *Attorney, Agent, or Firm* — Meunier Carlin & Curfman LLC

(57) ABSTRACT

Disclosed herein are devices, systems, and methods for sorting a particle based on a characteristic of a particle.

20 Claims, 15 Drawing Sheets

(56) References Cited

U.S. PATENT DOCUMENTS

| | | |
|---|---|---|
| 7,154,088 B1 | 12/2006 | Blain et al. |
| 7,365,317 B2 | 4/2008 | Whitehouse et al. |
| 8,784,633 B2 * | 7/2014 | Xiang ............... B01L 3/502707 |
| | | 204/547 |

OTHER PUBLICATIONS

Fu et al. A microfabricated fluorescence-activated cell sorter. Nature Biotech. 1999, 17, 1109.

Goeders. Ph.D. Thesis, Georgia Institute of Technology, Sep. 20, 2013.

Herzenberg et al., The history and future of the fluorescence activated cell sorter and flow cytometry: a view from Stanford. Clin. Chem. 2012, 48, 1819.

Ibrahim et al. High-speed cell sorting: fundamentals and recent advances. Curr. Opin. Biotechnol. 2003, 14, 5.

Lindstrom et al. Overview of single-cell analyses: microdevices and applications. Lab on a Chip. 2010, 10, 3363.

Pearson et al. Experimental investigation of planar ion traps. Phys. Rev. A 2006, 73, 032307.

Shappert et al. Spatially uniform single-qubit gate operations with near-field microwaves and composite pulse compensation. New J. Phys. 2013, 15, 083053.

Shu et al., Heating rate and ion motion control in a Y-junction surface electrode trap. Phys. Rev. A 2014, 89, 062308.

\* cited by examiner

METHODS, DEVICES, AND SYSTEMS FOR SORTING PARTICLES

CROSS-REFERENCE TO RELATED APPLICATIONS

This application claims the benefit of U.S. Provisional Application No. 62/325,523, filed Apr. 21, 2016, which is hereby incorporated herein by reference in its entirety.

BACKGROUND

Bacterial engineering attempts to harness the internal machinery of bacteria to generate desired chemicals or to break down unwanted environmental contaminants. One method for controlling the output of bacteria is directed evolution where the production or destruction of the target chemical becomes critical for cell survival. Directed cell evolution is enhanced by the ability to rapidly separate cells based on their expressed behavior. Devices that can enable this rapid cell sorting are needed. The methods, devices, and systems discussed herein addresses these and other needs.

SUMMARY

In accordance with the purposes of the disclosed compositions and methods, as embodied and broadly described herein, the disclosed subject matter relates to devices, systems, and methods for sorting a particle based on a characteristic of a particle.

The details of one or more embodiments of the invention are set forth in the accompanying drawings and the description below. Other features, objects, and advantages of the invention will be apparent from the description and drawings, and from the claims.

Additional advantages of the invention will be set forth in part in the description which follows, and in part will be obvious from the description, or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying figures, which are incorporated in and constitute a part of this specification, illustrate several aspects of the disclosure, and together with the description, serve to explain the principles of the disclosure.

DETAILED DESCRIPTION

Figure 1:
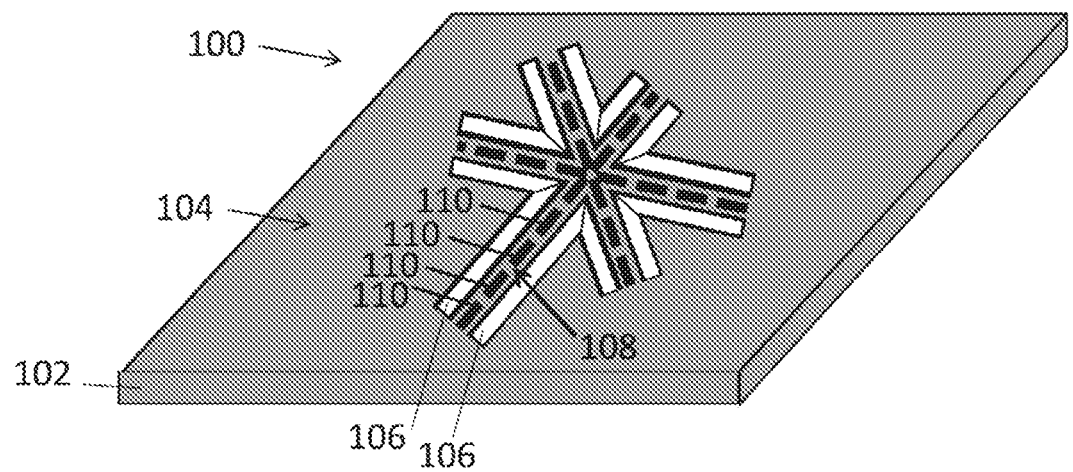
FIG. 1 is a schematic of an exemplary device as disclosed herein.

The systems and methods described herein may be understood more readily by reference to the following detailed description of specific aspects of the disclosed subject matter and the Examples included therein.

Before the present systems and methods are disclosed and described, it is to be understood that the aspects described below are not limited to specific synthetic methods or specific reagents, as such may, of course, vary. It is also to be understood that the terminology used herein is for the purpose of describing particular aspects only and is not intended to be limiting.

Also, throughout this specification, various publications are referenced. The disclosures of these publications in their entireties are hereby incorporated by reference into this application in order to more fully describe the state of the art to which the disclosed matter pertains. The references disclosed are also individually and specifically incorporated by reference herein for the material contained in them that is discussed in the sentence in which the reference is relied upon.

In this specification and in the claims that follow, reference will be made to a number of terms, which shall be defined to have the following meanings.

Throughout the description and claims of this specification the word "comprise" and other forms of the word, such as "comprising" and "comprises," means including but not limited to, and is not intended to exclude, for example, other additives, components, integers, or steps.

As used in the description and the appended claims, the singular forms "a," "an," and "the" include plural referents unless the context clearly dictates otherwise. Thus, for example, reference to "a composition" includes mixtures of two or more such compositions, reference to "an agent" includes mixtures of two or more such agents, reference to "the component" includes mixtures of two or more such components, and the like.

"Optional" or "optionally" means that the subsequently described event or circumstance can or cannot occur, and that the description includes instances where the event or circumstance occurs and instances where it does not.

Ranges can be expressed herein as from "about" one particular value, and/or to "about" another particular value. By "about" is meant within 5% of the value, e.g., within 4, 3, 2, or 1% of the value. When such a range is expressed, another aspect includes from the one particular value and/or to the other particular value. Similarly, when values are expressed as approximations, by use of the antecedent "about," it will be understood that the particular value forms another aspect. It will be further understood that the endpoints of each of the ranges are significant both in relation to the other endpoint, and independently of the other endpoint.

It is understood that throughout this specification the identifiers "first" and "second" are used solely to aid in distinguishing the various components and steps of the disclosed subject matter. The identifiers "first" and "second" are not intended to imply any particular order, amount, preference, or importance to the components or steps modified by these terms.

Devices

Described herein are devices, for example devices for particle analysis and/or particle sorting. A schematic of an example device is shown in FIG. 1. Referring now to FIG. 1, the devices 100 can comprise an insulating substrate 102 having a surface 104. The insulating substrate 102 can comprise any suitable insulating material, for example the insulating substrate can comprise FR4, epoxy, PTFE, ceramic, or any insulating laminate material for printed circuit boards.

The devices 100 further comprise a first pair of alternating current (AC) electrodes 106 disposed on the surface 104 of the insulating substrate 102, wherein each of the AC electrodes comprising the first pair of AC electrodes 106 is spaced apart on the surface 104 of the insulating substrate 102 such that the first pair of AC electrodes 106 define a first arm of a channel 108.

In some examples, the dimension of each of the AC electrodes comprising the first pair of AC electrodes 106 within the plane of the surface 104 measured parallel to the length of the first arm of the channel 108 can be 10 millimeters (mm) or more (e.g., 11 mm or more, 12 mm or more, 13 mm or more, 14 mm or more, 15 mm or more, 16 mm or more, 17 mm or more, 18 mm or more, 19 mm or more, 20 mm or more, 21 mm or more, 22 mm or more, 23 mm or more, 24 mm or more, 25 mm or more, 26 mm or more, 27 mm or more, 28 mm or more, 29 mm or more, 30 mm or more, 35 mm or more, 40 mm or more, 45 mm or more, 50 mm or more, 55 mm or more, 60 mm or more, 65 mm or more, 70 mm or more, 75 mm or more, 80 mm or more, 85 mm or more, 90 mm or more, or 95 mm or more). In some examples, the dimension of each of the AC electrodes comprising the first pair of AC electrodes 106 within the plane of the surface 104 measured parallel to the length of the first arm of the channel 108 can be 100 mm or less (e.g., 95 mm or less, 90 mm or less, 85 mm or less, 80 mm or less, 75 mm or less, 70 mm or less, 65 mm or less, 60 mm or less, 55 mm or less, 50 mm or less, 45 mm or less, 40 mm or less, 35 mm or less, 30 mm or less, 29 mm or less, 28 mm or less, 27 mm or less, 26 mm or less, 25 mm or less, 24 mm or less, 23 mm or less, 22 mm or less, 21 mm or less, 20 mm or less, 19 mm or less, 18 mm or less, 17 mm or less, 16 mm or less, or 15 mm or less). The dimension of each of the AC electrodes comprising the first pair of AC electrodes 106 within the plane of the surface 104 measured parallel to the length of the first arm of the channel 108 can range from any of the minimum values described above to any of the maximum values described above. For example, the dimension of each of the AC electrodes comprising the first pair of AC electrodes 106 within the plane of the surface 104 measured parallel to the length of the first arm of the channel 108 can be from 10 mm to 100 mm (e.g., from 10 mm to 55 mm, from 55 mm to 100 mm, from 10 mm to 40 mm, from 40 mm to 70 mm, from 70 mm to 100 mm, from 10 mm to 80 mm, from 20 mm to 60 mm, or from 20 mm to 30 mm). In some examples, the dimension of each of the AC electrodes comprising the first pair of AC electrodes 106 within the plane of the surface 104 measured parallel to the length of the first arm of the channel 108 can be substantially the same as the length of the first arm of the channel 108.

In some examples, the dimension of each of the AC electrodes comprising the first pair of AC electrodes 106 within the plane of the surface 104 measured perpendicular to the length of the first arm of the channel 108 can be 300 micrometers ($\mu$m) or more (e.g., 320 $\mu$m or more, 340 $\mu$m or more, 360 $\mu$m or more, 380 $\mu$m or more, 400 $\mu$m or more, 450 $\mu$m or more, 500 $\mu$m or more, 550 $\mu$m or more, 600 $\mu$m or more, 700 $\mu$m or more, 800 $\mu$m or more, 900 $\mu$m or more, 1000 $\mu$m or more, 1250 $\mu$m or more, 1500 $\mu$m or more, 1750 $\mu$m or more, 2000 $\mu$m or more, 2500 $\mu$m or more, 3000 $\mu$m or more, or 3500 $\mu$m or more). In some examples, the dimension of each of the AC electrodes comprising the first pair of AC electrodes 106 within the plane of the surface 104 measured perpendicular to the length of the first arm of the channel 108 can be 4000 $\mu$m or less (e.g., 3500 $\mu$m or less, 3000 $\mu$m or less, 2500 $\mu$m or less, 2000 $\mu$m or less, 1750 $\mu$m or less, 1500 $\mu$m or less, 1250 $\mu$m or less, 1000 $\mu$m or less, 900 $\mu$m or less, 800 $\mu$m or less, 700 $\mu$m or less, 600 $\mu$m or less, 550 $\mu$m or less, 500 $\mu$m or less, 450 $\mu$m or less, 400 $\mu$m or less, 380 $\mu$m or less, 360 $\mu$m or less, 340 $\mu$m or less, or 320 $\mu$m or less). The dimension of each of the AC electrodes comprising the first pair of AC electrodes 106 within the plane of the surface 104 measured perpendicular to the length of the first arm of the channel 108 can range from any of the minimum values described above to any of the maximum values described above. For example, the dimension of each of the AC electrodes comprising the first pair of AC electrodes 106 within the plane of the surface 104 measured perpendicular to the length of the first arm of the channel 108 can be from 300 µm to 4000 µm (e.g., from 300 µm to 2000 µm, from 2000 µm to 4000 µm, from 300 µm to 800 µm, from 800 µm to 1250 µm, from 1250 µm to 1750 µm, from 1750 µm to 2500 µm, from 2500 µm to 3000 µm, from 3000 µm to 3500 µm, from 3500 µm to 4000 µm, or from 380 µm to 4000 µm).

The length of the first arm of the channel 108 can, for example, be 10 millimeters (mm) or more (e.g., 11 mm or more, 12 mm or more, 13 mm or more, 14 mm or more, 15 mm or more, 16 mm or more, 17 mm or more, 18 mm or more, 19 mm or more, 20 mm or more, 21 mm or more, 22 mm or more, 23 mm or more, 24 mm or more, 25 mm or more, 26 mm or more, 27 mm or more, 28 mm or more, 29 mm or more, 30 mm or more, 35 mm or more, 40 mm or more, 45 mm or more, 50 mm or more, 55 mm or more, 60 mm or more, 65 mm or more, 70 mm or more, 75 mm or more, 80 mm or more, 85 mm or more, 90 mm or more, or 95 mm or more). In some examples, the length of the first arm of the channel 108 can be 100 mm or less (e.g., 95 mm or less, 90 mm or less, 85 mm or less, 80 mm or less, 75 mm or less, 70 mm or less, 65 mm or less, 60 mm or less, 55 mm or less, 50 mm or less, 45 mm or less, 40 mm or less, 35 mm or less, 30 mm or less, 29 mm or less, 28 mm or less, 27 mm or less, 26 mm or less, 25 mm or less, 24 mm or less, 23 mm or less, 22 mm or less, 21 mm or less, 20 mm or less, 19 mm or less, 18 mm or less, 17 mm or less, 16 mm or less, or 15 mm or less). The length of the first arm of the channel 108 can range from any of the minimum values described above to any of the maximum values described above. For example, the length of the first arm of the channel 108 can be from 10 mm to 100 mm (e.g., from 10 mm to 55 mm, from 55 mm to 100 mm, from 10 mm to 40 mm, from 40 mm to 70 mm, from 70 mm to 100 mm, from 10 mm to 80 mm, from 20 mm to 60 mm, or from 20 mm to 30 mm).

The devices further comprise a first direct current (DC) electrode 110 disposed on the surface 104 of the insulating substrate 102 and interspersed within the first arm 108 of the channel. As used herein, a "first DC electrode" and "the first DC electrode" are meant to include any number of DC electrodes disposed on the surface of the insulating substrate and interspersed within the first arm of the channel. Thus, for example, "the first DC electrode" includes one or more first DC electrodes. In some examples, the first DC electrode can comprise a first plurality of DC electrodes. In some examples, the first DC electrode comprises more than 1 DC electrodes (e.g., 2 or more, 3 or more, 4 or more, 5 or more, 6 or more, 7 or more, 8 or more, 9 or more, 10 or more, 11 or more, 12 or more, 13 or more, 14 or more, or 15 or more). In some examples, the first DC electrode comprises from 5 to 15 DC electrodes (e.g., from 6-14 DC electrodes, or from 8-14 DC electrodes). The number of DC electrodes comprising the first DC electrode can be selected, for example, in view of length of the first arm of the channel. In some examples, there can be 5-10 DC electrodes per 10 mm of the length of the arm of the channel.

The cross-section within the plane of the surface 104 of the insulating substrate 102 of the first DC electrode 110 can be of any shape (e.g., a circle, a quadrilateral, an ellipse, a triangle, a polygon, etc.). In some examples, the cross-section within the plane of the surface 104 of the insulating substrate 102 of the first DC electrode 110 is a quadrilateral (e.g., a rectangle, a parallelogram, or the like). In some examples, the cross-section within the plane of the surface 104 of the insulating substrate 102 of the first DC electrode 110 is substantially rectangular. The substantially rectangular cross-section of the first DC electrode 110 can, for example, have a length and a width. In some examples, the width of the substantially rectangular cross-section of the first DC electrode 110 can be 300 µm or more (e.g., 320 µm or more, 340 µm or more, 360 µm or more, 380 µm or more, 400 µm or more, 420 µm or more, 440 µm or more, 460 µm or more, 480 µm or more, 500 µm or more, 520 µm or more, 540 µm or more, 560 µm or more, or 580 µm or more). In some examples, the width of the substantially rectangular cross-section of the first DC electrode 110 can be 600 µm or less (e.g., 580 µm or less, 560 µm or less, 540 µm or less, 520 µm or less, 500 µm or less, 480 µm or less, 460 µm or less, 440 µm or less, 420 µm or less, 400 µm or less, 380 µm or less, 360 µm or less, 340 µm or less, or 320 µm or less). The width of the substantially rectangular cross-section of the first DC electrode 110 can range from any of the minimum values described above to any of the maximum values described above. For example, the width of the substantially rectangular cross-section of the first DC electrode 110 can be from 300 µm to 600 µm (e.g., from 300 µm to 440 µm, from 440 µm to 600 µm, from 300 µm to 400 µm, from 400 µm to 500 µm, from 500 µm to 600 µm, or from 360 µm to 400 µm).

The length of the substantially rectangular cross-section of the first DC electrode 110 can be 1-4 times the width. In some examples, the length of the substantially rectangular cross-section of the first DC electrode 110 can be 300 µm or more (e.g., 320 µm or more, 340 µm or more, 360 µm or more, 380 µm or more, 400 µm or more, 420 µm or more, 440 µm or more, 460 µm or more, 480 µm or more, 500 µm or more, 520 µm or more, 540 µm or more, 560 µm or more, 580 µm or more, 600 µm or more, 650 µm or more, 700 µm or more, 750 µm or more, 800 µm or more, 850 µm or more, 900 µm or more, 950 µm or more, 1000 µm or more, 1100 µm or more, 1200 µm or more, 1300 µm or more, 1400 µm or more, 1500 µm or more, 1750 µm or more, 2000 µm or more, or 2250 µm or more). In some examples, the length of the substantially rectangular cross-section of the first DC electrode 110 can be 2400 µm or less (e.g., 2250 µm or less, 2000 µm or less, 1750 µm or less, 1500 µm or less, 1400 µm or less, 1300 µm or less, 1200 µm or less, 1100 µm or less, 1000 µm or less, 950 µm or less, 900 µm or less, 850 µm or less, 800 µm or less, 750 µm or less, 700 µm or less, 650 µm or less, 600 µm or less, 580 µm or less, 560 µm or less, 540 µm or less, 520 µm or less, 500 µm or less, 480 µm or less, 460 µm or less, 440 µm or less, 420 µm or less, 400 µm or less, 380 µm or less, 360 µm or less, 340 µm or less, or 320 µm or less. The length of the substantially rectangular cross-section of the first DC electrode 110 can range from any of the minimum values described above to any of the maximum values described above. For example, the length of the substantially rectangular cross-section of the first DC electrode 110 can be from 300 µm to 2400 µm (e.g., from 300 µm to 1200 µm, from 1200 µm to 2400 µm, from 300 µm to 600 µm, from 600 µm to 900 µm, from 900 µm to 1200 µm, from 1200 µm to 1800 µm, from 1800 µm to 2400 µm, or from 300 µm to 1600 µm).

In some examples, each of the AC electrodes within the first pair of AC electrodes 106 is separated from the first DC electrode 110 by a first distance of 450 µm or more (e.g., 475 µm or more, 500 µm or more, 525 µm or more, 550 µm or more, 575 µm or more, 600 µm or more, 650 µm or more, 700 µm or more, 750 µm or more, 800 µm or more, 850 µm or more, 900 µm or more, 950 µm or more, 1000 µm or more, 1050 µm or more, 1100 µm or more, 1150 µm or more, 1200 µm or more, or 1250 µm or more). In some examples, each of the AC electrodes within the first pair of AC electrodes 106 is separated from the first DC electrode 110 by a first distance of 1270 µm or less (e.g., 1250 µm or less, 1200 µm or less, 1150 µm or less, 1100 µm or less, 1050 µm or less, 1000 µm or less, 950 µm or less, 900 µm or less, 850 µm or less, 800 µm or less, 750 µm or less, 700 µm or less, 650 µm or less, 600 µm or less, 575 µm or less, 550 µm or less, 525 µm or less, 500 µm or less, or 475 µm or less). The first distance can range from any of the minimum values described above to any of the maximum values described above. For example, each of the AC electrodes within the first pair of AC electrodes 106 is separated from the first DC electrode 110 by a first distance of from 450 µm to 1270 µm (e.g., from 450 µm to 850 µm, from 850 µm to 1270 µm, from 450 µm to 600 µm, from 600 µm 750 µm, from 750 µm to 900 µm, from 900 µm to 1050 µm, from 1050 µm to 1270 µm, from 475 µm to 1270 µm, or from 600 µm to 1270 µm).

In some examples, the first DC electrode 110 comprises a first plurality of DC electrodes and each DC electrode within the first plurality of DC electrodes is separated from its nearest neighboring DC electrode by a second distance of 150 µm or more (e.g., 170 µm or more, 190 nm or more, 210 µm or more, 230 µm or more, 250 µm or more, 275 µm or more, 300 µm or more, 325 µm or more, 350 µm or more, 375 µm or more, 400 µm or more, 425 µm or more, 450 nm or more, 475 µm or more, 500 µm or more, 550 µm or more, 600 µm or more, 650 µm or more, 700 µm or more, 750 µm or more, 800 µm or more, 900 µm or more, 1000 µm or more, 1100 µm or more, or 1200 µm or more). In some examples, the first DC electrode 110 comprises a first plurality of DC electrodes and each DC electrode within the first plurality of DC electrodes is separated from its nearest neighboring DC electrode by a second distance of 1270 nm or less (e.g., 1200 µm or less, 1100 µm or less, 1000 µm or less, 900 µm or less, 800 µm or less, 750 µm or less, 700 µm or less, 650 µm or less, 600 µm or less, 550 µm or less, 500 µm or less, 475 µm or less, 450 µm or less, 425 µm or less, 400 µm or less, 375 µm or less, 350 µm or less, 325 µm or less, 300 µm or less, 275 µm or less, 250 µm or less, 230 µm or less, 210 µm or less, 190 µm or less, or 170 µm or less). The second distance can range from any of the minimum values described above to any of the maximum values described above. For example, the first DC electrode 110 comprises a first plurality of DC electrodes and each DC electrode within the first plurality of DC electrodes is separated from its nearest neighboring DC electrode by a second distance of from 150 µm to 1270 µm (e.g., from 150 µm to 700 µm, from 700 µm to 1270 µm, from 150 µm to 300 µm, from 300 µm to 450 µm, from 450 µm to 600 µm, from 600 µm to 750 µm, from 750 µm to 900 µm, from 900 µm to 1050 µm, from 1050 µm to 1270 µm, from 190 µm to 1270 µm, or from 190 µm to 600 µm). In some examples, the second distance is from 190 µm to the first distance. In some examples, the first distance and the second distance are different.

In some examples, the device can further comprise a plurality of additional pairs of AC electrodes disposed on the surface of the insulating substrate, wherein each of the AC electrodes comprising the plurality of additional pairs of AC electrodes is spaced apart on the surface of the insulating substrate such that the plurality of additional pairs of AC electrodes define a plurality of additional arms of a channel, for example as shown in FIG. 1. In some examples, the plurality of additional arms of the channel can each intersect with the first arm of the channel at a junction, such that the first arm of the channel branches into a plurality of additional channels at the junction, for example as shown in FIG. 1. In certain examples, the device can further comprise a plurality of additional direct current (DC) electrode disposed on the surface of the insulating substrate and interspersed within the each of the plurality of additional arms of the channel, for example as shown in FIG. 1.

Figure 2:
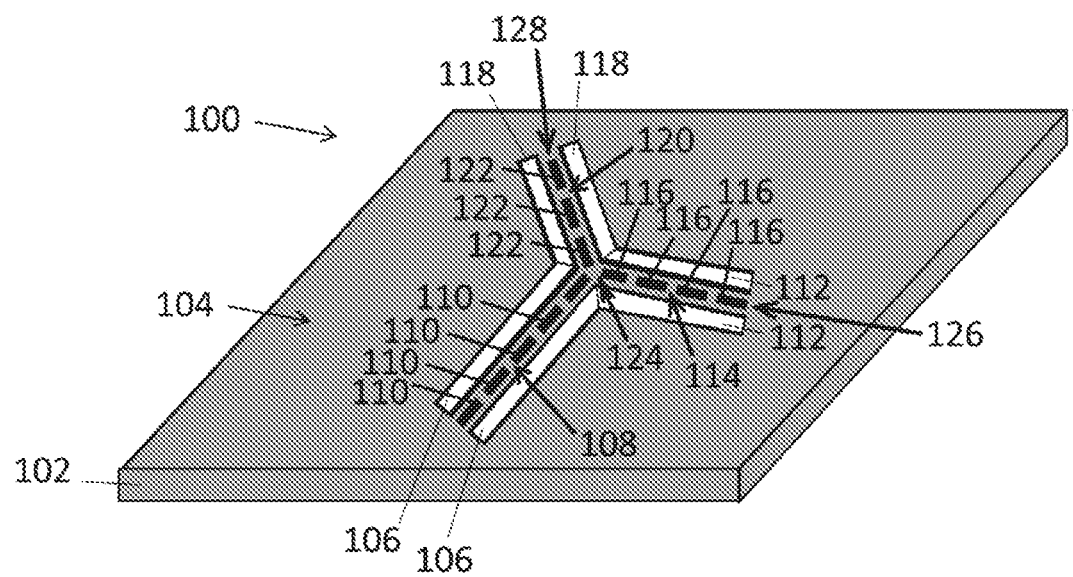
FIG. 2 is a schematic of an exemplary device as disclosed herein.

Referring now to FIG. 2, in some examples, the devices can comprise an insulating substrate 102 having a surface 104 and a first pair of alternating current (AC) electrodes 106 disposed on the surface 104 of the insulating substrate 102, wherein each of the AC electrodes comprising the first pair of AC electrodes 106 is spaced apart on the surface 104 of the insulating substrate 102 such that the first pair of AC electrodes 106 define a first arm of a channel 108. The device 100 can further comprise a first direct current (DC) electrode 110 disposed on the surface 104 of the insulating substrate 102 and interspersed within the first arm of the channel 108.

The device 100 can further comprise a second pair of alternating current (AC) electrodes 112 disposed on the surface 104 of the insulating substrate 102, wherein each of the AC electrodes comprising the second pair of AC electrodes 112 is spaced apart on the surface 104 of the insulating substrate 102 such that the second pair of AC electrodes 112 define a second arm of a channel 114.

In some examples, the dimension of each of the AC electrodes comprising the second pair of AC electrodes 112 within the plane of the surface 104 measured parallel to the length of the second arm of the channel 114 can be 10 millimeters (mm) or more (e.g., 11 mm or more, 12 mm or more, 13 mm or more, 14 mm or more, 15 mm or more, 16 mm or more, 17 mm or more, 18 mm or more, 19 mm or more, 20 mm or more, 21 mm or more, 22 mm or more, 23 mm or more, 24 mm or more, 25 mm or more, 26 mm or more, 27 mm or more, 28 mm or more, 29 mm or more, 30 mm or more, 35 mm or more, 40 mm or more, 45 mm or more, 50 mm or more, 55 mm or more, 60 mm or more, 65 mm or more, 70 mm or more, 75 mm or more, 80 mm or more, 85 mm or more, 90 mm or more, or 95 mm or more). In some examples, the dimension of each of the AC electrodes comprising the second pair of AC electrodes 112 within the plane of the surface 104 measured parallel to the length of the second arm of the channel 114 can be 100 mm or less (e.g., 95 mm or less, 90 mm or less, 85 mm or less, 80 mm or less, 75 mm or less, 70 mm or less, 65 mm or less, 60 mm or less, 55 mm or less, 50 mm or less, 45 mm or less, 40 mm or less, 35 mm or less, 30 mm or less, 29 mm or less, 28 mm or less, 27 mm or less, 26 mm or less, 25 mm or less, 24 mm or less, 23 mm or less, 22 mm or less, 21 mm or less, 20 mm or less, 19 mm or less, 18 mm or less, 17 mm or less, 16 mm or less, or 15 mm or less). The dimension of each of the AC electrodes comprising the second pair of AC electrodes 112 within the plane of the surface 104 measured parallel to the length of the second arm of the channel 114 can range from any of the minimum values described above to any of the maximum values described above. For example, the dimension of each of the AC electrodes comprising the second pair of AC electrodes 112 within the plane of the surface 104 measured parallel to the length of the second arm of the channel 114 can be from 10 mm to 100 mm (e.g., from 10 mm to 55 mm, from 55 mm to 100 mm, from 10 mm to 40 mm, from 40 mm to 70 mm, from 70 mm to 100 mm, from 10 mm to 80 mm, from 20 mm to 60 mm, or from 20 mm to 30 mm). In some examples, the dimension of each of the AC electrodes comprising the second pair of AC electrodes 112 within the plane of the surface 104 measured parallel to the length of the second arm of the channel 114 can be substantially the same as the length of the second arm of the channel 114.

In some examples, the dimension of each of the AC electrodes comprising the second pair of AC electrodes 112 within the plane of the surface 104 measured perpendicular to the length of the second arm of the channel 114 can be 300 micrometers (μm) or more (e.g., 320 μm or more, 340 μm or more, 360 μm or more, 380 μm or more, 400 μm or more, 450 μm or more, 500 μm or more, 550 μm or more, 600 μm or more, 700 μm or more, 800 μm or more, 900 μm or more, 1000 μm or more, 1250 μm or more, 1500 μm or more, 1750 μm or more, 2000 μm or more, 2500 μm or more, 3000 μm or more, or 3500 μm or more). In some examples, the dimension of each of the AC electrodes comprising the second pair of AC electrodes 112 within the plane of the surface 104 measured perpendicular to the length of the second arm of the channel 114 can be 4000 μm or less (e.g., 3500 μm or less, 3000 μm or less, 2500 μm or less, 2000 μm or less, 1750 μm or less, 1500 μm or less, 1250 μm or less, 1000 μm or less, 900 μm or less, 800 μm or less, 700 μm or less, 600 μm or less, 550 μm or less, 500 μm or less, 450 μm or less, 400 μm or less, 380 μm or less, 360 μm or less, 340 μm or less, or 320 μm or less). The dimension of each of the AC electrodes comprising the second pair of AC electrodes 112 within the plane of the surface 104 measured perpendicular to the length of the second arm of the channel 114 can range from any of the minimum values described above to any of the maximum values described above. For example, the dimension of each of the AC electrodes comprising the second pair of AC electrodes 112 within the plane of the surface 104 measured perpendicular to the length of the second arm of the channel 114 can be from 300 μm to 4000 μm (e.g., from 300 μm to 2000 μm, from 2000 μm to 4000 μm, from 300 μm to 800 μm, from 800 μm to 1250 μm, from 1250 μm to 1750 μm, from 1750 μm to 2500 μm, from 2500 μm to 3000 μm, from 3000 μm to 3500 μm, from 3500 μm to 4000 μm, or from 380 μm to 4000 μm).

The length of the second arm of the channel 114 can, for example, be 10 millimeters (mm) or more (e.g., 11 mm or more, 12 mm or more, 13 mm or more, 14 mm or more, 15 mm or more, 16 mm or more, 17 mm or more, 18 mm or more, 19 mm or more, 20 mm or more, 21 mm or more, 22 mm or more, 23 mm or more, 24 mm or more, 25 mm or more, 26 mm or more, 27 mm or more, 28 mm or more, 29 mm or more, 30 mm or more, 35 mm or more, 40 mm or more, 45 mm or more, 50 mm or more, 55 mm or more, 60 mm or more, 65 mm or more, 70 mm or more, 75 mm or more, 80 mm or more, 85 mm or more, 90 mm or more, or 95 mm or more). In some examples, the length of the second arm of the channel 114 can be 100 mm or less (e.g., 95 mm or less, 90 mm or less, 85 mm or less, 80 mm or less, 75 mm or less, 70 mm or less, 65 mm or less, 60 mm or less, 55 mm or less, 50 mm or less, 45 mm or less, 40 mm or less, 35 mm or less, 30 mm or less, 29 mm or less, 28 mm or less, 27 mm or less, 26 mm or less, 25 mm or less, 24 mm or less, 23 mm or less, 22 mm or less, 21 mm or less, 20 mm or less, 19 mm or less, 18 mm or less, 17 mm or less, 16 mm or less, or 15 mm or less). The length of the second arm of the channel 114 can range from any of the minimum values described above to any of the maximum values described above. For example, the length of the second arm of the channel 114 can be from 10 mm to 100 mm (e.g., from 10 mm to 55 mm, from 55 mm to 100 mm, from 10 mm to 40 mm, from 40 mm to 70 mm, from 70 mm to 100 mm, from 10 mm to 80 mm, from 20 mm to 60 mm, or from 20 mm to 30 mm). In some examples, the length of the second arm of the channel 114 is the same as the length of the first arm of the channel 108.

The device 100 can further comprise a second direct current (DC) electrode 116 disposed on the surface 104 of the insulating substrate 102 and interspersed within the second arm of the channel 114. As used herein, a "second DC electrode" and "the second DC electrode" are meant to include any number of DC electrodes disposed on the surface 104 of the insulating substrate and interspersed within the second arm of the channel. Thus, for example, "the second DC electrode" includes one or more second DC electrodes. In some examples, the second DC electrode 116 can comprise a second plurality of DC electrodes. In some examples, the second DC electrode 116 comprises more than 1 DC electrodes (e.g., 2 or more, 3 or more, 4 or more, 5 or more, 6 or more, 7 or more, 8 or more, 9 or more, 10 or more, 11 or more, 12 or more, 13 or more, 14 or more, or 15 or more). In some examples, the second DC electrode comprises from 5 to 15 DC electrodes (e.g., from 6-14 DC electrodes, or from 8-14 DC electrodes). The number of DC electrodes comprising the second DC electrode can be selected, for example, in view of length of the second arm of the channel. In some examples, there can be 5-10 DC electrodes per 10 mm of the length of the arm of the channel.

The cross-section within the plane of the surface 104 of the insulating substrate 102 of the second DC electrode 116 can be of any shape (e.g., a circle, a quadrilateral, an ellipse, a triangle, a polygon, etc.). In some examples, the cross-section within the plane of the surface 104 of the insulating substrate 102 of the second DC electrode 116 is a quadrilateral (e.g., a rectangle, a parallelogram, or the like). In some examples, the cross-section within the plane of the surface 104 of the insulating substrate 102 of the second DC electrode 116 is substantially rectangular. The substantially rectangular cross-section of the second DC electrode 116 can, for example, have a length and a width. In some examples, the width of the substantially rectangular cross-section of the second DC electrode 116 can be 300 μm or more (e.g., 320 μm or more, 340 μm or more, 360 μm or more, 380 μm or more, 400 μm or more, 420 μm or more, 440 μm or more, 460 μm or more, 480 μm or more, 500 μm or more, 520 μm or more, 540 μm or more, 560 μm or more, or 580 μm or more). In some examples, the width of the substantially rectangular cross-section of the second DC electrode 116 can be 600 μm or less (e.g., 580 μm or less, 560 μm or less, 540 μm or less, 520 μm or less, 500 μm or less, 480 μm or less, 460 μm or less, 440 μm or less, 420 μm or less, 400 μm or less, 380 μm or less, 360 μm or less, 340 μm or less, or 320 μm or less). The width of the substantially rectangular cross-section of the second DC electrode 116 can range from any of the minimum values described above to any of the maximum values described above. For example, the width of the substantially rectangular cross-section of the second DC electrode 116 can be from 300 μm to 600 μm (e.g., from 300 μm to 440 μm, from 440 μm to 600 μm, from 300 μm to 400 μm, from 400 μm to 500 μm, from 500 μm to 600 μm, or from 360 μm to 400 μm).

The length of the substantially rectangular cross-section of the second DC electrode 116 can be 1-4 times the width. In some examples, the length of the substantially rectangular cross-section of the second DC electrode 116 can be 300 μm or more (e.g., 320 μm or more, 340 μm or more, 360 μm or more, 380 μm or more, 400 μm or more, 420 μm or more, 440 μm or more, 460 μm or more, 480 μm or more, 500 μm or more, 520 μm or more, 540 μm or more, 560 μm or more, 580 μm or more, 600 μm or more, 650 μm or more, 700 μm or more, 750 µm or more, 800 µm or more, 850 µm or more, 900 µm or more, 950 µm or more, 1000 µm or more, 1100 µm or more, 1200 µm or more, 1300 µm or more, 1400 µm or more, 1500 µm or more, 1750 µm or more, 2000 µm or more, or 2250 µm or more). In some examples, the length of the substantially rectangular cross-section of the second DC electrode 116 can be 2400 µm or less (e.g., 2250 µm or less, 2000 µm or less, 1750 µm or less, 1500 µm or less, 1400 µm or less, 1300 µm or less, 1200 µm or less, 1100 µm or less, 1000 µm or less, 950 µm or less, 900 µm or less, 850 µm or less, 800 µm or less, 750 µm or less, 700 µm or less, 650 µm or less, 600 µm or less, 580 µm or less, 560 µm or less, 540 µm or less, 520 µm or less, 500 µm or less, 480 µm or less, 460 µm or less, 440 µm or less, 420 µm or less, 400 µm or less, 380 µm or less, 360 µm or less, 340 µm or less, or 320 µm or less. The length of the substantially rectangular cross-section of the second DC electrode 116 can range from any of the minimum values described above to any of the maximum values described above. For example, the length of the substantially rectangular cross-section of the second DC electrode 116 can be from 300 µm to 2400 µm (e.g., from 300 µm to 1200 µm, from 1200 µm to 2400 µm, from 300 µm to 600 µm, from 600 µm to 900 µm, from 900 µm to 1200 µm, from 1200 µm to 1800 µm, from 1800 µm to 2400 µm, or from 300 µm to 1600 µm). In some examples, each of the AC electrodes within the second pair of AC electrodes 112 is separated from the second DC electrode 116 by a third distance of 450 µm or more (e.g., 475 µm or more, 500 µm or more, 525 µm or more, 550 µm or more, 575 µm or more, 600 µm or more, 650 µm or more, 700 µm or more, 750 µm or more, 800 µm or more, 850 µm or more, 900 µm or more, 950 µm or more, 1000 µm or more, 1050 µm or more, 1100 µm or more, 1150 µm or more, 1200 µm or more, or 1250 µm or more). In some examples, each of the AC electrodes within the second pair of AC electrodes 112 is separated from the second DC electrode 116 by a third distance of 1270 µm or less (e.g., 1250 µm or less, 1200 µm or less, 1150 µm or less, 1100 µm or less, 1050 µm or less, 1000 µm or less, 950 µm or less, 900 µm or less, 850 µm or less, 800 µm or less, 750 µm or less, 700 µm or less, 650 µm or less, 600 µm or less, 575 µm or less, 550 µm or less, 525 µm or less, 500 µm or less, or 475 µm or less). The third distance can range from any of the minimum values described above to any of the maximum values described above. For example, each of the AC electrodes within the second pair of AC electrodes 112 is separated from the second DC electrode 116 by a third distance of from 450 µm to 1270 µm (e.g., from 450 µm to 850 µm, from 850 µm to 1270 µm, from 450 µm to 600 µm, from 600 µm 750 µm, from 750 µm to 900 µm, from 900 µm to 1050 µm, from 1050 µm to 1270 µm, from 475 µm to 1270 µm, or from 600 µm to 1270 µm). In some examples, the first distance and the third distance are the same.

In some examples, the second DC electrode 116 comprises a second plurality of DC electrodes and each DC electrode within the second plurality of DC electrodes is separated from its nearest neighboring DC electrode by a fourth distance of 150 µm or more (e.g., 170 µm or more, 190 µm or more, 210 µm or more, 230 µm or more, 250 µm or more, 275 µm or more, 300 µm or more, 325 µm or more, 350 µm or more, 375 µm or more, 400 µm or more, 425 µm or more, 450 µm or more, 475 µm or more, 500 µm or more, 550 µm or more, 600 µm or more, 650 µm or more, 700 µm or more, 750 µm or more, 800 µm or more, 900 µm or more, 1000 µm or more, 1100 µm or more, or 1200 µm or more). In some examples, the second DC electrode 116 comprises a second plurality of DC electrodes and each DC electrode within the second plurality of DC electrodes is separated from its nearest neighboring DC electrode by a fourth distance of 1270 µm or less (e.g., 1200 µm or less, 1100 µm or less, 1000 µm or less, 900 µm or less, 800 µm or less, 750 µm or less, 700 µm or less, 650 µm or less, 600 µm or less, 550 µm or less, 500 µm or less, 475 µm or less, 450 µm or less, 425 µm or less, 400 µm or less, 375 µm or less, 350 µm or less, 325 µm or less, 300 µm or less, 275 µm or less, 250 µm or less, 230 µm or less, 210 µm or less, 190 µm or less, or 170 µm or less). The fourth distance can range from any of the minimum values described above to any of the maximum values described above. For example, the second DC electrode 116 comprises a second plurality of DC electrodes and each DC electrode within the second plurality of DC electrodes is separated from its nearest neighboring DC electrode by a fourth distance of from 150 µm to 1270 µm (e.g., from 150 µm to 700 µm, from 700 µm to 1270 µm, from 150 µm to 300 µm, from 300 µm to 450 µm, from 450 µm to 600 µm, from 600 µm to 750 µm, from 750 µm to 900 µm, from 900 µm to 1050 µm, from 1050 µm to 1270 µm, from 190 µm to 1270 µm, or from 190 µm to 600 µm). In some examples, the fourth distance is from 190 µm to the third distance. In some examples, the third distance and the fourth distance are different. In some examples, the second distance and the fourth distance are the same.

The device can further comprise a third pair of alternating current (AC) electrodes 118 disposed on the surface 104 of the insulating substrate 102, wherein each of the AC electrodes comprising the third pair of AC electrodes 118 is spaced apart on the surface 104 of the insulating substrate 102 such that the third pair of AC electrodes 118 define a third arm of a channel 120.

In some examples, the dimension of each of the AC electrodes comprising the third pair of AC electrodes 118 within the plane of the surface 104 measured parallel to the length of the third arm of the channel 120 can be 10 millimeters (mm) or more (e.g., 11 mm or more, 12 mm or more, 13 mm or more, 14 mm or more, 15 mm or more, 16 mm or more, 17 mm or more, 18 mm or more, 19 mm or more, 20 mm or more, 21 mm or more, 22 mm or more, 23 mm or more, 24 mm or more, 25 mm or more, 26 mm or more, 27 mm or more, 28 mm or more, 29 mm or more, 30 mm or more, 35 mm or more, 40 mm or more, 45 mm or more, 50 mm or more, 55 mm or more, 60 mm or more, 65 mm or more, 70 mm or more, 75 mm or more, 80 mm or more, 85 mm or more, 90 mm or more, or 95 mm or more). In some examples, the dimension of each of the AC electrodes comprising the third pair of AC electrodes 118 within the plane of the surface 104 measured parallel to the length of the third arm of the channel 120 can be 100 mm or less (e.g., 95 mm or less, 90 mm or less, 85 mm or less, 80 mm or less, 75 mm or less, 70 mm or less, 65 mm or less, 60 mm or less, 55 mm or less, 50 mm or less, 45 mm or less, 40 mm or less, 35 mm or less, 30 mm or less, 29 mm or less, 28 mm or less, 27 mm or less, 26 mm or less, 25 mm or less, 24 mm or less, 23 mm or less, 22 mm or less, 21 mm or less, 20 mm or less, 19 mm or less, 18 mm or less, 17 mm or less, 16 mm or less, or 15 mm or less). The dimension of each of the AC electrodes comprising the third pair of AC electrodes 118 within the plane of the surface 104 measured parallel to the length of the third arm of the channel 120 can range from any of the minimum values described above to any of the maximum values described above. For example, the dimension of each of the AC electrodes comprising the third pair of AC electrodes 118 within the plane of the surface 104 measured parallel to the length of the third arm of the channel 120 can be from 10 mm to 100 mm (e.g., from 10 mm to 55 mm, from 55 mm to 100 mm, from 10 mm to 40 mm, from 40 mm to 70 mm, from 70 mm to 100 mm, from 10 mm to 80 mm, from 20 mm to 60 mm, or from 20 mm to 30 mm). In some examples, the dimension of each of the AC electrodes comprising the third pair of AC electrodes 118 within the plane of the surface 104 measured parallel to the length of the third arm of the channel 120 can be substantially the same as the length of the third arm of the channel 120.

In some examples, the dimension of each of the AC electrodes comprising the third pair of AC electrodes 118 within the plane of the surface 104 measured perpendicular to the length of the third arm of the channel 120 can be 300 micrometers (pin) or more (e.g., 320 μm or more, 340 μm or more, 360 μm or more, 380 μm or more, 400 μm or more, 450 μm or more, 500 μm or more, 550 μm or more, 600 μm or more, 700 μm or more, 800 μm or more, 900 μm or more, 1000 μm or more, 1250 μm or more, 1500 μm or more, 1750 μm or more, 2000 μm or more, 2500 μm or more, 3000 μm or more, or 3500 μm or more). In some examples, the dimension of each of the AC electrodes comprising the third pair of AC electrodes 118 within the plane of the surface 104 measured perpendicular to the length of the third arm of the channel 120 can be 4000 μm or less (e.g., 3500 μm or less, 3000 μm or less, 2500 μm or less, 2000 μm or less, 1750 μm or less, 1500 μm or less, 1250 μm or less, 1000 μm or less, 900 μm or less, 800 μm or less, 700 μm or less, 600 μm or less, 550 μm or less, 500 μm or less, 450 μm or less, 400 μm or less, 380 μm or less, 360 μm or less, 340 μm or less, or 320 μm or less). The dimension of each of the AC electrodes comprising the third pair of AC electrodes 118 within the plane of the surface 104 measured perpendicular to the length of the third arm of the channel 120 can range from any of the minimum values described above to any of the maximum values described above. For example, the dimension of each of the AC electrodes comprising the third pair of AC electrodes 118 within the plane of the surface 104 measured perpendicular to the length of the third arm of the channel 120 can be from 300 μm to 4000 μm (e.g., from 300 μm to 2000 μm, from 2000 μm to 4000 μm, from 300 μm to 800 μm, from 800 μm to 1250 μm, from 1250 μm to 1750 μm, from 1750 μm to 2500 μm, from 2500 μm to 3000 μm, from 3000 μm to 3500 μm, from 3500 μm to 4000 μm, or from 380 μm to 4000 μm). The length of the third arm of the channel 120 can, for example, be 10 millimeters (mm) or more (e.g., 11 mm or more, 12 mm or more, 13 mm or more, 14 mm or more, 15 mm or more, 16 mm or more, 17 mm or more, 18 mm or more, 19 mm or more, 20 mm or more, 21 mm or more, 22 mm or more, 23 mm or more, 24 mm or more, 25 mm or more, 26 mm or more, 27 mm or more, 28 mm or more, 29 mm or more, 30 mm or more, 35 mm or more, 40 mm or more, 45 mm or more, 50 mm or more, 55 mm or more, 60 mm or more, 65 mm or more, 70 mm or more, 75 mm or more, 80 mm or more, 85 mm or more, 90 mm or more, or 95 mm or more). In some examples, the length of the third arm of the channel 120 can be 100 mm or less (e.g., 95 mm or less, 90 mm or less, 85 mm or less, 80 mm or less, 75 mm or less, 70 mm or less, 65 mm or less, 60 mm or less, 55 mm or less, 50 mm or less, 45 mm or less, 40 mm or less, 35 mm or less, 30 mm or less, 29 mm or less, 28 mm or less, 27 mm or less, 26 mm or less, 25 mm or less, 24 mm or less, 23 mm or less, 22 mm or less, 21 mm or less, 20 mm or less, 19 mm or less, 18 mm or less, 17 mm or less, 16 mm or less, or 15 mm or less). The length of the third arm of the channel 120 can range from any of the minimum values described above to any of the maximum values described above. For example, the length of the third arm of the channel 120 can be from 10 mm to 100 mm (e.g., from 10 mm to 55 mm, from 55 mm to 100 mm, from 10 mm to 40 mm, from 40 mm to 70 mm, from 70 mm to 100 mm, from 10 mm to 80 mm, from 20 mm to 60 mm, or from 20 mm to 30 mm). In some examples, the length of the third arm of the channel 120 is the same as the length of the first arm of the channel 108 and/or the second arm of the channel 114.

The device 100 can further comprise a third direct current (DC) electrode 122 disposed on the surface 104 of the insulating substrate 102 and interspersed within the third arm of the channel 120. As used herein, a "third DC electrode" and "the third DC electrode" are meant to include any number of DC electrodes disposed on the surface of the insulating substrate and interspersed within the third arm of the channel. Thus, for example, "the third DC electrode" includes one or more third DC electrodes. In some examples, the third DC electrode 122 can comprise a third plurality of DC electrodes. In some examples, the third DC electrode 122 comprises more than 1 DC electrodes (e.g., 2 or more, 3 or more, 4 or more, 5 or more, 6 or more, 7 or more, 8 or more, 9 or more, 10 or more, 11 or more, 12 or more, 13 or more, 14 or more, or 15 or more). In some examples, the third DC electrode comprises from 5 to 15 DC electrodes (e.g., from 6-14 DC electrodes, or from 8-14 DC electrodes). The number of DC electrodes comprising the third DC electrode can be selected, for example, in view of length of the third arm of the channel. In some examples, there can be 5-10 DC electrodes per 10 mm of the length of the arm of the channel.

The cross-section within the plane of the surface 104 of the insulating substrate 102 of the third DC electrode 122 can be of any shape (e.g., a circle, a quadrilateral, an ellipse, a triangle, a polygon, etc.). In some examples, the cross-section within the plane of the surface 104 of the insulating substrate 102 of the third DC electrode 122 is a quadrilateral (e.g., a rectangle, a parallelogram, or the like). In some examples, the cross-section within the plane of the surface 104 of the insulating substrate 102 of the third DC electrode 122 is substantially rectangular. The substantially rectangular cross-section of the third DC electrode 122 can, for example, have a length and a width. In some examples, the width of the substantially rectangular cross-section of the third DC electrode 122 can be 300 μm or more (e.g., 320 μm or more, 340 μm or more, 360 μm or more, 380 μm or more, 400 μm or more, 420 μm or more, 440 μm or more, 460 μm or more, 480 μm or more, 500 μm or more, 520 μm or more, 540 μm or more, 560 μm or more, or 580 μm or more). In some examples, the width of the substantially rectangular cross-section of the third DC electrode 122 can be 600 μm or less (e.g., 580 μm or less, 560 μm or less, 540 μm or less, 520 μm or less, 500 μm or less, 480 μm or less, 460 μm or less, 440 μm or less, 420 μm or less, 400 μm or less, 380 μm or less, 360 μm or less, 340 μm or less, or 320 μm or less). The width of the substantially rectangular cross-section of the third DC electrode 122 can range from any of the minimum values described above to any of the maximum values described above. For example, the width of the substantially rectangular cross-section of the third DC electrode 122 can be from 300 μm to 600 μm (e.g., from 300 μm to 440 μm, from 440 μm to 600 μm, from 300 μm to 400 μm, from 400 μm to 500 μm, from 500 μm to 600 μm, or from 360 μm to 400 μm).

The length of the substantially rectangular cross-section of the third DC electrode 122 can be 1-4 times the width. In some examples, the length of the substantially rectangular cross-section of the third DC electrode 122 can be 300 μm or more (e.g., 320 µm or more, 340 µm or more, 360 µm or more, 380 µm or more, 400 µm or more, 420 µm or more, 440 µm or more, 460 µm or more, 480 µm or more, 500 µm or more, 520 µm or more, 540 µm or more, 560 µm or more, 580 µm or more, 600 µm or more, 650 µm or more, 700 µm or more, 750 µm or more, 800 µm or more, 850 µm or more, 900 µm or more, 950 µm or more, 1000 µm or more, 1100 µm or more, 1200 µm or more, 1300 µm or more, 1400 µm or more, 1500 µm or more, 1750 µm or more, 2000 µm or more, or 2250 µm or more). In some examples, the length of the substantially rectangular cross-section of the third DC electrode 122 can be 2400 µm or less (e.g., 2250 µm or less, 2000 µm or less, 1750 µm or less, 1500 µm or less, 1400 µm or less, 1300 µm or less, 1200 µm or less, 1100 µm or less, 1000 µm or less, 950 µm or less, 900 µm or less, 850 µm or less, 800 µm or less, 750 µm or less, 700 µm or less, 650 µm or less, 600 µm or less, 580 µm or less, 560 µm or less, 540 µm or less, 520 µm or less, 500 µm or less, 480 µm or less, 460 µm or less, 440 µm or less, 420 µm or less, 400 µm or less, 380 µm or less, 360 µm or less, 340 µm or less, or 320 µm or less. The length of the substantially rectangular cross-section of the third DC electrode 122 can range from any of the minimum values described above to any of the maximum values described above. For example, the length of the substantially rectangular cross-section of the third DC electrode 122 can be from 300 µm to 2400 µm (e.g., from 300 µm to 1200 µm, from 1200 µm to 2400 µm, from 300 µm to 600 µm, from 600 µm to 900 µm, from 900 µm to 1200 µm, from 1200 µm to 1800 µm, from 1800 µm to 2400 µm, or from 300 µm to 1600 µm).

In some examples, each of the AC electrodes within the third pair of AC electrodes 118 is separated from the third DC electrode 122 by a fifth distance of 450 µm or more (e.g., 475 µm or more, 500 µm or more, 525 µm or more, 550 µm or more, 575 µm or more, 600 µm or more, 650 µm or more, 700 µm or more, 750 µm or more, 800 µm or more, 850 µm or more, 900 µm or more, 950 µm or more, 1000 µm or more, 1050 µm or more, 1100 µm or more, 1150 µm or more, 1200 µm or more, or 1250 µm or more), In some examples, each of the AC electrodes within the third pair of AC electrodes 118 is separated from the third DC electrode 122 by a fifth distance of 1270 µm or less (e.g., 1250 µm or less, 1200 µm or less, 1150 µm or less, 1100 µm or less, 1050 µm or less, 1000 µm or less, 950 µm or less, 900 µm or less, 850 µm or less, 800 µm or less, 750 µm or less, 700 µm or less, 650 µm or less, 600 µm or less, 575 µm or less, 550 µm or less, 525 µm or less, 500 µm or less, or 475 µm or less). The fifth distance can range from any of the minimum values described above to any of the maximum values described above. For example, each of the AC electrodes within the third pair of AC electrodes 118 is separated from the third DC electrode 122 by a fifth distance of from 450 µm to 1270 µm (e.g., from 450 µm to 850 µm, from 850 µm to 1270 µm, from 450 µm to 600 µm, from 600 µm 750 µm, from 750 µm to 900 µm, from 900 µm to 1050 µm, from 1050 µm to 1270 µm, from 475 µm to 1270 µm, or from 600 µm to 1270 µm). In some examples, the fifth distance is the same as the first distance and/or the third distance.

In some examples, the third DC electrode 122 comprises a third plurality of DC electrodes and each DC electrode within the third plurality of DC electrodes is separated from its nearest neighboring DC electrode by a sixth distance of 150 µm or more (e.g., 170 µm or more, 190 µm or more, 210 µm or more, 230 µm or more, 250 µm or more, 275 µm or more, 300 µm or more, 325 µm or more, 350 µm or more, 375 µm or more, 400 µm or more, 425 µm or more, 450 µm or more, 475 µm or more, 500 µm or more, 550 µm or more, 600 µm or more, 650 µm or more, 700 µm or more, 750 µm or more, 800 µm or more, 900 µm or more, 1000 µm or more, 1100 µm or more, or 1200 µm or more), In some examples, the third DC electrode 122 comprises a third plurality of DC electrodes and each DC electrode within the third plurality of DC electrodes is separated from its nearest neighboring DC electrode by a sixth distance of 1270 µm or less (e.g., 1200 µm or less, 1100 µm or less, 1000 µm or less, 900 µm or less, 800 µm or less, 750 µm or less, 700 µm or less, 650 µm or less, 600 µm or less, 550 µm or less, 500 µm or less, 475 µm or less, 450 µm or less, 425 µm or less, 400 µm or less, 375 µm or less, 350 µm or less, 325 µm or less, 300 µm or less, 275 µm or less, 250 µm or less, 230 µm or less, 210 µm or less, 190 µm or less, or 170 µm or less). The sixth distance can range from any of the minimum values described above to any of the maximum values described above. For example, the third DC electrode 122 comprises a third plurality of DC electrodes and each DC electrode within the third plurality of DC electrodes is separated from its nearest neighboring DC electrode by a sixth distance of from 150 µm to 1270 µm (e.g., from 150 µm to 700 µm, from 700 µm to 1270 µm, from 150 µm to 300 µm, from 300 µm to 450 µm, from 450 µm to 600 µm, from 600 µm to 750 nm, from 750 µm to 900 µm, from 900 µm to 1050 µm, from 1050 µm to 1270 µm, from 190 µm to 1270 µm, or from 190 µm to 600 µm). In some examples, the sixth distance is from 190 µm to the fifth distance. In some examples, the fifth distance and the sixth distance are different. In some examples, the sixth distance is the same as the second distance and/or the fourth distance.

The device 100 can further comprise a junction 124, wherein the first 108, second 114, and third 120 arms of the channel intersect at a junction 124. For example, the first arm of the channel 108 can split into the second 114 and third 120 arms of the channel at the junction 124. In some examples, the second arm of the channel 114 can further comprise a collection region 126, such that the second arm of the channel 114 extends from the junction 124 to the collection region 126.

In some examples, the third arm of the channel 120 further comprises a collection region 128, such that third arm of the channel 120 extends from the junction 124 to the collection region 128.

In some examples, the device can further comprise a plurality of additional pairs of AC electrodes disposed on the surface of the insulating substrate, wherein each of the AC electrodes comprising the plurality of additional pairs of AC electrodes is spaced apart on the surface of the insulating substrate such that the plurality of additional pairs of AC electrodes define a plurality of additional arms of a channel, wherein the plurality of additional arms of the channel can each intersect with the second arm of the channel at a second junction, such that the second arm of the channel branches into a plurality of additional channels at the second junction. In certain examples, the device can further comprise a plurality of additional direct current (DC) electrode disposed on the surface of the insulating substrate and interspersed within the each of the plurality of additional arms of the channel.

In some examples, the device can further comprise a plurality of additional pairs of AC electrodes disposed on the surface of the insulating substrate, wherein each of the AC electrodes comprising the plurality of additional pairs of AC electrodes is spaced apart on the surface of the insulating substrate such that the plurality of additional pairs of AC electrodes define a plurality of additional arms of a channel, wherein the plurality of additional arms of the channel can each intersect with the third arm of the channel at a third junction, such that the third arm of the channel branches into a plurality of additional channels at the third junction. In certain examples, the device can further comprise a plurality of additional direct current (DC) electrode disposed on the surface of the insulating substrate and interspersed within the each of the plurality of additional arms of the channel.

Figure 3:
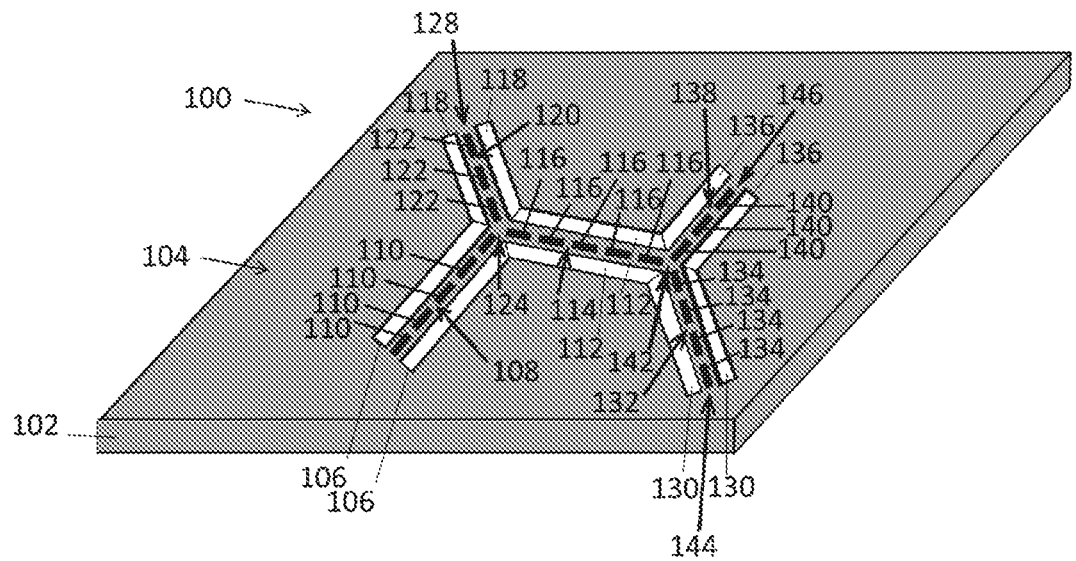
FIG. 3 is a schematic of an exemplary device as disclosed herein.

Referring now to FIG. 3, in some examples, the device 100 further comprises a fourth pair of alternating current (AC) electrodes 130 disposed on the surface 104 of the insulating substrate 102, wherein each of the AC electrodes comprising the fourth pair of AC electrodes 130 is spaced apart on the surface 104 of the insulating substrate 102 such that the fourth pair of AC electrodes 130 define a fourth arm of a channel 132.

In some examples, the dimension of each of the AC electrodes comprising the fourth pair of AC electrodes 130 within the plane of the surface 104 measured parallel to the length of the fourth arm of the channel 132 can be 10 millimeters (mm) or more (e.g., 11 mm or more, 12 mm or more, 13 mm or more, 14 mm or more, 15 mm or more, 16 mm or more, 17 mm or more, 18 mm or more, 19 mm or more, 20 mm or more, 21 mm or more, 22 mm or more, 23 mm or more, 24 mm or more, 25 mm or more, 26 mm or more, 27 mm or more, 28 mm or more, 29 mm or more, 30 mm or more, 35 mm or more, 40 mm or more, 45 mm or more, 50 mm or more, 55 mm or more, 60 mm or more, 65 mm or more, 70 mm or more, 75 mm or more, 80 mm or more, 85 mm or more, 90 mm or more, or 95 mm or more). In some examples, the dimension of each of the AC electrodes comprising the fourth pair of AC electrodes 130 within the plane of the surface 104 measured parallel to the length of the fourth arm of the channel 132 can be 100 mm or less (e.g., 95 mm or less, 90 mm or less, 85 mm or less, 80 mm or less, 75 mm or less, 70 mm or less, 65 mm or less, 60 mm or less, 55 mm or less, 50 mm or less, 45 mm or less, 40 mm or less, 35 mm or less, 30 mm or less, 29 mm or less, 28 mm or less, 27 mm or less, 26 mm or less, 25 mm or less, 24 mm or less, 23 mm or less, 22 mm or less, 21 mm or less, 20 mm or less, 19 mm or less, 18 mm or less, 17 mm or less, 16 mm or less, or 15 mm or less). The dimension of each of the AC electrodes comprising the fourth pair of AC electrodes 130 within the plane of the surface 104 measured parallel to the length of the fourth arm of the channel 132 can range from any of the minimum values described above to any of the maximum values described above. For example, the dimension of each of the AC electrodes comprising the fourth pair of AC electrodes 130 within the plane of the surface 104 measured parallel to the length of the fourth arm of the channel 132 can be from 10 mm to 100 mm (e.g., from 10 mm to 55 mm, from 55 mm to 100 mm, from 10 mm to 40 mm, from 40 mm to 70 mm, from 70 mm to 100 mm, from 10 mm to 80 mm, from 20 mm to 60 mm, or from 20 mm to 30 mm). In some examples, the dimension of each of the AC electrodes comprising the fourth pair of AC electrodes 130 within the plane of the surface 104 measured parallel to the length of the fourth arm of the channel 132 can be substantially the same as the length of the fourth arm of the channel 132.

In some examples, the dimension of each of the AC electrodes comprising the fourth pair of AC electrodes 130 within the plane of the surface 104 measured perpendicular to the length of the fourth arm of the channel 132 can be 300 micrometers (μm) or more (e.g., 320 μm or more, 340 μm or more, 360 μm or more, 380 μm or more, 400 μm or more, 450 μm or more, 500 μm or more, 550 μm or more, 600 μm or more, 700 μm or more, 800 μm or more, 900 μm or more, 1000 μm or more, 1250 μm or more, 1500 μm or more, 1750 μm or more, 2000 μm or more, 2500 μm or more, 3000 μm or more, or 3500 μm or more). In some examples, the dimension of each of the AC electrodes comprising the fourth pair of AC electrodes 130 within the plane of the surface 104 measured perpendicular to the length of the fourth arm of the channel 132 can be 4000 μm or less (e.g., 3500 μm or less, 3000 μm or less, 2500 μm or less, 2000 μm or less, 1750 μm or less, 1500 μm or less, 1250 μm or less, 1000 μm or less, 900 μm or less, 800 μm or less, 700 μm or less, 600 μm or less, 550 μm or less, 500 μm or less, 450 μm or less, 400 μm or less, 380 μm or less, 360 μm or less, 340 μm or less, or 320 μm or less). The dimension of each of the AC electrodes comprising the fourth pair of AC electrodes 130 within the plane of the surface 104 measured perpendicular to the length of the fourth arm of the channel 132 can range from any of the minimum values described above to any of the maximum values described above. For example, the dimension of each of the AC electrodes comprising the fourth pair of AC electrodes 130 within the plane of the surface 104 measured perpendicular to the length of the fourth arm of the channel 132 can be from 300 μm to 4000 μm (e.g., from 300 μm to 2000 μm, from 2000 μm to 4000 μm, from 300 μm to 800 μm, from 800 μm to 1250 μm, from 1250 μm to 1750 μm, from 1750 μm to 2500 μm, from 2500 μm to 3000 μm, from 3000 μm to 3500 μm, from 3500 μm to 4000 μm, or from 380 μm to 4000 μm). The length of the fourth arm of the channel 132 can, for example, be 10 millimeters (mm) or more (e.g., 11 mm or more, 12 mm or more, 13 mm or more, 14 mm or more, 15 mm or more, 16 mm or more, 17 mm or more, 18 mm or more, 19 mm or more, 20 mm or more, 21 mm or more, 22 mm or more, 23 mm or more, 24 mm or more, 25 mm or more, 26 mm or more, 27 mm or more, 28 mm or more, 29 mm or more, 30 mm or more, 35 mm or more, 40 mm or more, 45 mm or more, 50 mm or more, 55 mm or more, 60 mm or more, 65 mm or more, 70 mm or more, 75 mm or more, 80 mm or more, 85 mm or more, 90 mm or more, or 95 mm or more). In some examples, the length of the fourth arm of the channel 132 can be 100 mm or less (e.g., 95 mm or less, 90 mm or less, 85 mm or less, 80 mm or less, 75 mm or less, 70 mm or less, 65 mm or less, 60 mm or less, 55 mm or less, 50 mm or less, 45 mm or less, 40 mm or less, 35 mm or less, 30 mm or less, 29 mm or less, 28 mm or less, 27 mm or less, 26 mm or less, 25 mm or less, 24 mm or less, 23 mm or less, 22 mm or less, 21 mm or less, 20 mm or less, 19 mm or less, 18 mm or less, 17 mm or less, 16 mm or less, or 15 mm or less). The length of the fourth arm of the channel 132 can range from any of the minimum values described above to any of the maximum values described above. For example, the length of the fourth arm of the channel 132 can be from 10 mm to 100 mm (e.g., from 10 mm to 55 mm, from 55 mm to 100 mm, from 10 mm to 40 mm, from 40 mm to 70 mm, from 70 mm to 100 mm, from 10 mm to 80 mm, from 20 mm to 60 mm, or from 20 mm to 30 mm). In some examples, the length of the fourth arm of the channel 132 is the same as the length of the first arm of the channel 108, the second arm of the channel 114, the third arm of the channel 120, or a combination thereof.

The device 100 can further comprise a fourth direct current (DC) electrode 134 disposed on the surface 104 of the insulating substrate 102 and interspersed within the fourth arm of the channel 132. As used herein, a "fourth DC electrode" and "the fourth DC electrode" are meant to include any number of DC electrodes disposed on the surface of the insulating substrate and interspersed within the fourth arm of the channel. Thus, for example, "the fourth DC electrode" includes one or more fourth DC electrodes. In some examples, the fourth DC electrode 134 can comprise a fourth plurality of DC electrodes. In some examples, the fourth DC electrode 134 comprises more than 1 DC electrodes (e.g., 2 or more, 3 or more, 4 or more, 5 or more, 6 or more, 7 or more, 8 or more, 9 or more, 10 or more, 11 or more, 12 or more, 13 or more, 14 or more, or 15 or more). In some examples, the fourth DC electrode comprises from 5 to 15 DC electrodes (e.g., from 6-14 DC electrodes, or from 8-14 DC electrodes). The number of DC electrodes comprising the fourth DC electrode can be selected, for example, in view of length of the fourth arm of the channel. In some examples, there can be 5-10 DC electrodes per 10 mm of the length of the arm of the channel.

The cross-section within the plane of the surface 104 of the insulating substrate 102 of the fourth DC electrode 134 can be of any shape (e.g., a circle, a quadrilateral, an ellipse, a triangle, a polygon, etc.). In some examples, the cross-section within the plane of the surface 104 of the insulating substrate 102 of the fourth DC electrode 134 is a quadrilateral (e.g., a rectangle, a parallelogram, or the like). In some examples, the cross-section within the plane of the surface 104 of the insulating substrate 102 of the fourth DC electrode 134 is substantially rectangular. The substantially rectangular cross-section of the fourth DC electrode 134 can, for example, have a length and a width. In some examples, the width of the substantially rectangular cross-section of the fourth DC electrode 134 can be 300 µm or more (e.g., 320 µm or more, 340 µm or more, 360 µm or more, 380 µm or more, 400 µm or more, 420 µm or more, 440 µm or more, 460 µm or more, 480 µm or more, 500 µm or more, 520 µm or more, 540 µm or more, 560 µm or more, or 580 µm or more). In some examples, the width of the substantially rectangular cross-section of the fourth DC electrode 134 can be 600 µm or less (e.g., 580 µm or less, 560 µm or less, 540 µm or less, 520 µm or less, 500 µm or less, 480 µm or less, 460 µm or less, 440 µm or less, 420 µm or less, 400 µm or less, 380 µm or less, 360 µm or less, 340 µm or less, or 320 µm or less). The width of the substantially rectangular cross-section of the fourth DC electrode 134 can range from any of the minimum values described above to any of the maximum values described above. For example, the width of the substantially rectangular cross-section of the fourth DC electrode 134 can be from 300 µm to 600 µm (e.g., from 300 µm to 440 µm, from 440 µm to 600 µm, from 300 µm to 400 µm, from 400 µm to 500 µm, from 500 µm to 600 µm, or from 360 µm to 400 µm).

The length of the substantially rectangular cross-section of the fourth DC electrode 134 can be 1-4 times the width. In some examples, the length of the substantially rectangular cross-section of the fourth DC electrode 134 can be 300 µm or more (e.g., 320 µm or more, 340 µm or more, 360 µm or more, 380 µm or more, 400 µm or more, 420 µm or more, 440 µm or more, 460 µm or more, 480 µm or more, 500 µm or more, 520 µm or more, 540 µm or more, 560 µm or more, 580 µm or more, 600 µm or more, 650 µm or more, 700 µm or more, 750 µm or more, 800 µm or more, 850 µm or more, 900 µm or more, 950 µm or more, 1000 µm or more, 1100 µm or more, 1200 µm or more, 1300 µm or more, 1400 µm or more, 1500 µm or more, 1750 µm or more, 2000 µm or more, or 2250 µm or more). In some examples, the length of the substantially rectangular cross-section of the fourth DC electrode 134 can be 2400 µm or less (e.g., 2250 µm or less, 2000 µm or less, 1750 µm or less, 1500 µm or less, 1400 µm or less, 1300 µm or less, 1200 µm or less, 1100 µm or less, 1000 µm or less, 950 µm or less, 900 µm or less, 850 µm or less, 800 µm or less, 750 µm or less, 700 µm or less, 650 µm or less, 600 µm or less, 580 µm or less, 560 µm or less, 540 µm or less, 520 µm or less, 500 µm or less, 480 µm or less, 460 µm or less, 440 µm or less, 420 µm or less, 400 µm or less, 380 µm or less, 360 µm or less, 340 µm or less, or 320 µm or less). The length of the substantially rectangular cross-section of the fourth DC electrode 134 can range from any of the minimum values described above to any of the maximum values described above. For example, the length of the substantially rectangular cross-section of the fourth DC electrode 134 can be from 300 µm to 2400 µm (e.g., from 300 µm to 1200 µm, from 1200 µm to 2400 µm, from 300 µm to 600 µm, from 600 µm to 900 µm, from 900 µm to 1200 µm, from 1200 µm to 1800 µm, from 1800 µm to 2400 µm, or from 300 µm to 1600 µm).

In some examples, each of the AC electrodes within the forth pair of AC electrodes 130 is separated from the fourth DC electrode 134 by a seventh distance of 450 µm or more (e.g., 475 µm or more, 500 µm or more, 525 µm or more, 550 µm or more, 575 µm or more, 600 µm or more, 650 µm or more, 700 µm or more, 750 µm or more, 800 µm or more, 850 µm or more, 900 µm or more, 950 µm or more, 1000 µm or more, 1050 µm or more, 1100 µm or more, 1150 µm or more, 1200 µm or more, or 1250 µm or more), In some examples, each of the AC electrodes within the forth pair of AC electrodes 130 is separated from the fourth DC electrode 134 by a seventh distance of 1270 µm or less (e.g., 1250 µm or less, 1200 µm or less, 1150 µm or less, 1100 µm or less, 1050 µm or less, 1000 µm or less, 950 µm or less, 900 µm or less, 850 µm or less, 800 µm or less, 750 µm or less, 700 µm or less, 650 µm or less, 600 µm or less, 575 µm or less, 550 µm or less, 525 µm or less, 500 µm or less, or 475 µm or less). The seventh distance can range from any of the minimum values described above to any of the maximum values described above. For example, each of the AC electrodes within the fourth pair of AC electrodes 130 is separated from the fourth DC electrode 134 by a seventh distance of from 450 µm to 1270 µm (e.g., from 450 µm to 850 µm, from 850 µm to 1270 µm, from 450 µm to 600 µm, from 600 µm 750 µm, from 750 µm to 900 µm, from 900 µm to 1050 µm, from 1050 µm to 1270 µm, from 475 µm to 1270 µm, or from 600 µm to 1270 µm). In some examples, the seventh distance is the same as the first distance, the third distance, the fifth distance, or a combination thereof.

In some examples, the fourth DC electrode 134 comprises a fourth plurality of DC electrodes and each DC electrode within the fourth plurality of DC electrodes is separated from its nearest neighboring DC electrode by an eighth distance of 150 µm or more (e.g., 170 µm or more, 190 µm or more, 210 µm or more, 230 µm or more, 250 µm or more, 275 µm or more, 300 µm or more, 325 µm or more, 350 µm or more, 375 µm or more, 400 µm or more, 425 µm or more, 450 µm or more, 475 µm or more, 500 µm or more, 550 µm or more, 600 µm or more, 650 µm or more, 700 µm or more, 750 µm or more, 800 µm or more, 900 µm or more, 1000 µm or more, 1100 µm or more, or 1200 µm or more), In some examples, the fourth DC electrode 134 comprises a fourth plurality of DC electrodes and each DC electrode within the fourth plurality of DC electrodes is separated from its nearest neighboring DC electrode by an eighth distance of 1270 µm or less (e.g., 1200 µm or less, 1100 µm or less, 1000 µm or less, 900 µm or less, 800 µm or less, 750 µm or less, 700 µm or less, 650 µm or less, 600 µm or less, 550 µm or less, 500 µm or less, 475 µm or less, 450 µm or less, 425 µm or less, 400 µm or less, 375 µm or less, 350 µm or less, 325 µm or less, 300 µm or less, 275 µm or less, 250 µm or less, 230 µm or less, 210 µm or less, 190 µm or less, or 170 µm or less). The eighth distance can range from any of the minimum values described above to any of the maximum values described above. For example, the fourth DC electrode 134 comprises a fourth plurality of DC electrodes and each DC electrode within the fourth plurality of DC electrodes is separated from its nearest neighboring DC electrode by an eighth distance of from 150 µm to 1270 µm (e.g., from 150 µm to 700 µm, from 700 µm to 1270 µm, from 150 µm to 300 µm, from 300 µm to 450 µm, from 450 µm to 600 µm, from 600 µm to 750 µm, from 750 µm to 900 µm, from 900 µm to 1050 µm, from 1050 µm to 1270 µm, from 190 µm to 1270 µm, or from 190 µm to 600 µm). In some examples, the eighth distance is from 190 µm to the seventh distance. In some examples, the seventh distance and the eighth distance are different. In some examples, the eighth distance is the same as the second distance, the fourth distance, the sixth distance, or a combination thereof.

The device 100 can, for example, further comprise a fifth pair of alternating current (AC) electrodes 136 disposed on the surface 104 of the insulating substrate 102, wherein each of the AC electrodes comprising the fifth pair of AC electrodes 136 is spaced apart on the surface 104 of the insulating substrate 102 such that the fifth pair of AC electrodes 136 define a fifth arm of a channel 138.

In some examples, the dimension of each of the AC electrodes comprising the fifth pair of AC electrodes 136 within the plane of the surface 104 measured parallel to the length of the fifth arm of the channel 138 can be 10 millimeters (mm) or more (e.g., 11 mm or more, 12 mm or more, 13 mm or more, 14 mm or more, 15 mm or more, 16 mm or more, 17 mm or more, 18 mm or more, 19 mm or more, 20 mm or more, 21 mm or more, 22 mm or more, 23 mm or more, 24 mm or more, 25 mm or more, 26 mm or more, 27 mm or more, 28 mm or more, 29 mm or more, 30 mm or more, 35 mm or more, 40 mm or more, 45 mm or more, 50 mm or more, 55 mm or more, 60 mm or more, 65 mm or more, 70 mm or more, 75 mm or more, 80 mm or more, 85 mm or more, 90 mm or more, or 95 mm or more). In some examples, the dimension of each of the AC electrodes comprising the fifth pair of AC electrodes 136 within the plane of the surface 104 measured parallel to the length of the fifth arm of the channel 138 can be 100 mm or less (e.g., 95 mm or less, 90 mm or less, 85 mm or less, 80 mm or less, 75 mm or less, 70 mm or less, 65 mm or less, 60 mm or less, 55 mm or less, 50 mm or less, 45 mm or less, 40 mm or less, 35 mm or less, 30 mm or less, 29 mm or less, 28 mm or less, 27 mm or less, 26 mm or less, 25 mm or less, 24 mm or less, 23 mm or less, 22 mm or less, 21 mm or less, 20 mm or less, 19 mm or less, 18 mm or less, 17 mm or less, 16 mm or less, or 15 mm or less). The dimension of each of the AC electrodes comprising the fifth pair of AC electrodes 136 within the plane of the surface 104 measured parallel to the length of the fifth arm of the channel 138 can range from any of the minimum values described above to any of the maximum values described above. For example, the dimension of each of the AC electrodes comprising the fifth pair of AC electrodes 136 within the plane of the surface 104 measured parallel to the length of the fifth arm of the channel 138 can be from 10 mm to 100 mm (e.g., from 10 mm to 55 mm, from 55 mm to 100 mm, from 10 mm to 40 mm, from 40 mm to 70 mm, from 70 mm to 100 mm, from 10 mm to 80 mm, from 20 mm to 60 mm, or from 20 mm to 30 mm). In some examples, the dimension of each of the AC electrodes comprising the fifth pair of AC electrodes 136 within the plane of the surface 104 measured parallel to the length of the fifth arm of the channel 138 can be substantially the same as the length of the fifth arm of the channel 138.

In some examples, the dimension of each of the AC electrodes comprising the fifth pair of AC electrodes 136 within the plane of the surface 104 measured perpendicular to the length of the fifth arm of the channel 138 can be 300 micrometers (µm) or more (e.g., 320 µm or more, 340 µm or more, 360 µm or more, 380 µm or more, 400 µm or more, 450 µm or more, 500 µm or more, 550 µm or more, 600 µm or more, 700 µm or more, 800 µm or more, 900 µm or more, 1000 µm or more, 1250 µm or more, 1500 µm or more, 1750 µm or more, 2000 µm or more, 2500 µm or more, 3000 µm or more, or 3500 µm or more). In some examples, the dimension of each of the AC electrodes comprising the fifth pair of AC electrodes 136 within the plane of the surface 104 measured perpendicular to the length of the fifth arm of the channel 138 can be 4000 µm or less (e.g., 3500 µm or less, 3000 µm or less, 2500 µm or less, 2000 µm or less, 1750 µm or less, 1500 µm or less, 1250 µm or less, 1000 µm or less, 900 µm or less, 800 µm or less, 700 µm or less, 600 µm or less, 550 µm or less, 500 µm or less, 450 µm or less, 400 µm or less, 380 µm or less, 360 µm or less, 340 µm or less, or 320 µm or less). The dimension of each of the AC electrodes comprising the fifth pair of AC electrodes 136 within the plane of the surface 104 measured perpendicular to the length of the fifth arm of the channel 138 can range from any of the minimum values described above to any of the maximum values described above. For example, the dimension of each of the AC electrodes comprising the fifth pair of AC electrodes 136 within the plane of the surface 104 measured perpendicular to the length of the fifth arm of the channel 138 can be from 300 µm to 4000 µm (e.g., from 300 µm to 2000 µm, from 2000 µm to 4000 µm, from 300 µm to 800 µm, from 800 µm to 1250 µm, from 1250 µm to 1750 µm, from 1750 µm to 2500 µm, from 2500 µm to 3000 µm, from 3000 µm to 3500 µm, from 3500 µm to 4000 µm, or from 380 µm to 4000 µm).

The length of the fifth arm of the channel 138 can, for example, be 10 millimeters (mm) or more (e.g., 11 mm or more, 12 mm or more, 13 mm or more, 14 mm or more, 15 mm or more, 16 mm or more, 17 mm or more, 18 mm or more, 19 mm or more, 20 mm or more, 21 mm or more, 22 mm or more, 23 mm or more, 24 mm or more, 25 mm or more, 26 mm or more, 27 mm or more, 28 mm or more, 29 mm or more, 30 mm or more, 35 mm or more, 40 mm or more, 45 mm or more, 50 mm or more, 55 mm or more, 60 mm or more, 65 mm or more, 70 mm or more, 75 mm or more, 80 mm or more, 85 mm or more, 90 mm or more, or 95 mm or more). In some examples, the length of the fifth arm of the channel 138 can be 100 mm or less (e.g., 95 mm or less, 90 mm or less, 85 mm or less, 80 mm or less, 75 mm or less, 70 mm or less, 65 mm or less, 60 mm or less, 55 mm or less, 50 mm or less, 45 mm or less, 40 mm or less, 35 mm or less, 30 mm or less, 29 mm or less, 28 mm or less, 27 mm or less, 26 mm or less, 25 mm or less, 24 mm or less, 23 mm or less, 22 mm or less, 21 mm or less, 20 mm or less, 19 mm or less, 18 mm or less, 17 mm or less, 16 mm or less, or 15 mm or less). The length of the fifth arm of the channel 138 can range from any of the minimum values described above to any of the maximum values described above. For example, the length of the fifth arm of the channel 138 can be from 10 mm to 100 mm (e.g., from 10 mm to 55 mm, from 55 mm to 100 mm, from 10 mm to 40 mm, from 40 mm to 70 mm, from 70 mm to 100 mm, from 10 mm to 80 mm, from 20 mm to 60 mm, or from 20 mm to 30 mm). In some examples, the length of the fifth arm of the channel 138 is the same as the length of the first arm of the channel 108, the second arm of the channel 114, the third arm of the channel 120, the fourth arm of the channel 132, or a combination thereof.

The device 100 can further comprise a fifth direct current (DC) electrode 140 disposed on the surface 104 of the insulating substrate 102 and interspersed within the fifth arm of the channel 138. As used herein, a "fifth DC electrode" and "the fifth DC electrode" are meant to include any number of DC electrodes disposed on the surface of the insulating substrate and interspersed within the fifth arm of the channel. Thus, for example, "the fifth DC electrode" includes one or more fifth DC electrodes. In some examples, the fifth DC electrode 140 can comprise a fifth plurality of DC electrodes. In some examples, the fifth DC electrode 140 comprises more than 1 DC electrodes (e.g., 2 or more, 3 or more, 4 or more, 5 or more, 6 or more, 7 or more, 8 or more, 9 or more, 10 or more, 11 or more, 12 or more, 13 or more, 14 or more, or 15 or more). In some examples, the fifth DC electrode comprises from 5 to 15 DC electrodes (e.g., from 6-14 DC electrodes, or from 8-14 DC electrodes). The number of DC electrodes comprising the fifth DC electrode can be selected, for example, in view of length of the fifth arm of the channel. In some examples, there can be 5-10 DC electrodes per 10 mm of the length of the arm of the channel.

The cross-section within the plane of the surface 104 of the insulating substrate 102 of the fifth DC electrode 140 can be of any shape (e.g., a circle, a quadrilateral, an ellipse, a triangle, a polygon, etc.). In some examples, the cross-section within the plane of the surface 104 of the insulating substrate 102 of the fifth DC electrode 140 is a quadrilateral (e.g., a rectangle, a parallelogram, or the like). In some examples, the cross-section within the plane of the surface 104 of the insulating substrate 102 of the fifth DC electrode 140 is substantially rectangular. The substantially rectangular cross-section of the fifth DC electrode 140 can, for example, have a length and a width. In some examples, the width of the substantially rectangular cross-section of the fifth DC electrode 140 can be 300 µm or more (e.g., 320 µm or more, 340 µm or more, 360 µm or more, 380 µm or more, 400 µm or more, 420 µm or more, 440 µm or more, 460 µm or more, 480 µm or more, 500 µm or more, 520 µm or more, 540 µm or more, 560 µm or more, or 580 µm or more). In some examples, the width of the substantially rectangular cross-section of the fifth DC electrode 140 can be 600 µm or less (e.g., 580 µm or less, 560 µm or less, 540 µm or less, 520 µm or less, 500 µm or less, 480 µm or less, 460 µm or less, 440 µm or less, 420 µm or less, 400 µm or less, 380 µm or less, 360 µm or less, 340 µm or less, or 320 µm or less). The width of the substantially rectangular cross-section of the fifth DC electrode 140 can range from any of the minimum values described above to any of the maximum values described above. For example, the width of the substantially rectangular cross-section of the fifth DC electrode 140 can be from 300 µm to 600 µm (e.g., from 300 µm to 440 µm, from 440 µm to 600 µm, from 300 µm to 400 µm, from 400 µm to 500 µm, from 500 µm to 600 µm, or from 360 µm to 400 µm).

The length of the substantially rectangular cross-section of the fifth DC electrode 140 can be 1-4 times the width. In some examples, the length of the substantially rectangular cross-section of the fifth DC electrode 140 can be 300 µm or more (e.g., 320 µm or more, 340 µm or more, 360 µm or more, 380 µm or more, 400 µm or more, 420 µm or more, 440 µm or more, 460 µm or more, 480 µm or more, 500 µm or more, 520 µm or more, 540 µm or more, 560 µm or more, 580 µm or more, 600 µm or more, 650 µm or more, 700 µm or more, 750 µm or more, 800 µm or more, 850 µm or more, 900 µm or more, 950 µm or more, 1000 µm or more, 1100 µm or more, 1200 µm or more, 1300 µm or more, 1400 µm or more, 1500 µm or more, 1750 µm or more, 2000 µm or more, or 2250 µm or more). In some examples, the length of the substantially rectangular cross-section of the fifth DC electrode 140 can be 2400 µm or less (e.g., 2250 µm or less, 2000 µm or less, 1750 µm or less, 1500 µm or less, 1400 µm or less, 1300 µm or less, 1200 µm or less, 1100 µm or less, 1000 µm or less, 950 µm or less, 900 µm or less, 850 µm or less, 800 µm or less, 750 µm or less, 700 µm or less, 650 µm or less, 600 µm or less, 580 µm or less, 560 µm or less, 540 µm or less, 520 µm or less, 500 µm or less, 480 µm or less, 460 µm or less, 440 µm or less, 420 µm or less, 400 µm or less, 380 µm or less, 360 µm or less, 340 µm or less, or 320 µm or less. The length of the substantially rectangular cross-section of the fifth DC electrode 140 can range from any of the minimum values described above to any of the maximum values described above. For example, the length of the substantially rectangular cross-section of the fifth DC electrode 140 can be from 300 µm to 2400 µm (e.g., from 300 µm to 1200 µm, from 1200 µm to 2400 µm, from 300 µm to 600 µm, from 600 µm to 900 µm, from 900 µm to 1200 µm, from 1200 µm to 1800 µm, from 1800 µm to 2400 µm, or from 300 µm to 1600 µm).

In some examples, each of the AC electrodes within the fifth pair of AC electrodes 136 is separated from the fifth DC electrode 140 by a ninth distance of 450 µm or more (e.g., 475 µm or more, 500 µm or more, 525 µm or more, 550 µm or more, 575 µm or more, 600 µm or more, 650 µm or more, 700 µm or more, 750 µm or more, 800 µm or more, 850 µm or more, 900 µm or more, 950 µm or more, 1000 µm or more, 1050 µm or more, 1100 µm or more, 1150 µm or more, 1200 µm or more, or 1250 µm or more). In some examples, each of the AC electrodes within the fifth pair of AC electrodes 136 is separated from the fifth DC electrode 140 by a ninth distance of 1270 µm or less (e.g., 1250 µm or less, 1200 µm or less, 1150 µm or less, 1100 µm or less, 1050 µm or less, 1000 µm or less, 950 µm or less, 900 µm or less, 850 µm or less, 800 µm or less, 750 µm or less, 700 µm or less, 650 µm or less, 600 µm or less, 575 µm or less, 550 µm or less, 525 µm or less, 500 µm or less, or 475 µm or less). The ninth distance can range from any of the minimum values described above to any of the maximum values described above. For example, each of the AC electrodes within the fifth pair of AC electrodes 136 is separated from the fifth DC electrode 140 by a ninth distance of from 450 µm to 1270 µm (e.g., from 450 µm to 850 µm, from 850 µm to 1270 µm, from 450 µm to 600 µm, from 600 µm 750 µm, from 750 µm to 900 µm, from 900 µm to 1050 µm, from 1050 µm to 1270 µm, from 475 µm to 1270 µm, or from 600 µm to 1270 µm). In some examples, the ninth distance is the same as the first distance, the third distance, the fifth distance, the seventh distance, or a combination thereof.

In some examples, the fifth DC electrode 140 comprises a fifth plurality of DC electrodes and each DC electrode within the fifth plurality of DC electrodes is separated from its nearest neighboring DC electrode by a tenth distance of 150 µm or more (e.g., 170 µm or more, 190 µm or more, 210 µm or more, 230 µm or more, 250 µm or more, 275 µm or more, 300 µm or more, 325 µm or more, 350 µm or more, 375 µm or more, 400 µm or more, 425 µm or more, 450 µm or more, 475 µm or more, 500 µm or more, 550 µm or more, 600 µm or more, 650 µm or more, 700 µm or more, 750 µm or more, 800 µm or more, 900 µm or more, 1000 µm or more, 1100 µm or more, or 1200 µm or more). In some examples, the fifth DC electrode 140 comprises a fifth plurality of DC electrodes and each DC electrode within the fifth plurality of DC electrodes is separated from its nearest neighboring DC electrode by a tenth distance of 1270 µm or less (e.g., 1200 µm or less, 1100 µm or less, 1000 µm or less, 900 µm or less, 800 µm or less, 750 µm or less, 700 µm or less, 650 µm or less, 600 µm or less, 550 µm or less, 500 µm or less, 475 µm or less, 450 µm or less, 425 µm or less, 400 µm or less, 375 µm or less, 350 µm or less, 325 µm or less, 300 µm or less, 275 µm or less, 250 µm or less, 230 µm or less, 210 µm or less, 190 µm or less, or 170 µm or less). The tenth distance can range from any of the minimum values described above to any of the maximum values described above. For example, the fifth DC electrode 140 comprises a fifth plurality of DC electrodes and each DC electrode within the fifth plurality of DC electrodes is separated from its nearest neighboring DC electrode by a tenth distance of from 150 µm to 1270 µm (e.g., from 150 µm to 700 µm, from 700 µm to 1270 µm, from 150 µm to 300 µm, from 300 µm to 450 µm, from 450 µm to 600 µm, from 600 µm to 750 µm, from 750 µm to 900 µm, from 900 µm to 1050 µm, from 1050 µm to 1270 µm, from 190 µm to 1270 µm, or from 190 µm to 600 µm). In some examples, the tenth distance is from 190 µm to the ninth distance. In some examples, the ninth distance and the tenth distance are different. In some examples, the tenth distance is the same as the second distance, the fourth distance, the sixth distance, the eighth distance, or a combination thereof.

The device 100 can further comprise a second junction 142, wherein the second 114, fourth 132, and fifth 138 arms of the channel intersect at a second junction 142. For example, the second arm of the channel 114 can split into the fourth 132 and fifth 138 arms of the channel at the second junction 142.

In some examples, the fourth arm of the channel 132 further comprises a collection region 144, such that the fourth arm of the channel 132 extends from the second junction 142 to the collection region 144.

In some examples, the fifth arm of the channel 138 further comprises a collection region 146, such that the fifth arm of the channel 138 extends from the second junction 142 to the collection region 146.

Figure 4:
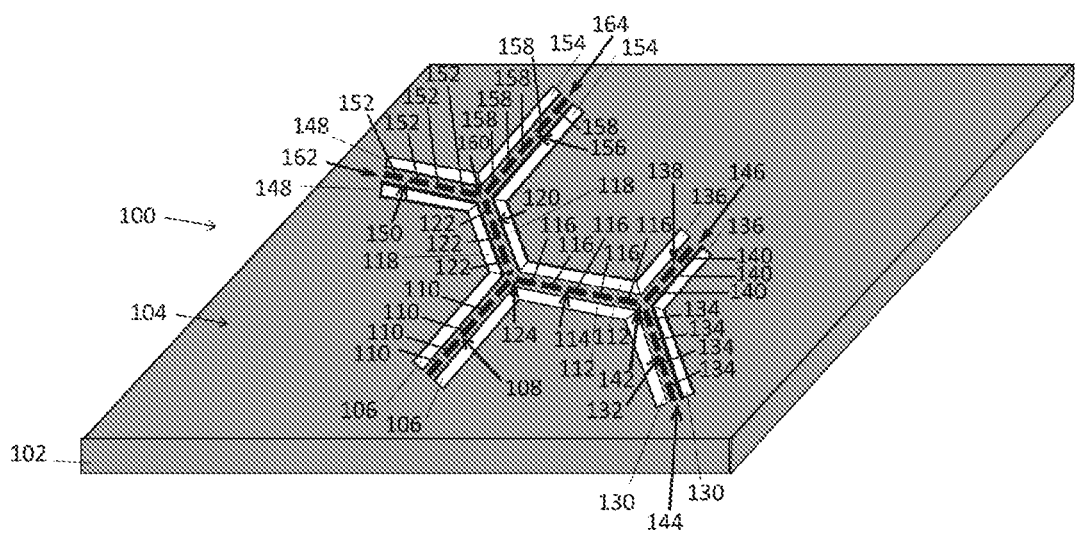
FIG. 4 is a schematic of an exemplary device as disclosed herein.

Referring now to FIG. 4, in some examples, the device 100 can further comprise a sixth pair of alternating current (AC) electrodes 148 disposed on the surface 104 of the insulating substrate 102, wherein each of the AC electrodes comprising the sixth pair of AC electrodes 148 is spaced apart on the surface 104 of the insulating substrate 102 such that the sixth pair of AC electrodes 148 define a sixth arm of a channel 150.

In some examples, the dimension of each of the AC electrodes comprising the sixth pair of AC electrodes 148 within the plane of the surface 104 measured parallel to the length of the sixth arm of the channel 150 can be 10 millimeters (mm) or more (e.g., 11 mm or more, 12 mm or more, 13 mm or more, 14 mm or more, 15 mm or more, 16 mm or more, 17 mm or more, 18 mm or more, 19 mm or more, 20 mm or more, 21 mm or more, 22 mm or more, 23 mm or more, 24 mm or more, 25 mm or more, 26 mm or more, 27 mm or more, 28 mm or more, 29 mm or more, 30 mm or more, 35 mm or more, 40 mm or more, 45 mm or more, 50 mm or more, 55 mm or more, 60 mm or more, 65 mm or more, 70 mm or more, 75 mm or more, 80 mm or more, 85 mm or more, 90 mm or more, or 95 mm or more). In some examples, the dimension of each of the AC electrodes comprising the sixth pair of AC electrodes 148 within the plane of the surface 104 measured parallel to the length of the sixth arm of the channel 150 can be 100 mm or less (e.g., 95 mm or less, 90 mm or less, 85 mm or less, 80 mm or less, 75 mm or less, 70 mm or less, 65 mm or less, 60 mm or less, 55 mm or less, 50 mm or less, 45 mm or less, 40 mm or less, 35 mm or less, 30 mm or less, 29 mm or less, 28 mm or less, 27 mm or less, 26 mm or less, 25 mm or less, 24 mm or less, 23 mm or less, 22 mm or less, 21 mm or less, 20 mm or less, 19 mm or less, 18 mm or less, 17 mm or less, 16 mm or less, or 15 mm or less). The dimension of each of the AC electrodes comprising the sixth pair of AC electrodes 148 within the plane of the surface 104 measured parallel to the length of the sixth arm of the channel 150 can range from any of the minimum values described above to any of the maximum values described above. For example, the dimension of each of the AC electrodes comprising the sixth pair of AC electrodes 148 within the plane of the surface 104 measured parallel to the length of the sixth arm of the channel 150 can be from 10 mm to 100 mm (e.g., from 10 mm to 55 mm, from 55 mm to 100 mm, from 10 mm to 40 mm, from 40 mm to 70 mm, from 70 mm to 100 mm, from 10 mm to 80 mm, from 20 mm to 60 mm, or from 20 mm to 30 mm). In some examples, the dimension of each of the AC electrodes comprising the sixth pair of AC electrodes 148 within the plane of the surface 104 measured parallel to the length of the sixth arm of the channel 150 can be substantially the same as the length of the sixth arm of the channel 150.

In some examples, the dimension of each of the AC electrodes comprising the sixth pair of AC electrodes 148 within the plane of the surface 104 measured perpendicular to the length of the sixth arm of the channel 150 can be 300 micrometers (µm) or more (e.g., 320 µm or more, 340 µm or more, 360 µm or more, 380 µm or more, 400 µm or more, 450 µm or more, 500 µm or more, 550 µm or more, 600 µm or more, 700 µm or more, 800 µm or more, 900 µm or more, 1000 µm or more, 1250 µm or more, 1500 µm or more, 1750 µm or more, 2000 µm or more, 2500 µm or more, 3000 µm or more, or 3500 µm or more). In some examples, the dimension of each of the AC electrodes comprising the sixth pair of AC electrodes 148 within the plane of the surface 104 measured perpendicular to the length of the sixth arm of the channel 150 can be 4000 µm or less (e.g., 3500 µm or less, 3000 µm or less, 2500 µm or less, 2000 µm or less, 1750 µm or less, 1500 µm or less, 1250 µm or less, 1000 µm or less, 900 µm or less, 800 µm or less, 700 µm or less, 600 µm or less, 550 µm or less, 500 µm or less, 450 µm or less, 400 µm or less, 380 µm or less, 360 µm or less, 340 µm or less, or 320 µm or less). The dimension of each of the AC electrodes comprising the sixth pair of AC electrodes 148 within the plane of the surface 104 measured perpendicular to the length of the sixth arm of the channel 150 can range from any of the minimum values described above to any of the maximum values described above. For example, the dimension of each of the AC electrodes comprising the sixth pair of AC electrodes 148 within the plane of the surface 104 measured perpendicular to the length of the sixth arm of the channel 150 can be from 300 µm to 4000 µm (e.g., from 300 µm to 2000 µm, from 2000 µm to 4000 µm, from 300 µm to 800 µm, from 800 µm to 1250 µm, from 1250 µm to 1750 µm, from 1750 µm to 2500 µm, from 2500 µm to 3000 µm, from 3000 µm to 3500 µm, from 3500 µm to 4000 µm, or from 380 µm to 4000 µm). The length of the sixth arm of the channel 150 can, for example, be 10 millimeters (mm) or more (e.g., 11 mm or more, 12 mm or more, 13 mm or more, 14 mm or more, 15 mm or more, 16 mm or more, 17 mm or more, 18 mm or more, 19 mm or more, 20 mm or more, 21 mm or more, 22 mm or more, 23 mm or more, 24 mm or more, 25 mm or more, 26 mm or more, 27 mm or more, 28 mm or more, 29 mm or more, 30 mm or more, 35 mm or more, 40 mm or more, 45 mm or more, 50 mm or more, 55 mm or more, 60 mm or more, 65 mm or more, 70 mm or more, 75 mm or more, 80 mm or more, 85 mm or more, 90 mm or more, or 95 mm or more). In some examples, length of the sixth arm of the channel 150 can be 100 mm or less (e.g., 95 mm or less, 90 mm or less, 85 mm or less, 80 mm or less, 75 mm or less, 70 mm or less, 65 mm or less, 60 mm or less, 55 mm or less, 50 mm or less, 45 mm or less, 40 mm or less, 35 mm or less, 30 mm or less, 29 mm or less, 28 mm or less, 27 mm or less, 26 mm or less, 25 mm or less, 24 mm or less, 23 mm or less, 22 mm or less, 21 mm or less, 20 mm or less, 19 mm or less, 18 mm or less, 17 mm or less, 16 mm or less, or 15 mm or less). The length of the sixth arm of the channel 150 can range from any of the minimum values described above to any of the maximum values described above. For example, length of the sixth arm of the channel 150 can be from 10 mm to 100 mm (e.g., from 10 mm to 55 mm, from 55 mm to 100 mm, from 10 mm to 40 mm, from 40 mm to 70 mm, from 70 mm to 100 mm, from 10 mm to 80 mm, from 20 mm to 60 mm, or from 20 mm to 30 mm). In some examples, the length of the sixth arm of the channel 150 is the same as the length of the first arm of the channel 108, the second arm of the channel 114, the third arm of the channel 120, the fourth arm of the channel 132, the fifth arm of the channel 138, or a combination thereof.

The device 100 can further comprise a sixth direct current (DC) electrode 152 disposed on the surface 104 of the insulating substrate 102 and interspersed within the sixth arm of the channel 150. As used herein, a "sixth DC electrode" and "the sixth DC electrode" are meant to include any number of DC electrodes disposed on the surface of the insulating substrate and interspersed within the sixth arm of the channel. Thus, for example, "the sixth DC electrode" includes one or more sixth DC electrodes. In some examples, the sixth DC electrode 152 can comprise a sixth plurality of DC electrodes. In some examples, the sixth DC electrode 152 comprises more than 1 DC electrodes (e.g., 2 or more, 3 or more, 4 or more, 5 or more, 6 or more, 7 or more, 8 or more, 9 or more, 10 or more, 11 or more, 12 or more, 13 or more, 14 or more, or 15 or more). In some examples, the sixth DC electrode comprises from 5 to 15 DC electrodes (e.g., from 6-14 DC electrodes, or from 8-14 DC electrodes). The number of DC electrodes comprising the sixth DC electrode can be selected, for example, in view of length of the sixth arm of the channel. In some examples, there can be 5-10 DC electrodes per 10 mm of the length of the arm of the channel.

The cross-section within the plane of the surface 104 of the insulating substrate 102 of the sixth DC electrode 152 can be of any shape (e.g., a circle, a quadrilateral, an ellipse, a triangle, a polygon, etc.). In some examples, the cross-section within the plane of the surface 104 of the insulating substrate 102 of the sixth DC electrode 152 is a quadrilateral (e.g., a rectangle, a parallelogram, or the like). In some examples, the cross-section within the plane of the surface 104 of the insulating substrate 102 of the sixth DC electrode 152 is substantially rectangular. The substantially rectangular cross-section of the sixth DC electrode 152 can, for example, have a length and a width. In some examples, the width of the substantially rectangular cross-section of the sixth DC electrode 152 can be 300 µm or more (e.g., 320 µm or more, 340 µm or more, 360 µm or more, 380 µm or more, 400 µm or more, 420 µm or more, 440 µm or more, 460 µm or more, 480 µm or more, 500 µm or more, 520 µm or more, 540 µm or more, or 580 µm or more). In some examples, the width of the substantially rectangular cross-section of the sixth DC electrode 152 can be 600 µm or less (e.g., 580 µm or less, 560 µm or less, 540 µm or less, 520 µm or less, 500 µm or less, 480 µm or less, 460 µm or less, 440 µm or less, 420 µm or less, 400 µm or less, 380 µm or less, 360 µm or less, 340 µm or less, or 320 µm or less). The width of the substantially rectangular cross-section of the sixth DC electrode 152 can range from any of the minimum values described above to any of the maximum values described above. For example, the width of the substantially rectangular cross-section of the sixth DC electrode 152 can be from 300 µm to 600 µm (e.g., from 300 µm to 440 µm, from 440 µm to 600 µm, from 300 µm to 400 µm, from 400 µm to 500 µm, from 500 µm to 600 µm, or from 360 µm to 400 µm).

The length of the substantially rectangular cross-section of the sixth DC electrode 152 can be 1-4 times the width. In some examples, the length of the substantially rectangular cross-section of the sixth DC electrode 152 can be 300 µm or more (e.g., 320 µm or more, 340 µm or more, 360 µm or more, 380 µm or more, 400 µm or more, 420 µm or more, 440 µm or more, 460 µm or more, 480 µm or more, 500 µm or more, 520 µm or more, 540 µm or more, 560 µm or more, 580 µm or more, 600 µm or more, 650 µm or more, 700 µm or more, 750 µm or more, 800 µm or more, 850 µm or more, 900 µm or more, 950 µm or more, 1000 µm or more, 1100 µm or more, 1200 µm or more, 1300 µm or more, 1400 µm or more, 1500 µm or more, 1750 µm or more, 2000 µm or more, or 2250 µm or more). In some examples, the length of the substantially rectangular cross-section of the sixth DC electrode 152 can be 2400 µm or less (e.g., 2250 µm or less, 2000 µm or less, 1750 µm or less, 1500 µm or less, 1400 µm or less, 1300 µm or less, 1200 µm or less, 1100 µm or less, 1000 µm or less, 950 µm or less, 900 µm or less, 850 µm or less, 800 µm or less, 750 µm or less, 700 µm or less, 650 µm or less, 600 µm or less, 580 µm or less, 560 µm or less, 540 µm or less, 520 µm or less, 500 µm or less, 480 µm or less, 460 µm or less, 440 µm or less, 420 µm or less, 400 µm or less, 380 µm or less, 360 µm or less, 340 µm or less, or 320 µm or less. The length of the substantially rectangular cross-section of sixth DC electrode 152 can range from any of the minimum values described above to any of the maximum values described above. For example, the length of the substantially rectangular cross-section of the sixth DC electrode 152 can be from 300 µm to 2400 µm (e.g., from 300 µm to 1200 µm, from 1200 µm to 2400 µm, from 300 µm to 600 µm, from 600 µm to 900 µm, from 900 µm to 1200 µm, from 1200 µm to 1800 µm, from 1800 µm to 2400 µm, or from 300 µm to 1600 µm).

In some examples, each of the AC electrodes within the sixth pair of AC electrodes 148 is separated from the sixth DC electrode 152 by an eleventh distance of 450 µm or more (e.g., 475 µm or more, 500 µm or more, 525 µm or more, 550 µm or more, 575 µm or more, 600 µm or more, 650 µm or more, 700 µm or more, 750 µm or more, 800 µm or more, 850 µm or more, 900 µm or more, 950 µm or more, 1000 µm or more, 1050 µm or more, 1100 µm or more, 1150 µm or more, 1200 µm or more, or 1250 µm or more), In some examples, each of the AC electrodes within the sixth pair of AC electrodes 148 is separated from the sixth DC electrode 152 by an eleventh distance of 1270 µm or less (e.g., 1250 µm or less, 1200 µm or less, 1150 µm or less, 1100 µm or less, 1050 µm or less, 1000 µm or less, 950 µm or less, 900 µm or less, 850 µm or less, 800 µm or less, 750 µm or less, 700 µm or less, 650 µm or less, 600 µm or less, 575 µm or less, 550 µm or less, 525 µm or less, 500 µm or less, or 475 µm or less). The eleventh distance can range from any of the minimum values described above to any of the maximum values described above. For example, each of the AC electrodes within the sixth pair of AC electrodes 148 is separated from the sixth DC electrode 152 by an eleventh distance of from 450 μm to 1270 μm (e.g., from 450 μm to 850 μm, from 850 μm to 1270 μm, from 450 μm to 600 μm, from 600 μm 750 μm, from 750 μm to 900 μm, from 900 μm to 1050 μm, from 1050 μm to 1270 μm, from 475 μm to 1270 μm, or from 600 μm to 1270 μm). In some examples, the eleventh distance is the same as the first distance, the third distance, the fifth distance, the seventh distance, the ninth distance, or a combination thereof.

In some examples, the sixth DC electrode 152 comprises a sixth plurality of DC electrodes and each DC electrode within the sixth plurality of DC electrodes is separated from its nearest neighboring DC electrode by a twelfth distance of 150 μm or more (e.g., 170 μm or more, 190 μm or more, 210 μm or more, 230 μm or more, 250 μm or more, 275 μm or more, 300 μm or more, 325 μm or more, 350 μm or more, 375 μm or more, 400 μm or more, 425 μm or more, 450 μm or more, 475 μm or more, 500 μm or more, 550 μm or more, 600 μm or more, 650 μm or more, 700 μm or more, 750 μm or more, 800 μm or more, 900 μm or more, 1000 μm or more, 1100 μm or more, or 1200 μm or more). In some examples, the sixth DC electrode 152 comprises a sixth plurality of DC electrodes and each DC electrode within the sixth plurality of DC electrodes is separated from its nearest neighboring DC electrode by a twelfth distance of 1270 μm or less (e.g., 1200 μm or less, 1100 μm or less, 1000 μm or less, 900 μm or less, 800 μm or less, 750 μm or less, 700 μm or less, 650 μm or less, 600 μm or less, 550 μm or less, 500 μm or less, 475 μm or less, 450 μm or less, 425 μm or less, 400 μm or less, 375 μm or less, 350 μm or less, 325 μm or less, 300 μm or less, 275 μm or less, 250 μm or less, 230 μm or less, 210 μm or less, 190 μm or less, or 170 μm or less). The twelfth distance can range from any of the minimum values described above to any of the maximum values described above. For example, the sixth DC electrode 152 comprises a sixth plurality of DC electrodes and each DC electrode within the sixth plurality of DC electrodes is separated from its nearest neighboring DC electrode by a twelfth distance of from 150 μm to 1270 μm (e.g., from 150 μm to 700 μm, from 700 μm to 1270 μm, from 150 μm to 300 μm, from 300 μm to 450 μm, from 450 μm to 600 μm, from 600 μm to 750 μm, from 750 μm to 900 μm, from 900 μm to 1050 μm, from 1050 μm to 1270 μm, from 190 μm to 1270 μm, or from 190 μm to 600 μm). In some examples, the twelfth distance is from 190 μm to the eleventh distance. In some examples, the eleventh distance and the twelfth distance are different. In some examples, the twelfth distance is the same as the second distance, the fourth distance, the sixth distance, the eighth distance, the tenth distance, or a combination thereof.

The device 100 can, for example, further comprise a seventh pair of alternating current (AC) electrodes 154 disposed on the surface 104 of the insulating substrate 102, wherein each of the AC electrodes comprising the seventh pair of AC electrodes 154 is spaced apart on the surface 104 of the insulating substrate 102 such that the seventh pair of AC electrodes 154 define a seventh arm of a channel 156.

In some examples, the dimension of each of the AC electrodes comprising the seventh pair of AC electrodes 154 within the plane of the surface 104 measured parallel to the length of the seventh arm of the channel 156 can be 10 millimeters (mm) or more (e.g., 11 mm or more, 12 mm or more, 13 mm or more, 14 mm or more, 15 mm or more, 16 mm or more, 17 mm or more, 18 mm or more, 19 mm or more, 20 mm or more, 21 mm or more, 22 mm or more, 23 mm or more, 24 mm or more, 25 mm or more, 26 mm or more, 27 mm or more, 28 mm or more, 29 mm or more, 30 mm or more, 35 mm or more, 40 mm or more, 45 mm or more, 50 mm or more, 55 mm or more, 60 mm or more, 65 mm or more, 70 mm or more, 75 mm or more, 80 mm or more, 85 mm or more, 90 mm or more, or 95 mm or more). In some examples, the dimension of each of the AC electrodes comprising the seventh pair of AC electrodes 154 within the plane of the surface 104 measured parallel to the length of the seventh arm of the channel 156 can be 100 mm or less (e.g., 95 mm or less, 90 mm or less, 85 mm or less, 80 mm or less, 75 mm or less, 70 mm or less, 65 mm or less, 60 mm or less, 55 mm or less, 50 mm or less, 45 mm or less, 40 mm or less, 35 mm or less, 30 mm or less, 29 mm or less, 28 mm or less, 27 mm or less, 26 mm or less, 25 mm or less, 24 mm or less, 23 mm or less, 22 mm or less, 21 mm or less, 20 mm or less, 19 mm or less, 18 mm or less, 17 mm or less, 16 mm or less, or 15 mm or less). The dimension of each of the AC electrodes comprising the seventh pair of AC electrodes 154 within the plane of the surface 104 measured parallel to the length of the seventh arm of the channel 156 can range from any of the minimum values described above to any of the maximum values described above. For example, the dimension of each of the AC electrodes comprising the seventh pair of AC electrodes 154 within the plane of the surface 104 measured parallel to the length of the seventh arm of the channel 156 can be from 10 mm to 100 mm (e.g., from 10 mm to 55 mm, from 55 mm to 100 mm, from 10 mm to 40 mm, from 40 mm to 70 mm, from 70 mm to 100 mm, from 10 mm to 80 mm, from 20 mm to 60 mm, or from 20 mm to 30 mm). In some examples, the dimension of each of the AC electrodes comprising the seventh pair of AC electrodes 154 within the plane of the surface 104 measured parallel to the length of the seventh arm of the channel 156 can be substantially the same as the length of the seventh arm of the channel 156.

In some examples, the dimension of each of the AC electrodes comprising the seventh pair of AC electrodes 154 within the plane of the surface 104 measured perpendicular to the length of the seventh arm of the channel 156 can be 300 micrometers (μm) or more (e.g., 320 μm or more, 340 μm or more, 360 μm or more, 380 μm or more, 400 μm or more, 450 μm or more, 500 μm or more, 550 μm or more, 600 μm or more, 700 μm or more, 800 μm or more, 900 μm or more, 1000 μm or more, 1250 μm or more, 1500 μm or more, 1750 μm or more, 2000 μm or more, 2500 μm or more, 3000 μm or more, or 3500 μm or more). In some examples, the dimension of each of the AC electrodes comprising the seventh pair of AC electrodes 154 within the plane of the surface 104 measured perpendicular to the length of the seventh arm of the channel 156 can be 4000 μm or less (e.g., 3500 μm or less, 3000 μm or less, 2500 μm or less, 2000 μm or less, 1750 μm or less, 1500 μm or less, 1250 μm or less, 1000 μm or less, 900 μm or less, 800 μm or less, 700 μm or less, 600 μm or less, 550 μm or less, 500 μm or less, 450 μm or less, 400 μm or less, 380 μm or less, 360 μm or less, 340 μm or less, or 320 μm or less). The dimension of each of the AC electrodes comprising the seventh pair of AC electrodes 154 within the plane of the surface 104 measured perpendicular to the length of the seventh arm of the channel 156 can range from any of the minimum values described above to any of the maximum values described above. For example, the dimension of each of the AC electrodes comprising the seventh pair of AC electrodes 154 within the plane of the surface 104 measured perpendicular to the length of the seventh arm of the channel 156 can be from 300 μm to 4000 μm (e.g., from 300 μm to 2000 μm, from 2000 μm to 4000 μm, from 300 μm to 800 μm, from 800 μm to 1250 μm, from 1250 μm to 1750 μm, from 1750 μm to 2500

μm, from 2500 μm to 3000 μm, from 3000 μm to 3500 μm, from 3500 μm to 4000 μm, or from 380 μm to 4000 μm).

The length of the seventh arm of the channel 156 can, for example, be 10 millimeters (mm) or more (e.g., 11 mm or more, 12 mm or more, 13 mm or more, 14 mm or more, 15 mm or more, 16 mm or more, 17 mm or more, 18 mm or more, 19 mm or more, 20 mm or more, 21 mm or more, 22 mm or more, 23 mm or more, 24 mm or more, 25 mm or more, 26 mm or more, 27 mm or more, 28 mm or more, 29 mm or more, 30 mm or more, 35 mm or more, 40 mm or more, 45 mm or more, 50 mm or more, 55 mm or more, 60 mm or more, 65 mm or more, 70 mm or more, 75 mm or more, 80 mm or more, 85 mm or more, 90 mm or more, or 95 mm or more). In some examples, the length of the seventh arm of the channel 156 can be 100 mm or less (e.g., 95 mm or less, 90 mm or less, 85 mm or less, 80 mm or less, 75 mm or less, 70 mm or less, 65 mm or less, 60 mm or less, 55 mm or less, 50 mm or less, 45 mm or less, 40 mm or less, 35 mm or less, 30 mm or less, 29 mm or less, 28 mm or less, 27 mm or less, 26 mm or less, 25 mm or less, 24 mm or less, 23 mm or less, 22 mm or less, 21 mm or less, 20 mm or less, 19 mm or less, 18 mm or less, 17 mm or less, 16 mm or less, or 15 mm or less). The length of the seventh arm of the channel 156 can range from any of the minimum values described above to any of the maximum values described above. For example, length of the seventh arm of the channel 156 can be from 10 mm to 100 mm (e.g., from 10 mm to 55 mm, from 55 mm to 100 mm, from 10 mm to 40 mm, from 40 mm to 70 mm, from 70 mm to 100 mm, from 10 mm to 80 mm, from 20 mm to 60 mm, or from 20 mm to 30 mm). In some examples, the length of the seventh arm of the channel 156 is the same as the length of the first arm of the channel 108, the second arm of the channel 114, the third arm of the channel 120, the fourth arm of the channel 132, the fifth arm of the channel 138, the sixth arm of the channel 150, or a combination thereof.

The device 100 can further comprise a seventh direct current (DC) electrode 158 disposed on the surface 104 of the insulating substrate 102 and interspersed within the seventh arm of the channel 156. As used herein, a "seventh DC electrode" and "the seventh DC electrode" are meant to include any number of DC electrodes disposed on the surface of the insulating substrate and interspersed within the seventh arm of the channel. Thus, for example, "the seventh DC electrode" includes one or more seventh DC electrodes. In some examples, the seventh DC electrode 158 can comprise a seventh plurality of DC electrodes. In some examples, the seventh DC electrode 158 comprises more than 1 DC electrodes (e.g., 2 or more, 3 or more, 4 or more, 5 or more, 6 or more, 7 or more, 8 or more, 9 or more, 10 or more, 11 or more, 12 or more, 13 or more, 14 or more, or 15 or more). In some examples, the seventh DC electrode comprises from 5 to 15 DC electrodes (e.g., from 6-14 DC electrodes, or from 8-14 DC electrodes). The number of DC electrodes comprising the seventh DC electrode can be selected, for example, in view of length of the seventh arm of the channel. In some examples, there can be 5-10 DC electrodes per 10 mm of the length of the arm of the channel.

The cross-section within the plane of the surface 104 of the insulating substrate 102 of the seventh DC electrode 158 can be of any shape (e.g., a circle, a quadrilateral, an ellipse, a triangle, a polygon, etc.). In some examples, the cross-section within the plane of the surface 104 of the insulating substrate 102 of the seventh DC electrode 158 is a quadrilateral (e.g., a rectangle, a parallelogram, or the like). In some examples, the cross-section within the plane of the surface 104 of the insulating substrate 102 of the seventh DC electrode 158 is substantially rectangular. The substantially rectangular cross-section of the seventh DC electrode 158 can, for example, have a length and a width. In some examples, the width of the substantially rectangular cross-section of the seventh DC electrode 158 can be 300 μm or more (e.g., 320 μm or more, 340 μm or more, 360 μm or more, 380 μm or more, 400 μm or more, 420 μm or more, 440 μm or more, 460 μm or more, 480 μm or more, 500 μm or more, 520 μm or more, 540 μm or more, 560 μm or more, or 580 μm or more). In some examples, the width of the substantially rectangular cross-section of the seventh DC electrode 158 can be 600 μm or less (e.g., 580 μm or less, 560 μm or less, 540 μm or less, 520 μm or less, 500 μm or less, 480 μm or less, 460 μm or less, 440 μm or less, 420 μm or less, 400 μm or less, 380 μm or less, 360 μm or less, 340 μm or less, or 320 μm or less). The width of the substantially rectangular cross-section of the seventh DC electrode 158 can range from any of the minimum values described above to any of the maximum values described above. For example, the width of the substantially rectangular cross-section of the seventh DC electrode 158 can be from 300 μm to 600 μm (e.g., from 300 μm to 440 μm, from 440 μm to 600 μm, from 300 μm to 400 μm, from 400 μm to 500 μm, from 500 μm to 600 μm, or from 360 μm to 400 μm).

The length of the substantially rectangular cross-section of the seventh DC electrode 158 can be 1-4 times the width. In some examples, the length of the substantially rectangular cross-section of the seventh DC electrode 158 can be 300 μm or more (e.g., 320 μm or more, 340 μm or more, 360 μm or more, 380 μm or more, 400 μm or more, 420 μm or more, 440 μm or more, 460 μm or more, 480 μm or more, 500 μm or more, 520 μm or more, 540 μm or more, 560 μm or more, 580 μm or more, 600 μm or more, 650 μm or more, 700 μm or more, 750 μm or more, 800 μm or more, 850 μm or more, 900 μm or more, 950 μm or more, 1000 μm or more, 1100 μm or more, 1200 μm or more, 1300 μm or more, 1400 μm or more, 1500 μm or more, 1750 μm or more, 2000 μm or more, or 2250 μm or more). In some examples, the length of the substantially rectangular cross-section of the seventh DC electrode 158 can be 2400 μm or less (e.g., 2250 μm or less, 2000 μm or less, 1750 μm or less, 1500 μm or less, 1400 μm or less, 1300 μm or less, 1200 μm or less, 1100 μm or less, 1000 μm or less, 950 μm or less, 900 μm or less, 850 μm or less, 800 μm or less, 750 μm or less, 700 μm or less, 650 μm or less, 600 μm or less, 580 μm or less, 560 μm or less, 540 μm or less, 520 μm or less, 500 μm or less, 480 μm or less, 460 μm or less, 440 μm or less, 420 μm or less, 400 μm or less, 380 μm or less, 360 μm or less, 340 μm or less, or 320 μm or less. The length of the substantially rectangular cross-section of the seventh DC electrode 158 can range from any of the minimum values described above to any of the maximum values described above. For example, the length of the substantially rectangular cross-section of the seventh DC electrode 158 can be from 300 μm to 2400 μm (e.g., from 300 μm to 1200 μm, from 1200 μm to 2400 μm, from 300 μm to 600 μm, from 600 μm to 900 μm, from 900 μm to 1200 μm, from 1200 μm to 1800 μm, from 1800 μm to 2400 μm, or from 300 μm to 1600 μm).

In some examples, each of the AC electrodes within the seventh pair of AC electrodes 154 is separated from the seventh DC electrode 158 by a thirteenth distance of 450 μm or more (e.g., 475 μm or more, 500 μm or more, 525 μm or more, 550 μm or more, 575 μm or more, 600 μm or more, 650 μm or more, 700 μm or more, 750 μm or more, 800 μm or more, 850 μm or more, 900 μm or more, 950 μm or more, 1000 μm or more, 1050 μm or more, 1100 μm or more, 1150 μm or more, 1200 μm or more, or 1250 μm or more), In some examples, each of the AC electrodes within the seventh pair of AC electrodes 154 is separated from the seventh DC electrode 158 by a thirteenth distance of 1270 µm or less (e.g., 1250 µm or less, 1200 µm or less, 1150 µm or less, 1100 µm or less, 1050 µm or less, 1000 µm or less, 950 µm or less, 900 µm or less, 850 µm or less, 800 µm or less, 750 µm or less, 700 µm or less, 650 µm or less, 600 µm or less, 575 µm or less, 550 µm or less, 525 µm or less, 500 µm or less, or 475 µm or less). The thirteenth distance can range from any of the minimum values described above to any of the maximum values described above. For example, each of the AC electrodes within the seventh pair of AC electrodes 154 is separated from the seventh DC electrode 158 by a thirteenth distance of from 450 µm to 1270 µm (e.g., from 450 µm to 850 µm, from 850 µm to 1270 µm, from 450 µm to 600 µm, from 600 µm 750 µm, from 750 µm to 900 µm, from 900 µm to 1050 µm, from 1050 µm to 1270 µm, from 475 µm to 1270 µm, or from 600 µm to 1270 µm). In some examples, the thirteenth distance is the same as the first distance, the third distance, the fifth distance, the seventh distance, the ninth distance, the eleventh distance, or a combination thereof.

In some examples, the seventh DC electrode 158 comprises a seventh plurality of DC electrodes and each DC electrode within the seventh plurality of DC electrodes is separated from its nearest neighboring DC electrode by a fourteenth distance of 150 µm or more (e.g., 170 µm or more, 190 µm or more, 210 µm or more, 230 µm or more, 250 µm or more, 275 µm or more, 300 µm or more, 325 µm or more, 350 µm or more, 375 µm or more, 400 µm or more, 425 µm or more, 450 µm or more, 475 µm or more, 500 µm or more, 550 µm or more, 600 µm or more, 650 µm or more, 700 µm or more, 750 µm or more, 800 µm or more, 900 µm or more, 1000 µm or more, 1100 µm or more, or 1200 µm or more). In some examples, the seventh DC electrode 158 comprises a seventh plurality of DC electrodes and each DC electrode within the seventh plurality of DC electrodes is separated from its nearest neighboring DC electrode by a fourteenth distance of 1270 µm or less (e.g., 1200 µm or less, 1100 µm or less, 1000 µm or less, 900 µm or less, 800 µm or less, 750 µm or less, 700 µm or less, 650 µm or less, 600 µm or less, 550 µm or less, 500 µm or less, 475 µm or less, 450 µm or less, 425 µm or less, 400 µm or less, 375 µm or less, 350 µm or less, 325 µm or less, 300 µm or less, 275 µm or less, 250 µm or less, 230 µm or less, 210 µm or less, 190 µm or less, or 170 µm or less). The fourteenth distance can range from any of the minimum values described above to any of the maximum values described above. For example, the seventh DC electrode 158 comprises a seventh plurality of DC electrodes and each DC electrode within the seventh plurality of DC electrodes is separated from its nearest neighboring DC electrode by a fourteenth distance of from 150 µm to 1270 µm (e.g., from 150 µm to 700 µm, from 700 µm to 1270 µm, from 150 µm to 300 µm, from 300 µm to 450 µm, from 450 µm to 600 µm, from 600 µm to 750 µm, from 750 µm to 900 µm, from 900 µm to 1050 µm, from 1050 µm to 1270 µm, from 190 µm to 1270 µm, or from 190 µm to 600 µm). In some examples, the fourteenth distance is from 190 µm to the thirteenth distance. In some examples, the thirteenth distance and the fourteenth distance are different. In some examples, the fourteenth distance is the same as the second distance, the fourth distance, the sixth distance, the eighth distance, the tenth distance, the twelfth distance, or a combination thereof.

The device 100 can further comprise a third junction 160, wherein the third arm of the channel 120, the sixth arm of the channel 150, and the seventh arm of the channel 156 intersect at a third junction 160. For example, the third arm of the channel 120 can split into the sixth arm of the channel 150 and the seventh arm of the channel 156 at the third junction 160.

In some examples, the sixth arm of the channel 150 further comprises a collection region 162, such that the sixth arm of the channel 150 extends from the third junction 160 to the collection region 162.

In some examples, the seventh arm of the channel 156 further comprises a collection region 164, such that seventh arm 156 of the channel extends from the third junction 160 to the collection region 164.

Figure 5:
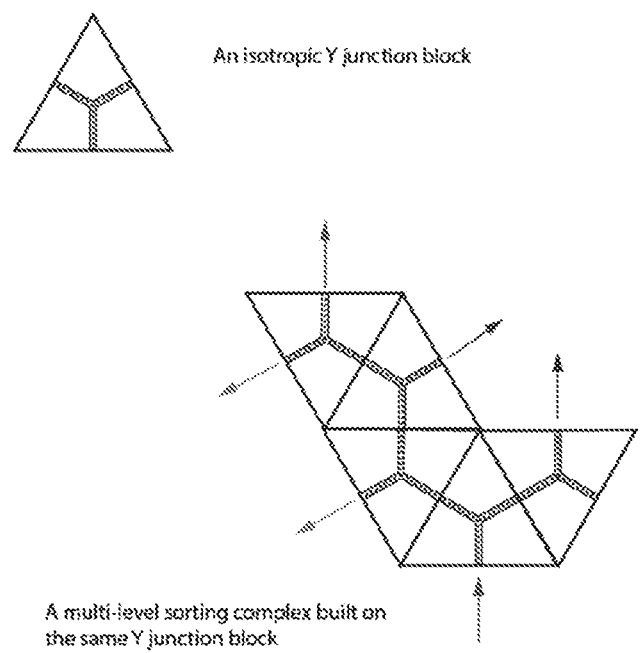
FIG. 5 is a schematic of an exemplary composite device as disclosed herein.

In some examples, the device 100 can comprise multiple devices 100 proximate one another to form a composite device. The devices can be aligned in the composite device such that the second arm of the channel of the first device aligns with the first arm of the channel of the second device, for example. The composite device can include any number of devices aligned in this manner to form a plurality of junctions. This alignment of multiple devices to form a composite device is shown schematically in FIG. 5.

The AC electrodes can comprise any suitable conductive material. For example, each of the AC electrodes comprising the first pair of AC electrodes 106, the second pair of AC electrodes 112, the third pair of AC electrodes 118, the fourth pair of AC electrodes 130, the fifth pair of AC electrodes 136, the sixth pair of AC electrodes 148, the seventh pair of AC electrodes 154, or a combination thereof comprises any metal suitable for lamination, for example copper, aluminum, silver, gold, or a combination thereof.

The DC electrodes can comprise any suitable conductive material. For example, the first DC electrode 110, the second DC electrode 116, the third DC electrode 122, the fourth DC electrode 134, the fifth DC electrode 140, the sixth DC electrode 152, the seventh DC electrode 158, or a combination thereof comprises any metal suitable for lamination, for example copper, aluminum, silver, gold, or a combination thereof.

The thickness (e.g., the dimension measured perpendicular to the surface of the insulating substrate) of each of the electrodes comprising the first pair of AC electrodes 106, the second pair of AC electrodes 112, the third pair of AC electrodes 118, the fourth pair of AC electrodes 130, the fifth pair of AC electrodes 136, the sixth pair of AC electrodes 148, the seventh pair of AC electrodes 154, the first DC electrode 110, the second DC electrode 116, the third DC electrode 122, the fourth DC electrode 134, the fifth DC electrode 140, the sixth DC electrode 152, the seventh DC electrode 158, or a combination thereof can be 36 µm or more (e.g., 40 µm or more, 45 µm or more, 50 µm or more, 55 µm or more, 60 µm or more, 65 µm or more, or 70 µm or more). In some examples, the thickness of each of the electrodes comprising the first pair of AC electrodes 106, the second pair of AC electrodes 112, the third pair of AC electrodes 118, the fourth pair of AC electrodes 130, the fifth pair of AC electrodes 136, the sixth pair of AC electrodes 148, the seventh pair of AC electrodes 154, the first DC electrode 110, the second DC electrode 116, the third DC electrode 122, the fourth DC electrode 134, the fifth DC electrode 140, the sixth DC electrode 152, the seventh DC electrode 158, or a combination thereof can be 72 µm or less (e.g., 70 µm or less, 65 µm or less, 60 µm or less, 55 µm or less, 50 µm or less, 45 µm or less, or 40 µm or less). The thickness of each of the electrodes comprising the first pair of AC electrodes 106, the second pair of AC electrodes 112, the third pair of AC electrodes 118, the fourth pair of AC electrodes 130, the fifth pair of AC electrodes 136, the sixth pair of AC electrodes 148, the seventh pair of AC electrodes 154, the first DC electrode 110, the second DC electrode 116, the third DC electrode 122, the fourth DC electrode 134, the fifth DC electrode 140, the sixth DC electrode 152, the seventh DC electrode 158, or a combination thereof can range from any of the minimum values described above to any of the maximum values described above. For example, the thickness of each of the electrodes comprising the first pair of AC electrodes 106, the second pair of AC electrodes 112, the third pair of AC electrodes 118, the fourth pair of AC electrodes 130, the fifth pair of AC electrodes 136, the sixth pair of AC electrodes 148, the seventh pair of AC electrodes 154, the first DC electrode 110, the second DC electrode 116, the third DC electrode 122, the fourth DC electrode 134, the fifth DC electrode 140, the sixth DC electrode 152, the seventh DC electrode 158, or a combination thereof can be from 36 µm to 72 µm (e.g., from 36 µm to 55 µm, from 55 µm to 72 µm, from 36 µm to 45 µm, from 45 µm to 55 µm, from 55 µm to 65 µm, from 65 µm to 72 µm, or from 40 µm to 70 µm).

In some examples, the device 100 can comprise a printed circuit board.

In some examples, the device 100 can further comprise a mask deposited on top of the first pair AC electrodes 106, the second pair of AC electrodes 112, the third pair of AC electrodes 118, the fourth pair of AC electrodes 130, the fifth pair of AC electrodes 136, the sixth pair of AC electrodes 148, the seventh pair of AC electrodes, the first DC electrode 110, the second DC electrode 116, the third DC electrode 122, the fourth DC electrode, the fifth DC electrode 140, the sixth DC electrode, the seventh DC electrode, or a combination thereof (e.g., such that the electrodes are encapsulated by the mask and the insulating substrate). The mask can comprise any suitable insulating material. In some examples, the mask can comprise a thin microscope glass cover or standard solder mask (lacquer like polymer) used by printed circuit board manufacturers.

Methods

Also disclosed herein are methods of sorting a particle based on a characteristic of the particle. In some examples, the methods can use any of the devices described herein.

In some examples, the methods of sorting a particle based on a characteristic of the particle can comprise providing a device comprising: an insulating substrate having a surface; a first pair of alternating current (AC) electrodes disposed on the surface of the insulating substrate, wherein each of the AC electrodes comprising the first pair of AC electrodes is spaced apart on the surface of the insulating substrate such that the first pair of AC electrodes define a first arm of a channel, and wherein each of AC electrodes comprising the first pair of AC electrodes is electrically connected to an AC voltage source; a first direct current (DC) electrode disposed on the surface of the insulating substrate and interspersed within the first arm of the channel, wherein the first DC electrode is electrically connected to a DC voltage source; a second pair of alternating current (AC) electrodes disposed on the surface of the insulating substrate, wherein each of the AC electrodes comprising the second pair of AC electrodes is spaced apart on the surface of the insulating substrate such that the second pair of AC electrodes define a second arm of a channel, and wherein each of AC electrodes comprising the second pair of AC electrodes is electrically connected to an AC voltage source; a direct current (DC) electrode disposed on the surface of the insulating substrate and interspersed within the second arm of the channel, wherein the second DC electrode is electrically connected to a DC voltage source; a third pair of alternating current (AC) electrodes disposed on the surface of the insulating substrate, wherein each of the AC electrodes comprising the third pair of AC electrodes is spaced apart on the surface of the insulating substrate such that the third pair of AC electrodes define a third arm of a channel, and wherein each of AC electrodes comprising the third pair of AC electrodes is electrically connected to an AC voltage source; and a third direct current (DC) electrode disposed on the surface of the insulating substrate and interspersed within the third arm of the channel, wherein the third DC electrode is electrically connected to a DC voltage source; wherein the first, second, and third arms of the channel intersect at a junction.

The methods can further comprise applying AC voltage to the first pair of AC electrodes, the second pair of AC electrodes, and the third pair of AC electrodes thereby generating an electromagnetic trapping field defining a confinement region, wherein the confinement region is proximate the channel and above the surface of the insulating substrate. In some examples, the AC voltage applied to the first pair of AC electrodes, the second pair of AC electrodes, the third pair of AC electrodes, or a combination thereof has a peak-to-peak voltage of 100 Volts (V) or more (e.g., 150 V or more, 200 V or more, 250 V or more, 300 V or more, 350 V or more, 400 V or more, 450 V or more, 500 V or more, 550 V or more, 600 V or more, 650 V or more, 700 V or more, 750 V or more, 800 V or more, 850 V or more, 900 V or more, 950 V or more, 1000 V or more, 1050 V or more, 1100 V or more, or 1150 V or more). In some examples, the AC voltage applied to the first pair of AC electrodes, the second pair of AC electrodes, the third pair of AC electrodes, or a combination thereof has a peak-to-peak voltage of 1200 V or less (e.g., 1150 V or less, 1100 V or less, 1050 V or less, 1000 V or less, 950 V or less, 900 V or less, 850 V or less, 800 V or less, 750 V or less, 700 V or less, 650 V or less, 600 V or less, 550 V or less, 500 V or less, 450 V or less, 400 V or less, 350 V or less, 300 V or less, 250 V or less, 200 V or less, or 150 V or less). The peak-to-peak voltage applied to the first pair of AC electrodes, the second pair of AC electrodes, the third pair of AC electrodes, or a combination thereof can range from any of the minimum values described above to any of the maximum values described above. For example, the AC voltage applied to the first pair of AC electrodes, the second pair of AC electrodes, the third pair of AC electrodes, or a combination thereof has a peak-to-peak voltage of from 100 V to 1200 V (e.g., from 100 V to 600 V, from 600 V to 1200 V, from 100 V to 400 V, from 400 V to 700 V, from 700 V to 1000 V, from 1000 V to 1200 V, or from 600 V to 1000 V). In some examples, the maximum AC voltage can be selected based on the first distance, the third distance, the fifth distance, or a combination thereof.

In some examples, the AC voltage applied to the first pair of AC electrodes, the second pair of AC electrodes, the third pair of AC electrodes, or a combination thereof has a frequency of 50 Hertz (Hz) or more (e.g., 75 Hz or more, 100 Hz or more, 125 Hz or more, 150 Hz or more, 175 Hz or more, 200 Hz or more, 225 Hz or more, 250 Hz or more, 275 Hz or more, 300 Hz or more, 325 Hz or more, 350 Hz or more, 375 Hz or more, 400 Hz or more, 450 Hz or more, 500 Hz or more, 550 Hz or more, 600 Hz or more, 700 Hz or more, 800 Hz or more, or 900 Hz or more). In some examples, the AC voltage applied to the first pair of AC electrodes, the second pair of AC electrodes, the third pair of AC electrodes, or a combination thereof has a frequency of 1000 Hz or less (e.g., 900 Hz or less, 800 Hz or less, 700 Hz or less, 600 Hz or less, 550 Hz or less, 500 Hz or less, 450

Hz or less, 400 Hz or less, 375 Hz or less, 350 Hz or less, 325 Hz or less, 300 Hz or less, 275 Hz or less, 250 Hz or less, 225 Hz or less, 200 Hz or less, 175 Hz or less, 150 Hz or less, 125 Hz or less, 100 Hz or less, or 75 Hz or less). The frequency of the AC voltage applied to the first pair of AC electrodes, the second pair of AC electrodes, the third pair of AC electrodes, or a combination thereof can range from any of the minimum values described above to any of the maximum values described above. For example, the AC voltage applied to the first pair of AC electrodes, the second pair of AC electrodes, the third pair of AC electrodes, or a combination thereof can have a frequency of from 50 Hz to 1000 Hz (e.g., from 50 Hz to 500 Hz, from 500 Hz to 1000 Hz, from 50 Hz to 200 Hz, from 200 Hz to 400 Hz, from 400 Hz to 600 Hz, from 600 Hz to 800 Hz, or from 800 Hz to 1000 Hz).

The confinement region can, for example, comprise a first arm, a second arm, and a third arm, and wherein the first, second, and third arms of the confinement region intersect at a junction. In some examples, an axis traversing the first arm of the channel and an axis traversing the first arm of the confinement region are substantially parallel. In some examples, an axis traversing the second arm of the channel and an axis traversing the second arm of the confinement region are substantially parallel. In some examples, an axis traversing the third arm of the channel and an axis traversing the third arm of the confinement region are substantially parallel. For example, the first arm of the confinement region splits into the second arm of the confinement region and the third arm of the confinement region at the junction of the confinement region. In some examples, the first arm of the confinement region can split into a plurality of additional arms at the junction. The first arm of the confinement region can further comprise a loading region and a detection region. In some examples, the detection region and the junction comprise substantially the same region of the first arm of the confinement region.

For example, the loading region is fluidly connected to the detection region, the detection region is fluidly connected to the junction of the confinement region, and the first arm of the confinement region is fluidly connected to the second arm of the confinement region and the third arm of the confinement region via the junction of the confinement region; such that the confinement region defines a path for fluid flow from the loading region to the detection region, from the detection region to the junction of the confinement region, and from the junction of the confinement region along the second arm of the confinement region and the third arm of the confinement region.

The methods further comprise injecting a droplet having a surface charge into the loading region, wherein the electromagnetic trapping field traps the droplet in the confinement region such that the droplet levitates above the surface of the insulating substrate. The confinement region can comprise a three dimensional area within the atmosphere above the surface of the insulating substrate where the balance of forces acting on the droplet substantially traps the droplet in the confinement region such that the droplet levitates above the surface of the insulating substrate. In some examples, the peak-to-peak voltage and frequency of the AC voltage applied to the first pair of AC electrodes, the second pair of AC electrodes, the third pair of AC electrodes, or a combination thereof to generate the electromagnetic trapping field can be selected based on the charge to mass ratio of the droplet.

The diameter of the droplet can, for example, be 20 μm or more (e.g., 25 μm or more, 30 μm or more, 35 μm or more, 40 μm or more, 45 μm or more, 50 μm or more, 55 μm or more, 60 μm or more, 65 μm or more, 70 μm or more, 75 μm or more, 80 μm or more, 85 μm or more, 90 μm or more, or 95 μm or more). In some examples, the diameter of the droplet can be 100 μm or less (e.g., 95 μm or less, 90 μm or less, 85 μm or less, 80 μm or less, 75 μm or less, 70 μm or less, 65 μm or less, 60 μm or less, 55 μm or less, 50 μm or less, 45 μm or less, 40 μm or less, 35 μm or less, 30 μm or less, or 25 μm or less). The diameter of the droplet can range from any of the minimum values described above to any of the maximum values described above. For example the diameter of the droplet can be from 20 μm to 100 μm (e.g., from 20 μm to 60 μm, from 60 μm to 100 μm, from 20 μm to 40 μm, from 40 μm to 60 μm, from 60 μm to 80 μm, from 80 μm to 100 μm, or from 30 μm to 90 μm).

The droplet can, for example, levitate above the surface of the insulating substrate at a distance of 300 μm or more (e.g., 350 μm or more, 400 μm or more, 450 μm or more, 500 μm or more, 550 μm or more, 600 μm or more, 650 μm or more, 700 μm or more, 750 μm or more, 800 μm or more, 850 μm or more, 900 μm or more, or 950 μm or more). In some examples, the droplet can levitate above the surface of the insulating substrate at a distance of 1000 μm or less (e.g., 950 μm or less, 900 μm or less, 850 μm or less, 800 μm or less, 750 μm or less, 700 μm or less, 650 μm or less, 600 μm or less, 550 μm or less, 500 μm or less, 450 μm or less, 400 μm or less, or 350 μm or less). The distance the droplet levitates above the surface of the insulating substrate can range from any of the minimum values described above to any of the maximum values described above. For example, the droplet can levitate above the surface of the insulating substrate at a distance of from 300 μm to 1000 μm (e.g., from 300 μm to 650 μm, from 650 μm to 1000 μm, from 300 μm to 500 μm, from 500 μm to 700 μm, from 700 μm to 1000 μm, or from 400 μm to 900 μm). In some examples, the droplet levitates above the surface of the insulating substrate is larger than the diameter of the droplet.

In some examples, the methods can further comprise forming the droplet having a surface charge. Forming the droplet having a surface charge can, for example, comprise ejecting a droplet from a droplet generating device and exposing the ejected droplet to an electric bias, thereby forming the droplet having a surface charge. In some examples, the electric bias can be 300 V or more (e.g., 350 V or more, 400 V or more, 450 V or more, 500 V or more, 550 V or more, 600 V or more, or 650 V or more). In some examples, the electric bias can be 700 V or less (e.g., 650 V or less, 600 V or less, 550 V or less, 500 V or less, 450 V or less, 400 V or less, or 350 V or less). The strength of the electric bias can range from any of the minimum values described above to any of the maximum values described above. For example, the electric bias can be from 300 V to 700 V (e.g., from 300 V to 500 V, from 500 V to 700 V, from 300 V to 400 V, from 400 V to 500 V, from 500 V to 600 V, from 600 V to 700 V, or from 350 V to 650V). The strength of the electric bias can, for example, be selected based on the diameter of the droplet. In some examples, the droplet generating device can further comprise a reservoir containing a volume of a liquid sample, and the droplet is ejected from the reservoir. The droplet generating device can, for example, comprise a piezoelectric droplet generating device.

The droplet can comprises a liquid sample comprising a particle. The liquid sample can, for example, further comprise an aqueous solvent. In some examples, the aqueous solvent can water and a cosolvent. Examples of cosolvents include, but are not limited to, alcohols (e.g., methanol, ethanol, n-butanol, isopropanol, n-propanol), carboxylic acids (e.g., acetic acid), chloroform, and combinations thereof.

In some examples, the length of the first, second, and/or third arms of the channel can be selected based on the lifetime of the droplet due to evaporation of the liquid sample, chemical reactions within the droplet, biological degradation of the particle, or a combination thereof. In some examples, humidity control can be used to minimize evaporation of the liquid sample from the droplet. In some examples, the lifetime of the droplet is related to the time that the particle remains suspended within the droplet. This can, for example, depend on the identity of the particle and the liquid sample.

The droplet can include, for example, 1 or more particles (e.g., 2 particles or more, 3 particles or more, 4 particles or more, 5 particles or more, 6 particles or more, 7 particles or more, 8 particles or more, 9 particles or more, 10 particles or more, 15 particles or more, 20 particles or more, 25 particles or more, 30 particles or more, 35 particles or more, 40 particles or more, 45 particles or more, 50 particles or more, 60 particles or more, 70 particles or more, 80 particles or more, 90 particles or more, 100 particles or more, 125 particles or more, 150 particles or more, 175 particles or more, 200 particles or more, 225 particles or more, 250 particles or more, 300 particles or more, 350 particles or more, 400 particles or more, 450 particles or more, 500 particles or more, 600 particles or more, 700 particles or more, 800 particles or more, or 900 particles or more). In some examples, the droplet can include 1000 particles or less (e.g., 900 particles or less, 800 particles or less, 700 particles or less, 600 particles or less, 500 particles or less, 450 particles or less, 400 particles or less, 350 particles or less, 300 particles or less, 250 particles or less, 225 particles or less, 200 particles or less, 175 particles or less, 150 particles or less, 125 particles or less, 100 particles or less, 90 particles or less, 80 particles or less, 70 particles or less, 60 particles or less, 50 particles or less, 45 particles or less, 40 particles or less, 35 particles or less, 30 particles or less, 25 particles or less, 20 particles or less, 15 particles or less, 10 particles or less, 9 particles or less, 8 particles or less, 7 particles or less, 6 particles or less, 5 particles or less, 4 particles or less, 3 particles or less, or 2 particles or less). The number of particles in the droplet can range from any of the minimum values described above to any of the maximum values described above. For example, the droplet can include from 1 to 1000 particles (e.g., from 1 particle to 500 particles, from 500 particles to 1000 particles, from 1 particle to 200 particles, from 200 particles to 400 particles, from 400 particles to 600 particles, from 600 particles to 800 particles, from 800 particles to 1000 particles, or from 1 particle to 100 particles). In some examples, the droplet comprises a single particle.

The particle can have an average particle size. "Average particle size" and "mean particle size" are used interchangeably herein, and generally refer to the statistical mean particle size of the particles in a population of particles. For example, the average particle size for a plurality of particles with a substantially spherical shape can comprise the average diameter of the plurality of particles. For a particle with a substantially spherical shape, the diameter of a particle can refer, for example, to the hydrodynamic diameter. As used herein, the hydrodynamic diameter of a particle can refer to the largest linear distance between two points on the surface of the particle. For an anisotropic particle, the average particle size can refer to, for example, the average maximum dimension of the particle (e.g., the length of a rod shaped particle, the diagonal of a cube shape particle, the bisector of a triangular shaped particle, etc.) For an anisotropic particle, the average particle size can refer to, for example, the hydrodynamic size of the particle. Mean particle size can be measured using methods known in the art, such as evaluation by scanning electron microscopy, transmission electron microscopy, and/or dynamic light scattering.

The particle can, for example, have an average particle size of 1 nm or more (e.g., 2 nm or more, 3 nm or more, 4 nm or more, 5 nm or more, 6 nm or more, 7 nm or more, 8 nm or more, 9 nm or more, 10 nm or more, 15 nm or more, 20 nm or more, 25 nm or more, 30 nm or more, 35 nm or more, 40 nm or more, 45 nm or more, 50 nm or more, 60 nm or more, 70 nm or more, 80 nm or more, 90 nm or more, 100 nm or more, 125 nm or more, 150 nm or more, 175 nm or more, 200 nm or more, 225 nm or more, 250 nm or more, 300 nm or more, 350 nm or more, 400 nm or more, 450 nm or more, 500 nm or more, 600 nm or more, 700 nm or more, 800 nm or more, 900 nm or more, 1 nm or more, 2 nm or more, 3 nm or more, 4 nm or more, 5 nm or more, 6 nm or more, 7 nm or more, 8 nm or more, or 9 nm or more). In some examples, the particle can have an average particle size of 10 nm or less (e.g., 9 nm or less, 8 nm or less, 7 nm or less, 6 nm or less, 5 nm or less, 4 nm or less, 3 nm or less, 2 nm or less, 1 nm or less, 900 nm or less, 800 nm or less, 700 nm or less, 600 nm or less, 500 nm or less, 450 nm or less, 400 nm or less, 350 nm or less, 300 nm or less, 250 nm or less, 225 nm or less, 200 nm or less, 175 nm or less, 150 nm or less, 125 nm or less, 100 nm or less, 90 nm or less, 80 nm or less, 70 nm or less, 60 nm or less, 50 nm or less, 45 nm or less, 40 nm or less, 35 nm or less, 30 nm or less, 25 nm or less, 20 nm or less, 15 nm or less, 10 nm or less, 9 nm or less, 8 nm or less, 7 nm or less, 6 nm or less, 5 nm or less, 4 nm or less, 3 nm or less, or 2 nm or less). The average particle size of the particle can range from any of the minimum values described above to any of the maximum values described above. For example, the average particle size can be from 1 nm to 10 nm (e.g., from 1 nm to 500 nm, from 500 nm to 10 nm, from 1 nm to 100 nm, from 100 nm to 1 nm, from 1 nm to 10 nm, or from 10 nm to 1 nm).

In some examples, the particle can comprise a polymer particle, a metal particle, a semiconductor particle, a biological cell, or a combination thereof. In some examples, the particle can comprise a polymer particle, such as a polystyrene particle.

In some examples, the particle can comprise a metal particle. The metal particle can, for example, comprise a metal selected from the group consisting of Be, Mg, Al, Ti, V, Cr, Mn, Fe, Co, Ni, Cu, Zn, Ga, Y, Zr, Nb, Mo, Tc, Ru, Rh, Pd, Ag, Cd, In, Sn, Hf, Ta, W, Re, Os, Ir, Pt, Au, Hg, Tl, Pb, Bi, La, Ce, Pr, Nd, Pm, Sm, Eu, Gd, Tb, Dy, Ho, Er, Tm, Yb, and combinations thereof. The metal particle can, in some examples, further comprise a capping layer comprising a plurality of ligands. Suitable ligands for capping layers for metal particles are known in the art.

In some examples, the particle can comprise a plasmonic particle, a quantum dot, or a combination thereof. The plasmonic particle can, for example, comprise a metal selected from the group consisting of Au, Ag, Pd, Cu, Cr, Al, and combinations thereof. The plasmonic particle can, in some examples, have an average particle size of 10 nm or more (e.g., 15 nm or more, 20 nm or more, 25 nm or more, 30 nm or more, 35 nm or more, 40 nm or more, 45 nm or more, 50 nm or more, 60 nm or more, 70 nm or more, 80 nm or more, or more, or 90 nm or more). In some examples, the plasmonic particle can have an average particle size of 100 nm or less (e.g., 90 nm or less, 80 nm or less, 70 nm or less, 60 nm or less, 50 nm or less, 45 nm or less, 40 nm or less, 35 nm or less, 30 nm or less, 25 nm or less, 20 nm or less, or 15 nm or less). The average particle size of the plasmonic particle can range from any of the minimum values described above to any of the maximum values described above. For example, the plasmonic particle can have an average particle size of from 10 nm to 100 nm (e.g., from 10 nm to 50 nm, from 50 nm to 100 nm, from 10 nm to 20 nm, from 20 nm to 40 nm, from 40 nm to 60 nm, from 60 nm to 80 nm, from 80 nm to 100 nm, or from 15 nm to 90 nm). The plasmonic particle can, in some examples, further comprise a capping layer comprising a plurality of ligands. Suitable ligands for capping layers for plasmonic particles are known in the art.

The quantum dot can, for example, comprise Si, C, GaAs, CdSe, CdTe, other semiconductor materials, or a combination thereof. In some examples, the quantum dot can have an average particle size of 1 nm or more (e.g., 2 nm or more, 3 nm or more, 4 nm or more, 5 nm or more, 6 nm or more, 7 nm or more, 8 nm or more, 9 nm or more, 10 nm or more, 15 nm or more, 20 nm or more, 25 nm or more, 30 nm or more, 35 nm or more, 40 nm or more, 45 nm or more, 50 nm or more, 60 nm or more, 70 nm or more, 80 nm or more, 90 nm or more, 100 nm or more, 125 nm or more, 150 nm or more, or 175 nm or more). In some examples, quantum dot can have an average particle size of 200 nm or less (e.g., 175 nm or less, 150 nm or less, 125 nm or less, 100 nm or less, 90 nm or less, 80 nm or less, 70 nm or less, 60 nm or less, 50 nm or less, 45 nm or less, 40 nm or less, 35 nm or less, 30 nm or less, 25 nm or less, 20 nm or less, 15 nm or less, 10 nm or less, 9 nm or less, 8 nm or less, 7 nm or less, 6 nm or less, 5 nm or less, 4 nm or less, 3 nm or less, or 2 nm or less). The average particle size of the quantum dot can range from any of the minimum values described above to any of the maximum values described above. For example, the quantum dot can have an average particle size of from 1 nm to 200 nm (e.g., from 1 nm to 100 nm, from 100 nm to 200 nm, from 1 nm to 20 nm, from 20 nm to 40 nm, from 40 nm to 60 nm, from 60 nm to 80 nm, from 80 nm to 100 nm, from 100 nm to 150 nm, from 150 nm to 200 nm, or from 5 nm to 175 nm). The quantum dot can, in some examples, further comprise a capping layer comprising a plurality of ligands. Suitable ligands for capping layers for quantum dots are known in the art.

In some examples, the particle can comprise a biological cell such as a fungal cell, a bacterial cell, a human cell, or a combination thereof. Examples of fungal cells include, but are not limited to yeast cells, *blastomyces dermatitides* cells, *coccidioides immitits* cells, *Cryptococcus neoformans* cells, *Histoplasma capsulatum* cells, and combinations thereof. Examples of bacterial cells include, but are not limited to, *bacillus* bacteria, *Brucella melitensis, Campylocavter jejuni, clostridium* bacteria (e.g., *Clostridium botulinum, Clostridium perfringens*), *Corynebacterium bovis, Enterobacter aerogenes, Escherichia coli, Klebsiella pneumoniae, Klebsiella oxytoca, Listeria monocytogenes, Mycobacterium tuberculosis, Mycoplasma* spp., *Pasteurella* spp., *Proteus* spp., *Pseudomonas aeruginosa, salmonella typhosa, Salmonella Enteritidis, Salmonella Typhimurium, Serratia marcescens, Shigella, Staphylococcus aureus, Staphylococcus epidermidis, Streptococcus agalactiae, Streptococcus pyogenes, Streptococcus uberis, Trueperella pyogenes, Vibrio cholerea, Vibrio parahaemolyticus, Vibria vulnificus, Yersinia enterocolitica*, and combinations thereof.

Examples of human cells include, but are not limited to, adipocytes, alveolar cells, amacrine cells, cancer cells, chondrocytes, corticotrophs, dendritic cells, endocrine cells (e.g., gonadotropic cells, thyrotropic cells), epithelial cells (e.g., cholangiocytes, cholecystocytes, endothelium, enterocytes, enteroendocrine cells, goblet cells, mesothelium, Paneth cells, parietyal cells, peg cells, trichocytes, tuft cells), fibroblasts (e.g., tendon cells), follicular cells, foveolar cells, glial cells (e.g., astrocyates, ependymal cells, microglia, oligodendrocytes, Schwann cells, satellite cells), granulocytes (e.g., neutrophils, eosinophils, basophils, mast cells), hair cells, hepatocytes, juxtaglomerular cells, keratinocytes, lymphocytes (e.g., T cells, B cells, natural killer cells), leukocytes (e.g., neutrophils, eosinophils, basophils, lymphocytes, monocytes, plasma cells), lymphoblast, Leydig cells, myocytes (e.g., cardiomycocytes), megakaryocyte, melanocytes, microfold cells, myeloblasts, neuroendocrine cells (e.g., chromaffin cells, enterochromaffin cells, magnocellular neurosecretory cells, parafollicular cells), neurons (e.g., mitral cells, parvocellular neurosecretory cells), osteoblasts, osteoclasts, osteocytes, parathyroid oxyphil cells, parathyroid chief cells, prolactin cell, podocytes, pericytes (e.g., extraglomerular mesangial cells, intraglomerular mesangial cells, hepatic stellate cells), photoreceptor cells (e.g., cone cells, rod cells, photosensitive retinal ganglion cells), peptic cells, phagocytes (e.g., histiocytes, Kupffer cells, alveolar macrophages, microglia), retina bipolar cells, retina horizontal cells, red blood cells (e.g., erythrocytes, normoblasts, megaloblasts, microcytes, cigar cells, reticulocytes, macroovalocytes), somatotrophic cells, stromal cells, thrombocytes, tumor cells, and combinations thereof.

In some examples, the particle can comprise a biological cell, such as a human cell comprising a cancel cell, a tumor cell, or a combination thereof.

Examples of cancer cells and/or tumor cells include, but are not limited to, cells indicative of bladder cancer, brain cancer, breast cancer, colorectal cancer, cervical cancer, gastrointestinal cancer, genitourinary cancer, head and neck cancer, lung cancer, ovarian cancer, pancreatic cancer, prostate cancer, renal cancer, skin cancer, and testicular cancer. Further examples include cells indicative of cancer and/or tumors of the anus, bile duct, bone, bone marrow, bowel (including colon and rectum), eye, gall bladder, kidney, mouth, larynx, esophagus, stomach, testis, cervix, mesothelioma, neuroendocrine, penis, skin, spinal cord, thyroid, vagina, vulva, uterus, liver, muscle, blood cells (including lymphocytes and other immune system cells).

In some examples, the biological cell is not damaged during the method. In some examples, the particle is not damaged during the method.

The methods can further comprise applying a first DC voltage to the first DC electrode to translocate the droplet from the loading region to the detection region. The first DC voltage can, for example, be −75 V or more (e.g., −70 V or more, −65 V or more, −60 V or more, −55 V or more, −50 V or more, −45 V or more, −40 V or more, −35 V or more, −30 V or more, −25 V or more, −20 V or more, −15 V or more, −10 V or more, −5 V or more, 0 V or more, 5 V or more, 10 V or more, 15 V or more, 20 V or more, 25 V or more, 30 V or more, 35 V or more, 40 V or more, 45 V or more, 50 V or more, 55 V or more, 60 V or more, 65 V or more, or 70 V or more). In some examples, the first DC voltage can be 75 V or less (e.g., 70 V or less, 65 V or less, 60 V or less, 55 V or less, 50 V or less, 45 V or less, 40 V or less, 35 V or less, 30 V or less, 25 V or less, 20 V or less, 15 V or less, 10 V or less, 5 V or less, 0 V or less, −5 V or less, −10 V or less, −15 V or less, −20 V or less, −25 V or less, −30 V or less, −35 V or less, −40 V or less, −45 V or less, −50 V or less, −55 V or less, −60 V or less, −65 V or less, or −70 V or less). The first DC voltage can range from any of the minimum values described above to any of the maximum values described above. For example, the first DC voltage can be from −75 V to 75 V (e.g., from −75 V to 0 V, from 0 V to 75 V, from −65 V to 65 V, from −55 V to 55 V, or from −45 V to 45 V).

In some examples, the droplet is translocated from the loading region to the detection region at a speed of 1 cm/s or more (e.g., 1.25 cm/s or more, 1.5 cm/s or more, 1.75 cm/s or more, 2 cm/s or more, 2.25 cm/s or more, 2.5 cm/s or more, 2.75 cm/s or more, 3 cm/s or more, 3.25 cm/s or more, 3.5 cm/s or more, 3.75 cm/s or more, 4 cm/s or more, 4.5 cm/s or more, 5 cm/s or more, 6 cm/s or more, 7 cm/s or more, 8 cm/s or more, 9 cm/s or more, 10 cm/s or more, 15 cm/s or more, 20 cm/s or more, 30 cm/s or more, 40 cm/s or more, 50 cm/s or more, 75 cm/s or more). In some examples, the droplet is translocated from the loading region to the detection region at a speed of 100 cm/s or less (e.g., 75 cm/s or less, 50 cm/s or less, 40 cm/s or less, 30 cm/s or less, 20 cm/s or less, 15 cm/s or less, 10 cm/s or less, 9 cm/s or less, 8 cm/s or less, 7 cm/s or less, 6 cm/s or less, 5 cm/s or less, 4.5 cm/s or less, 4 cm/s or less, 3.75 cm/s or less, 3.5 cm/s or less, 3.25 cm/s or less, 3 cm/s or less, 2.75 cm/s or less, 2.5 cm/s or less, 2.25 cm/s or less, 2 cm/s or less, 1.75 cm/s or less, 1.5 cm/s or less, or 1.25 cm/s or less). The speed at which the droplet is translocated from the loading region to the detection region can range from any of the minimum values described above to any of the maximum values described above. For example, the droplet can be translocated from the loading region to the detection region at a speed of from 1 cm/s to 100 cm/s (e.g., from 1 cm/s to 50 cm/s, from 50 cm/s to 100 cm/s, from 1 cm/s to 10 cm/s, from 10 cm/s to 20 cm/s, from 20 to 30 cm/s, from 30 to 40 cm/s, from 40 to 50 cm/s, from 1 cm/s to 4 cm/s, or from 1 cm/s to 20 cm/s). In some examples, the speed at which the droplet is translocated can be selected based on the strength of the first DC voltage applied to the first DC electrodes.

In some examples, the droplet is present in the detection region of the confinement region for an amount of time of 10 microseconds (p,$) or more (e.g., 20 μs or more, 30 μs or more, 40 μs or more, 50 μs or more, 75 μs or more, 100 μs or more, 125 μs or more, 150 μs or more, 200 μs or more, 250 μs or more, 300 μs or more, 350 μs or more, 400 μs or more, 500 μs or more, 600 μs or more, 700 μs or more, 800 μs or more, 900 μs or more, 1 millisecond (ms) or more, 5 ms or more, 10 ms or more, 20 ms or more, 30 ms or more, 40 ms or more, 50 ms or more, 75 ms or more, 100 ms or more, 125 ms or more, 150 ms or more, 200 ms or more, 250 ms or more, 300 ms or more, 350 ms or more, 400 ms or more, 500 ms or more, 600 ms or more, 700 ms or more, 800 ms or more, 900 ms or more, 1 second or more, 2 seconds or more, 3 seconds or more, 4 seconds or more, 5 seconds or more, 6 seconds or more, 7 seconds or more, 8 seconds or more, 9 seconds or more, 10 seconds or more, 15 seconds or more, 30 seconds or more, 45 seconds or more, or 1 minute or more). In some examples, the droplet is present in the detection region of the confinement region for an amount of time of 5 minutes or less (e.g., 1 minute or less, 45 seconds or less, 30 seconds or less, 15 seconds or less, 10 seconds or less, 9 seconds or less, 8 seconds or less, 7 seconds or less, 6 seconds or less, 5 seconds or less, 4 seconds or less, 3 seconds or less, 2 seconds or less, 1 second or less, 900 ms or less, 800 ms or less, 700 ms or less, 600 ms or less, 500 ms or less, 400 ms or less, 350 ms or less, 300 ms or less, 250 ms or less, 200 ms or less, 150 ms or less, 125 ms or less, 100 ms or less, 75 ms or less, 50 ms or less, 40 ms or less, 30 ms or less, 20 ms or less, 10 ms or less, 5 ms or less, 1 ms or less, 900 μs or less, 800 μs or less, 700 μs or less, 600 μs or less, 500 μs or less, 400 μs or less, 350 μs or less, 300 μs or less, 250 μs or less, 200 μs or less, 150 μs or less, 125 μs or less, 100 μs or less, 75 μs or less, 50 μs or less, 40 μs or less, 30 μs or less, or 20 μs or less). The amount of time the droplet is present in the detection region of the confinement region can range from any of the minimum values described above to any of the maximum values described above. For example, the droplet can be present in the detection region of the confinement region for an amount of time of from 10 μs to 5 minutes (e.g., from 10 μs to 100 μs, from 100 μs to 1 ms, from 1 ms to 10 ms, from 10 ms to 100 ms, from 100 ms to 1 second, from 1 second to 1 minutes, from 1 minute to 5 minutes, or from 100 ms to 10 seconds). In some examples, the time for which the droplet is present in the detection region can be selected based on the detection method, the droplet's lifetime, and the particle's lifetime within the droplet.

The methods can further comprise determining a characteristic of the particle in the droplet at the detection region. Determining a characteristic of the particle in the droplet can, for example, comprise capturing an electromagnetic signal from the particle and/or the droplet and analyzing the electromagnetic signal from the particle and/or the droplet to determine the characteristic of the particle. The electromagnetic signal can, in some examples, comprise an optical signal, a spectroscopic signal, or a combination thereof. Examples of electromagnetic signals include, but are not limited to, color, intensity, brightness, absorbance, scattering, fluorescence, frequency, wavelength, or a combination thereof.

The characteristic of the particle can, for example, comprises the presence, absence, or intensity of absorbance; the presence, absence, or intensity of scattering; the presence, absence, or intensity of fluorescence; the size of the particle; the number of particles in the droplet; or a combination thereof.

In some examples, the methods can further comprise conjugating the particle with a detectable moiety prior to injecting the droplet into the loading region. In certain examples, the characteristic of the particle can comprise the presence or absence of the detectable moiety. The methods can further comprise applying a second DC voltage to the first DC electrode to translocate the droplet from the detection region to the junction of the confinement region. In some examples, the second DC voltage is −75 V or more (e.g., −70 V or more, −65 V or more, −60 V or more, −55 V or more, −50 V or more, −45 V or more, −40 V or more, −35 V or more, −30 V or more, −25 V or more, −20 V or more, −15 V or more, −10 V or more, −5 V or more, 0 V or more, 5 V or more, 10 V or more, 15 V or more, 20 V or more, 25 V or more, 30 V or more, 35 V or more, 40 V or more, 45 V or more, 50 V or more, 55 V or more, 60 V or more, 65 V or more, or 70 V or more). In some examples, the second DC voltage is 75 V or less (e.g., 70 V or less, 65 V or less, 60 V or less, 55 V or less, 50 V or less, 45 V or less, 40 V or less, 35 V or less, 30 V or less, 25 V or less, 20 V or less, 15 V or less, 10 V or less, 5 V or less, 0 V or less, −5 V or less, −10 V or less, −15 V or less, −20 V or less, −25 V or less, −30 V or less, −35 V or less, −40 V or less, −45 V or less, −50 V or less, −55 V or less, −60 V or less, −65 V or less, or −70 V or less). The second DC voltage can range from any of the minimum values described above to any of the maximum values described above. For example, the second DC voltage can be from −75 V to 75 V (e.g., from −75 V to 0 V, from 0 V to 75 V, from −65 V to 65 V, from −55 V to 55 V, or from −45 V to 45 V).

In some examples, the droplet is translocated from the detection region to the junction of the confinement region at a speed of 1 cm/s or more (e.g., 1.25 cm/s or more, 1.5 cm/s or more, 1.75 cm/s or more, 2 cm/s or more, 2.25 cm/s or more, 2.5 cm/s or more, 2.75 cm/s or more, 3 cm/s or more, 3.25 cm/s or more, 3.5 cm/s or more, 3.75 cm/s or more, 4 cm/s or more, 4.5 cm/s or more, 5 cm/s or more, 6 cm/s or more, 7 cm/s or more, 8 cm/s or more, 9 cm/s or more, 10 cm/s or more, 15 cm/s or more, 20 cm/s or more, 30 cm/s or more, 40 cm/s or more, 50 cm/s or more, 75 cm/s or more). In some examples, the droplet is translocated from the detection region to the junction of the confinement region at a speed of 100 cm/s or less (e.g., 75 cm/s or less, 50 cm/s or less, 40 cm/s or less, 30 cm/s or less, 20 cm/s or less, 15 cm/s or less, 10 cm/s or less, 9 cm/s or less, 8 cm/s or less, 7 cm/s or less, 6 cm/s or less, 5 cm/s or less, 4.5 cm/s or less, 4 cm/s or less, 3.75 cm/s or less, 3.5 cm/s or less, 3.25 cm/s or less, 3 cm/s or less, 2.75 cm/s or less, 2.5 cm/s or less, 2.25 cm/s or less, 2 cm/s or less, 1.75 cm/s or less, 1.5 cm/s or less, or 1.25 cm/s or less). The speed at which droplet is translocated from the detection region to the junction of the confinement region can range from any of the minimum values described above to any of the maximum values described above. For example, the droplet can be translocated from the detection region to the junction of the confinement region at a speed of from 1 cm/s to 100 cm/s (e.g., from 1 cm/s to 50 cm/s, from 50 cm/s to 100 cm/s, from 1 cm/s to 10 cm/s, from 10 cm/s to 20 cm/s, from 20 to 30 cm/s, from 30 to 40 cm/s, from 40 to 50 cm/s, from 1 cm/s to 4 cm/s, or from 1 cm/s to 20 cm/s). In some examples, the speed at which the droplet is translocated can be selected based on the strength of the second DC voltage applied to the first DC electrode.

In some examples, the detection region of the confinement region and the junction of the confinement region comprise substantially the same region of the confinement region, and in those examples no second DC voltage is applied.

The methods can further comprise applying a third DC voltage to the first DC electrode, the second DC electrode, the third DC electrode, or a combination thereof to translocate the droplet from the junction of the confinement region to the second arm of the confinement region or the third arm of the confinement region based on the characteristic of the particle, thereby sorting the droplet (e.g., into the second or third arm of the confinement region) based on the characteristic of the particle.

The third DC voltage can, for example, be −75 V or more (e.g., −70 V or more, −65 V or more, −60 V or more, −55 V or more, −50 V or more, −45 V or more, −40 V or more, −35 V or more, −30 V or more, −25 V or more, −20 V or more, −15 V or more, −10 V or more, −5 V or more, 0 V or more, 5 V or more, 10 V or more, 15 V or more, 20 V or more, 25 V or more, 30 V or more, 35 V or more, 40 V or more, 45 V or more, 50 V or more, 55 V or more, 60 V or more, 65 V or more, or 70 V or more). In some examples, the third DC voltage can be 75 V or less (e.g., 70 V or less, 65 V or less, 60 V or less, 55 V or less, 50 V or less, 45 V or less, 40 V or less, 35 V or less, 30 V or less, 25 V or less, 20 V or less, 15 V or less, 10 V or less, 5 V or less, 0 V or less, −5 V or less, −10 V or less, −15 V or less, −20 V or less, −25 V or less, −30 V or less, −35 V or less, −40 V or less, −45 V or less, −50 V or less, −55 V or less, −60 V or less, −65 V or less, or −70 V or less). The third DC voltage can range from any of the minimum values described above to any of the maximum values described above. For example, the third DC can be from −75 V to 75 V (e.g., from −75 V to 0 V, from 0 V to 75 V, from −65 V to 65 V, from −55 V to 55 V, or from −45 V to 45 V).

In some examples, the droplet is translocated from the junction of the confinement region to the second or third arm of the confinement region at a speed of 1 cm/s or more (e.g., 1.25 cm/s or more, 1.5 cm/s or more, 1.75 cm/s or more, 2 cm/s or more, 2.25 cm/s or more, 2.5 cm/s or more, 2.75 cm/s or more, 3 cm/s or more, 3.25 cm/s or more, 3.5 cm/s or more, 3.75 cm/s or more, 4 cm/s or more, 4.5 cm/s or more, 5 cm/s or more, 6 cm/s or more, 7 cm/s or more, 8 cm/s or more, 9 cm/s or more, 10 cm/s or more, 15 cm/s or more, 20 cm/s or more, 30 cm/s or more, 40 cm/s or more, 50 cm/s or more, 75 cm/s or more). In some examples, the droplet is translocated from the junction of the confinement region to the second or third arm of the confinement region at a speed of 100 cm/s or less (e.g., 75 cm/s or less, 50 cm/s or less, 40 cm/s or less, 30 cm/s or less, 20 cm/s or less, 15 cm/s or less, 10 cm/s or less, 9 cm/s or less, 8 cm/s or less, 7 cm/s or less, 6 cm/s or less, 5 cm/s or less, 4.5 cm/s or less, 4 cm/s or less, 3.75 cm/s or less, 3.5 cm/s or less, 3.25 cm/s or less, 3 cm/s or less, 2.75 cm/s or less, 2.5 cm/s or less, 2.25 cm/s or less, 2 cm/s or less, 1.75 cm/s or less, 1.5 cm/s or less, or 1.25 cm/s or less). The speed at which the droplet is translocated from the junction of the confinement region to the second or third arm of the confinement region can range from any of the minimum values described above to any of the maximum values described above. For example, the droplet can be translocated from the junction of the confinement region to the second or third arm of the confinement region at a speed of from 1 cm/s to 100 cm/s (e.g., from 1 cm/s to 50 cm/s, from 50 cm/s to 100 cm/s, from 1 cm/s to 10 cm/s, from 10 cm/s to 20 cm/s, from 20 to 30 cm/s, from 30 to 40 cm/s, from 40 to 50 cm/s, from 1 cm/s to 4 cm/s, or from 1 cm/s to 20 cm/s). In some examples, the speed at which the droplet is translocated can be selected based on the strength of the third DC voltage applied to the first DC electrode, second DC electrode, third DC electrode, or a combination thereof.

In some examples, the droplet is sorted into the second arm of the confinement region. In some examples, the second arm of the channel further comprises a collection region such that the second arm of the confinement region further comprises a collection region (e.g., such that the second arm of the confinement region can extend from the first junction of the confinement region to the collection region). In some examples, the method can further comprise applying a fourth DC voltage to the second DC electrode to translocate the droplet to the collection region of the second arm of the confinement region. In some examples, the methods can further comprise collecting the droplet by turning off the AC voltage to at least the second pair of AC electrodes such that the droplet falls into the collection region of the second arm of the channel.

In some examples, the droplet is sorted into the third arm of the confinement region. In some examples, the third arm of the channel further comprises a collection region such that third arm of the confinement region further comprises a collection region (e.g., such that the third arm of the confinement region extends from the first junction to the collection region). The methods can, for example, further comprise applying a fourth DC voltage to the third DC electrode to translocate the droplet to the collection region of the third arm of the confinement region. In some examples, the methods can further comprise collecting the droplet by turning off the AC voltage to at least the third pair of AC electrodes such that the droplet falls into the collection region of the third arm of the channel.

In some examples, the fourth DC voltage can be −75 V or more (e.g., −70 V or more, −65 V or more, −60 V or more, −55 V or more, −50 V or more, −45 V or more, −40 V or more, −35 V or more, −30 V or more, −25 V or more, −20 V or more, −15 V or more, −10 V or more, −5 V or more, 0 V or more, 5 V or more, 10 V or more, 15 V or more, 20 V or more, 25 V or more, 30 V or more, 35 V or more, 40 V or more, 45 V or more, 50 V or more, 55 V or more, 60 V or more, 65 V or more, or 70 V or more). In some examples, the fourth DC voltage can be 75 V or less (e.g., 70 V or less, 65 V or less, 60 V or less, 55 V or less, 50 V or less, 45 V or less, 40 V or less, 35 V or less, 30 V or less, 25 V or less, 20 V or less, 15 V or less, 10 V or less, 5 V or less, 0 V or less, −5 V or less, −10 V or less, −15 V or less, −20 V or less, −25 V or less, −30 V or less, −35 V or less, −40 V or less, −45 V or less, −50 V or less, −55 V or less, −60 V or less, −65 V or less, or −70 V or less). The fourth DC voltage can range from any of the minimum values described above to any of the maximum values described above. For example, the fourth DC voltage can be from −75 V to 75 V (e.g., from −75 V to 0 V, from 0 V to 75 V, from −65 V to 65 V, from −55 V to 55 V, or from −45 V to 45 V).

In some examples, the droplet is translocated within the second or third arm of the confinement region to the collection region at a speed of 1 cm/s or more (e.g., 1.25 cm/s or more, 1.5 cm/s or more, 1.75 cm/s or more, 2 cm/s or more, 2.25 cm/s or more, 2.5 cm/s or more, 2.75 cm/s or more, 3 cm/s or more, 3.25 cm/s or more, 3.5 cm/s or more, 3.75 cm/s or more, 4 cm/s or more, 4.5 cm/s or more, 5 cm/s or more, 6 cm/s or more, 7 cm/s or more, 8 cm/s or more, 9 cm/s or more, 10 cm/s or more, 15 cm/s or more, 20 cm/s or more, 30 cm/s or more, 40 cm/s or more, 50 cm/s or more, 75 cm/s or more). In some examples, the droplet is translocated within the second or third arm of the confinement region to the collection region at a speed of 100 cm/s or less (e.g., 75 cm/s or less, 50 cm/s or less, 40 cm/s or less, 30 cm/s or less, 20 cm/s or less, 15 cm/s or less, 10 cm/s or less, 9 cm/s or less, 8 cm/s or less, 7 cm/s or less, 6 cm/s or less, 5 cm/s or less, 4.5 cm/s or less, 4 cm/s or less, 3.75 cm/s or less, 3.5 cm/s or less, 3.25 cm/s or less, 3 cm/s or less, 2.75 cm/s or less, 2.5 cm/s or less, 2.25 cm/s or less, 2 cm/s or less, 1.75 cm/s or less, 1.5 cm/s or less, or 1.25 cm/s or less). The speed at which the droplet is translocated within the second or third arm of the confinement region to the collection region can range from any of the minimum values described above to any of the maximum values described above. For example, the droplet can be translocated within the second or third arm of the confinement region to the collection region at a speed of from 1 cm/s to 100 cm/s (e.g., from 1 cm/s to 50 cm/s, from 50 cm/s to 100 cm/s, from 1 cm/s to 10 cm/s, from 10 cm/s to 20 cm/s, from 20 to 30 cm/s, from 30 to 40 cm/s, from 40 to 50 cm/s, from 1 cm/s to 4 cm/s, or from 1 cm/s to 20 cm/s). In some examples, the speed at which the droplet is translocated can be selected based on the strength of the fourth DC voltage applied to the second DC electrode or third DC electrode.

In some examples, the device can further comprise a plurality of additional pairs of AC electrodes disposed on the surface of the insulating substrate, wherein each of the AC electrodes comprising the plurality of additional pairs of AC electrodes is spaced apart on the surface of the insulating substrate such that the plurality of additional pairs of AC electrodes define a plurality of additional arms of a channel, wherein the plurality of additional arms of the channel can each intersect with the second arm of the channel at a second junction, such that the second arm of the channel branches into a plurality of additional channels at the second junction.

In certain examples, the device can further comprise a plurality of additional direct current (DC) electrode disposed on the surface of the insulating substrate and interspersed within the each of the plurality of additional arms of the channel. In certain examples, the methods can further comprise applying AC voltage to the plurality of additional pairs of AC electrodes, such that the confinement region further comprises a plurality of additional arms, wherein the wherein the plurality of additional arms of the confinement region can each intersect with the second arm of the confinement at a second junction, such that the second arm of the confinement region branches into a plurality of additional arms at the second junction In some examples, the device can further comprise a plurality of additional pairs of AC electrodes disposed on the surface of the insulating substrate, wherein each of the AC electrodes comprising the plurality of additional pairs of AC electrodes is spaced apart on the surface of the insulating substrate such that the plurality of additional pairs of AC electrodes define a plurality of additional arms of a channel, wherein the plurality of additional arms of the channel can each intersect with the third arm of the channel at a third junction, such that the third arm of the channel branches into a plurality of additional channels at the third junction. In certain examples, the device can further comprise a plurality of additional direct current (DC) electrode disposed on the surface of the insulating substrate and interspersed within the each of the plurality of additional arms of the channel. In certain examples, the methods can further comprise applying AC voltage to the plurality of additional pairs of AC electrodes, such that the confinement region further comprises a plurality of additional arms, wherein the wherein the plurality of additional arms of the confinement region can each intersect with the third arm of the confinement at a third junction, such that the third arm of the confinement region branches into a plurality of additional arms at the third junction In some examples, the second arm of the confinement region further comprises second detection region. In some examples, the device further comprises: a fourth pair of alternating current (AC) electrodes disposed on the surface of the insulating substrate, wherein each of the AC electrodes comprising the fourth pair of AC electrodes is spaced apart on the surface of the insulating substrate such that the fourth pair of AC electrodes define a fourth arm of a channel, and wherein each of AC electrodes comprising the fourth pair of AC electrodes is electrically connected to an AC voltage source; a fourth direct current (DC) electrode disposed on the surface of the insulating substrate and interspersed within the fourth arm of the channel, wherein the fourth DC electrode is electrically connected to a DC voltage source; a fifth pair of alternating current (AC) electrodes disposed on the surface of the insulating substrate, wherein each of the AC electrodes comprising the fifth pair of AC electrodes is spaced apart on the surface of the insulating substrate such that the fifth pair of AC electrodes define a fifth arm of a channel, and wherein each of AC electrodes comprising the fifth pair of AC electrodes is electrically connected to an AC voltage source; and a fifth direct current (DC) electrode disposed on the surface of the insulating substrate and interspersed within the fifth arm of the channel, wherein the fifth DC electrode is electrically connected to a DC voltage source; wherein the second arm of the channel, the fourth arm of the channel, and the fifth arm of the channel intersect at a second junction.

In some examples, the methods can further comprise applying AC voltage to the fourth pair of AC electrodes and the fifth pair of AC electrodes, such that the confinement region further comprises a fourth arm and a fifth arm, wherein the second, fourth, and fifth arms of the confinement region intersect at a second junction. In some examples, the AC voltage applied to the fourth pair of AC electrodes and/or the fifth pair of AC electrodes has a peak-to-peak voltage of 100 Volts (V) or more (e.g., 150 V or more, 200 V or more, 250 V or more, 300 V or more, 350 V or more, 400 V or more, 450 V or more, 500 V or more, 550 V or more, 600 V or more, 650 V or more, 700 V or more, 750 V or more, 800 V or more, 850 V or more, 900 V or more, 950 V or more, 1000 V or more, 1050 V or more, 1100 V or more, or 1150 V or more). In some examples, the AC voltage applied to the fourth pair of AC electrodes and/or the fifth pair of AC electrodes has a peak-to-peak voltage of 1200 V or less (e.g., 1150 V or less, 1100 V or less, 1050 V or less, 1000 V or less, 950 V or less, 900 V or less, 850 V or less, 800 V or less, 750 V or less, 700 V or less, 650 V or less, 600 V or less, 550 V or less, 500 V or less, 450 V or less, 400 V or less, 350 V or less, 300 V or less, 250 V or less, 200 V or less, or 150 V or less). The peak-to-peak voltage of the AC voltage applied to the fourth pair of AC electrodes and/or the fifth pair of AC electrodes can range from any of the minimum values described above to any of the maximum values described above. For example, the AC voltage applied to the fourth pair of AC electrodes and/or the fifth pair of AC electrodes has a peak-to-peak voltage of from 100 V to 1200 V (e.g., from 100 V to 600 V, from 600 V to 1200 V, from 100 V to 400 V, from 400 V to 700 V, from 700 V to 1000 V, from 1000 V to 1200 V, or from 600 V to 1000 V). In some examples, the maximum AC voltage can be selected based on the seventh distance and/or the ninth distance. In some examples, the peak-to-peak voltage of the AC voltage applied to the fourth pair of AC electrodes and/or the fifth pair of AC electrodes is the same as the peak-to-peak voltage applied to the first pair of AC electrodes, the second pair of AC electrodes, the third pair of AC electrodes, or a combination thereof.

In some examples, the AC voltage applied to the fourth pair of AC electrodes and/or the fifth pair of AC electrodes has a frequency of 50 Hertz (Hz) or more (e.g., 75 Hz or more, 100 Hz or more, 125 Hz or more, 150 Hz or more, 175 Hz or more, 200 Hz or more, 225 Hz or more, 250 Hz or more, 275 Hz or more, 300 Hz or more, 325 Hz or more, 350 Hz or more, 375 Hz or more, 400 Hz or more, 450 Hz or more, 500 Hz or more, 550 Hz or more, 600 Hz or more, 700 Hz or more, 800 Hz or more, or 900 Hz or more). In some examples, the AC voltage applied to the fourth pair of AC electrodes and/or the fifth pair of AC electrodes has a frequency of 1000 Hz or less (e.g., 900 Hz or less, 800 Hz or less, 700 Hz or less, 600 Hz or less, 550 Hz or less, 500 Hz or less, 450 Hz or less, 400 Hz or less, 375 Hz or less, 350 Hz or less, 325 Hz or less, 300 Hz or less, 275 Hz or less, 250 Hz or less, 225 Hz or less, 200 Hz or less, 175 Hz or less, 150 Hz or less, 125 Hz or less, 100 Hz or less, or 75 Hz or less). The frequency of the AC voltage applied to the fourth pair of AC electrodes and/or the fifth pair of AC electrodes can range from any of the minimum values described above to any of the maximum values described above. For example, the AC voltage applied to the fourth pair of AC electrodes and/or the fifth pair of AC electrodes has a frequency of from 50 Hz to 1000 Hz (e.g., from 50 Hz to 500 Hz, from 500 Hz to 1000 Hz, from 50 Hz to 200 Hz, from 200 Hz to 400 Hz, from 400 Hz to 600 Hz, from 600 Hz to 800 Hz, or from 800 Hz to 1000 Hz), In some examples, the frequency of the AC voltage applied to the fourth pair of AC electrodes and/or the fifth pair of AC electrodes is the same as the frequency applied to the first pair of AC electrodes, the second pair of AC electrodes, the third pair of AC electrodes, or a combination thereof.

The confinement region can, for example, further comprise a fourth arm and a fifth arm, wherein the second, fourth, and fifth arms of the confinement region intersect at a second junction. In some examples, an axis traversing the fourth arm of the channel and an axis traversing the fourth arm of the confinement region are substantially parallel. In some examples, an axis traversing the fifth arm of the channel and an axis traversing the fifth arm of the confinement region are substantially parallel. For example, the second arm of the confinement region can split into the fourth and fifth arms of the confinement region at the second junction. In some examples, the second arm of the confinement region can split into a plurality of additional arms at the second junction.

In some examples, the first junction of the confinement region is fluidly connected to the second junction of the confinement region via the second arm of the confinement region, such that the second detection region is fluidly connected to the second junction of the confinement region; and wherein the second arm of the confinement region is fluidly connected to the fourth arm of the confinement region and the fifth arm of the confinement region via the second junction of the confinement region, such that the confinement region defines a path for fluid flow from the junction of the confinement region to the second detection region, from the second detection region to the second junction of the confinement region, and from the second junction of the confinement region along the fourth arm of the confinement region and the fifth arm of the confinement region.

In some examples, the droplet is in the second arm of the confinement region; and the method further comprises applying a fourth DC voltage to the second DC electrode to translocate the droplet to the second detection region In some examples, the fourth DC voltage can be −75 V or more (e.g., −70 V or more, −65 V or more, −60 V or more, −55 V or more, −50 V or more, −45 V or more, −40 V or more, −35 V or more, −30 V or more, −25 V or more, −20 V or more, −15 V or more, −10 V or more, −5 V or more, 0 V or more, 5 V or more, 10 V or more, 15 V or more, 20 V or more, 25 V or more, 30 V or more, 35 V or more, 40 V or more, 45 V or more, 50 V or more, 55 V or more, 60 V or more, 65 V or more, or 70 V or more). In some examples, the fourth DC voltage can be 75 V or less (e.g., 70 V or less, 65 V or less, 60 V or less, 55 V or less, 50 V or less, 45 V or less, 40 V or less, 35 V or less, 30 V or less, 25 V or less, 20 V or less, 15 V or less, 10 V or less, 5 V or less, 0 V or less, −5 V or less, −10 V or less, −15 V or less, −20 V or less, −25 V or less, −30 V or less, −35 V or less, −40 V or less, −45 V or less, −50 V or less, −55 V or less, −60 V or less, −65 V or less, or −70 V or less). The fourth DC voltage can range from any of the minimum values described above to any of the maximum values described above. For example, the fourth DC voltage can be from −75 V to 75 V (e.g., from −75 V to 0 V, from 0 V to 75 V, from −65 V to 65 V, from −55 V to 55 V, or from −45 V to 45 V).

In some examples, the droplet is translocated within the second arm of the confinement region to the second detection region at a speed of 1 cm/s or more (e.g., 1.25 cm/s or more, 1.5 cm/s or more, 1.75 cm/s or more, 2 cm/s or more, 2.25 cm/s or more, 2.5 cm/s or more, 2.75 cm/s or more, 3 cm/s or more, 3.25 cm/s or more, 3.5 cm/s or more, 3.75 cm/s or more, 4 cm/s or more, 4.5 cm/s or more, 5 cm/s or more, 6 cm/s or more, 7 cm/s or more, 8 cm/s or more, 9 cm/s or more, 10 cm/s or more, 15 cm/s or more, 20 cm/s or more, 30 cm/s or more, 40 cm/s or more, 50 cm/s or more, 75 cm/s or more). In some examples, the droplet is translocated within the second arm of the confinement region to the second detection region at a speed of 100 cm/s or less (e.g., 75 cm/s or less, 50 cm/s or less, 40 cm/s or less, 30 cm/s or less, 20 cm/s or less, 15 cm/s or less, 10 cm/s or less, 9 cm/s or less, 8 cm/s or less, 7 cm/s or less, 6 cm/s or less, 5 cm/s or less, 4.5 cm/s or less, 4 cm/s or less, 3.75 cm/s or less, 3.5 cm/s or less, 3.25 cm/s or less, 3 cm/s or less, 2.75 cm/s or less, 2.5 cm/s or less, 2.25 cm/s or less, 2 cm/s or less, 1.75 cm/s or less, 1.5 cm/s or less, or 1.25 cm/s or less). The speed at which the droplet is translocated within the second arm of the confinement region to the second detection region can range from any of the minimum values described above to any of the maximum values described above. For example, the droplet can be translocated within the second arm of the confinement region to the second detection region at a speed of from 1 cm/s to 100 cm/s (e.g., from 1 cm/s to 50 cm/s, from 50 cm/s to 100 cm/s, from 1 cm/s to 10 cm/s, from 10 cm/s to 20 cm/s, from 20 to 30 cm/s, from 30 to 40 cm/s, from 40 to 50 cm/s, from 1 cm/s to 4 cm/s, or from 1 cm/s to 20 cm/s). In some examples, the speed at which the droplet is translocated can be selected based on the strength of the fourth DC voltage applied to the second DC electrode.

The methods can, in some examples, further comprise determining a second characteristic of the particle in the droplet at the second detection region. The second characteristic of the particle can be different than the first characteristic of the particle. Determining a second characteristic of the particle in the droplet can, for example, comprise capturing an electromagnetic signal from the particle and/or the droplet and analyzing the electromagnetic signal from the particle and/or the droplet to determine the second characteristic of the particle. The electromagnetic signal can, in some examples, comprise an optical signal, a spectroscopic signal, or a combination thereof. Examples of electromagnetic signals include, but are not limited to, color, intensity, brightness, absorbance, scattering, fluorescence, frequency, wavelength, or a combination thereof. The second characteristic of the particle can, for example, comprises the presence, absence, or intensity of absorbance; the presence, absence, or intensity of scattering; the presence, absence, or intensity of fluorescence; the size of the particle; the number of particles in the droplet; or a combination thereof.

In some examples, the droplet is present in the second detection region of the confinement region for an amount of time of 10 microseconds (µs) or more (e.g., 20 µs or more, 30 µs or more, 40 µs or more, 50 µs or more, 75 µs or more, 100 µs or more, 125 µs or more, 150 µs or more, 200 µs or more, 250 µs or more, 300 µs or more, 350 µs or more, 400 µs or more, 500 µs or more, 600 µs or more, 700 µs or more, 800 µs or more, 900 µs or more, 1 millisecond (ms) or more, 5 ms or more, 10 ms or more, 20 ms or more, 30 ms or more, 40 ms or more, 50 ms or more, 75 ms or more, 100 ms or more, 125 ms or more, 150 ms or more, 200 ms or more, 250 ms or more, 300 ms or more, 350 ms or more, 400 ms or more, 500 ms or more, 600 ms or more, 700 ms or more, 800 ms or more, 900 ms or more, 1 second or more, 2 seconds or more, 3 seconds or more, 4 seconds or more, 5 seconds or more, 6 seconds or more, 7 seconds or more, 8 seconds or more, 9 seconds or more, 10 seconds or more, 15 seconds or more, 30 seconds or more, 45 seconds or more, or 1 minute or more). In some examples, the droplet is present in the second detection region of the confinement region for an amount of time of 5 minutes or less (e.g., 1 minute or less, 45 seconds or less, 30 seconds or less, 15 seconds or less, 10 seconds or less, 9 seconds or less, 8 seconds or less, 7 seconds or less, 6 seconds or less, 5 seconds or less, 4 seconds or less, 3 seconds or less, 2 seconds or less, 1 second or less, 900 ms or less, 800 ms or less, 700 ms or less, 600 ms or less, 500 ms or less, 400 ms or less, 350 ms or less, 300 ms or less, 250 ms or less, 200 ms or less, 150 ms or less, 125 ms or less, 100 ms or less, 75 ms or less, 50 ms or less, 40 ms or less, 30 ms or less, 20 ms or less, 10 ms or less, 5 ms or less, 1 ms or less, 900 µs or less, 800 µs or less, 700 µs or less, 600 µs or less, 500 µs or less, 400 µs or less, 350 µs or less, 300 µs or less, 250 µs or less, 200 µs or less, 150 µs or less, 125 µs or less, 100 µs or less, 75 µs or less, 50 µs or less, 40 µs or less, 30 µs or less, or 20 µs or less). The amount of time the droplet is present in the second detection region of the confinement region can range from any of the minimum values described above to any of the maximum values described above. For example, the droplet can be present in the second detection region of the confinement region for an amount of time of from 10 µs to 5 minutes (e.g., from 10 µs to 100 µs, from 100 µs to 1 ms, from 1 ms to 10 ms, from 10 ms to 100 ms, from 100 ms to 1 second, from 1 second to 1 minutes, from 1 minute to 5 minutes, or from 100 ms to 10 seconds). In some examples, the time for which the droplet is present in the second detection region can be selected based on the detection method, the droplet's lifetime, and the particle's lifetime within the droplet.

The methods can further comprise, for example, applying a fifth DC voltage to the second DC electrode to translocate the droplet from the second detection region to the second junction of the confinement region. In some examples, the fifth DC voltage can be −75 V or more (e.g., −70 V or more, −65 V or more, −60 V or more, −55 V or more, −50 V or more, −45 V or more, −40 V or more, −35 V or more, −30 V or more, −25 V or more, −20 V or more, −15 V or more, −10 V or more, −5 V or more, 0 V or more, 5 V or more, 10 V or more, 15 V or more, 20 V or more, 25 V or more, 30 V or more, 35 V or more, 40 V or more, 45 V or more, 50 V or more, 55 V or more, 60 V or more, 65 V or more, or 70 V or more). In some examples, the fifth DC voltage can be 75 V or less (e.g., 70 V or less, 65 V or less, 60 V or less, 55 V or less, 50 V or less, 45 V or less, 40 V or less, 35 V or less, 30 V or less, 25 V or less, 20 V or less, 15 V or less, 10 V or less, 5 V or less, 0 V or less, −5 V or less, −10 V or less, −15 V or less, −20 V or less, −25 V or less, −30 V or less, −35 V or less, −40 V or less, −45 V or less, −50 V or less, −55 V or less, −60 V or less, −65 V or less, or −70 V or less). The fifth DC voltage can range from any of the minimum values described above to any of the maximum values described above. For example, the fifth DC voltage can be from −75 V to 75 V (e.g., from −75 V to 0 V, from 0 V to 75 V, from −65 V to 65 V, from −55 V to 55 V, or is from −45 V to 45 V).

In some examples, the droplet is translocated from the second detection region to the second junction of the confinement region at a speed of 1 cm/s or more (e.g., 1.25 cm/s or more, 1.5 cm/s or more, 1.75 cm/s or more, 2 cm/s or more, 2.25 cm/s or more, 2.5 cm/s or more, 2.75 cm/s or more, 3 cm/s or more, 3.25 cm/s or more, 3.5 cm/s or more, 3.75 cm/s or more, 4 cm/s or more, 4.5 cm/s or more, 5 cm/s or more, 6 cm/s or more, 7 cm/s or more, 8 cm/s or more, 9 cm/s or more, 10 cm/s or more, 15 cm/s or more, 20 cm/s or more, 30 cm/s or more, 40 cm/s or more, 50 cm/s or more, 75 cm/s or more). In some examples, the droplet is translocated from the second detection region to the second junction of the confinement region at a speed of 100 cm/s or less (e.g., 75 cm/s or less, 50 cm/s or less, 40 cm/s or less, 30 cm/s or less, 20 cm/s or less, 15 cm/s or less, 10 cm/s or less, 9 cm/s or less, 8 cm/s or less, 7 cm/s or less, 6 cm/s or less, 5 cm/s or less, 4.5 cm/s or less, 4 cm/s or less, 3.75 cm/s or less, 3.5 cm/s or less, 3.25 cm/s or less, 3 cm/s or less, 2.75 cm/s or less, 2.5 cm/s or less, 2.25 cm/s or less, 2 cm/s or less, 1.75 cm/s or less, 1.5 cm/s or less, or 1.25 cm/s or less). The speed at which the droplet is translocated from the second detection region to the second junction of the confinement region can range from any of the minimum values described above to any of the maximum values described above. For example, the droplet can be translocated from the second detection region to the second junction of the confinement region at a speed of from 1 cm/s to 100 cm/s (e.g., from 1 cm/s to 50 cm/s, from 50 cm/s to 100 cm/s, from 1 cm/s to 10 cm/s, from 10 cm/s to 20 cm/s, from 20 to 30 cm/s, from 30 to 40 cm/s, from 40 to 50 cm/s, from 1 cm/s to 4 cm/s, or from 1 cm/s to 20 cm/s). In some examples, the speed at which the droplet is translocated can be selected based on the strength of the fifth DC voltage applied to the second DC electrode.

In some examples, the second detection region of the confinement region and the second junction of the confinement region comprise substantially the same region of the confinement region, and in those examples no fifth DC voltage is applied.

The methods can, in some examples, further comprise applying a sixth DC voltage to the second DC electrode, the fourth DC electrode, the fifth DC electrode, or a combination thereof to translocate the droplet from the second junction of the confinement region to the fourth arm of the confinement region or the fifth arm of the confinement region based on the second characteristic of the particle, thereby sorting the droplet (e.g., into the fourth or fifth arm of the confinement region) based on the second characteristic of the particle.

The sixth DC voltage can, for example, be −75 V or more (e.g., −70 V or more, −65 V or more, −60 V or more, −55 V or more, −50 V or more, −45 V or more, −40 V or more, −35 V or more, −30 V or more, −25 V or more, −20 V or more, −15 V or more, −10 V or more, −5 V or more, 0 V or more, 5 V or more, 10 V or more, 15 V or more, 20 V or more, 25 V or more, 30 V or more, 35 V or more, 40 V or more, 45 V or more, 50 V or more, 55 V or more, 60 V or more, 65 V or more, or 70 V or more). In some examples, the sixth DC voltage can be 75 V or less (e.g., 70 V or less, 65 V or less, 60 V or less, 55 V or less, 50 V or less, 45 V or less, 40 V or less, 35 V or less, 30 V or less, 25 V or less, 20 V or less, 15 V or less, 10 V or less, 5 V or less, 0 V or less, −5 V or less, −10 V or less, −15 V or less, −20 V or less, −25 V or less, −30 V or less, −35 V or less, −40 V or less, −45 V or less, −50 V or less, −55 V or less, −60 V or less, −65 V or less, or −70 V or less). The sixth DV voltage can range from any of the minimum values described above to any of the maximum values described above. For example, the sixth DC voltage can be from −75 V to 75 V (e.g., from −75 V to 0 V, from 0 V to 75 V, from −65 V to 65 V, from −55 V to 55 V, or from −45 V to 45 V).

In some examples, the droplet is translocated from the second junction of the confinement region to the fourth or fifth arm of the confinement region at a speed of 1 cm/s or more (e.g., 1.25 cm/s or more, 1.5 cm/s or more, 1.75 cm/s or more, 2 cm/s or more, 2.25 cm/s or more, 2.5 cm/s or more, 2.75 cm/s or more, 3 cm/s or more, 3.25 cm/s or more, 3.5 cm/s or more, 3.75 cm/s or more, 4 cm/s or more, 4.5 cm/s or more, 5 cm/s or more, 6 cm/s or more, 7 cm/s or more, 8 cm/s or more, 9 cm/s or more, 10 cm/s or more, 15 cm/s or more, 20 cm/s or more, 30 cm/s or more, 40 cm/s or more, 50 cm/s or more, 75 cm/s or more). In some examples, the droplet is translocated from the second junction of the confinement region to the fourth or fifth arm of the confinement region at a speed of 100 cm/s or less (e.g., 75 cm/s or less, 50 cm/s or less, 40 cm/s or less, 30 cm/s or less, 20 cm/s or less, 15 cm/s or less, 10 cm/s or less, 9 cm/s or less, 8 cm/s or less, 7 cm/s or less, 6 cm/s or less, 5 cm/s or less, 4.5 cm/s or less, 4 cm/s or less, 3.75 cm/s or less, 3.5 cm/s or less, 3.25 cm/s or less, 3 cm/s or less, 2.75 cm/s or less, 2.5 cm/s or less, 2.25 cm/s or less, 2 cm/s or less, 1.75 cm/s or less, 1.5 cm/s or less, or 1.25 cm/s or less). The speed at which the droplet is translocated from the second junction of the confinement region to the fourth or fifth arm of the confinement region can range from any of the minimum values described above to any of the maximum values described above. For example, the droplet can be translocated from the second junction of the confinement region to the fourth or fifth arm of the confinement region at a speed of from 1 cm/s to 100 cm/s (e.g., from 1 cm/s to 50 cm/s, from 50 cm/s to 100 cm/s, from 1 cm/s to 10 cm/s, from 10 cm/s to 20 cm/s, from 20 to 30 cm/s, from 30 to 40 cm/s, from 40 to 50 cm/s, from 1 cm/s to 4 cm/s, or from 1 cm/s to 20 cm/s). In some examples, the speed at which the droplet is translocated can be selected based on the strength of the sixth DC voltage applied to the second DC electrode, fourth DC electrode, fifth DC electrode, or a combination thereof.

In some examples, the droplet is sorted into the fourth arm of the confinement region. In some examples, the fourth arm of the channel further comprises a collection region such that the fourth arm of the confinement region further comprises a collection region (e.g., such that the fourth arm of the confinement region extends from the second junction to the collection region). In some examples, the method further comprises applying a seventh DC voltage to the fourth DC electrode to translocate the droplet to the collection region of the fourth arm of the confinement region. In some examples, the methods can further comprise collecting the droplet by turning off the AC voltage to at least the fourth pair of AC electrodes, such that the droplet falls into the collection region of the fourth arm of the channel.

In some examples, the droplet is sorted into the fifth arm of the confinement region. In some examples, the fifth arm of the channel further comprises a collection region such that fifth arm of the confinement region further comprises a collection region (e.g., such that the fifth arm of the confinement region extends form the second junction to the collection region). The methods can, for example, further comprise applying a seventh DC voltage to the fifth DC electrode to translocate the droplet to the collection region of the fifth arm of the confinement region. In some examples, the methods further comprise collecting the droplet by turning off the AC voltage to at least the fifth pair of AC electrodes such that the droplet falls into the collection region of the fifth arm of the channel.

In some examples, the seventh DC voltage can be −75 V or more (e.g., −70 V or more, −65 V or more, −60 V or more, −55 V or more, −50 V or more, −45 V or more, −40 V or more, −35 V or more, −30 V or more, −25 V or more, −20 V or more, −15 V or more, −10 V or more, −5 V or more, 0 V or more, 5 V or more, 10 V or more, 15 V or more, 20 V or more, 25 V or more, 30 V or more, 35 V or more, 40 V or more, 45 V or more, 50 V or more, 55 V or more, 60 V or more, 65 V or more, or 70 V or more). In some examples, the seventh DC voltage can be 75 V or less (e.g., 70 V or less, 65 V or less, 60 V or less, 55 V or less, 50 V or less, 45 V or less, 40 V or less, 35 V or less, 30 V or less, 25 V or less, 20 V or less, 15 V or less, 10 V or less, 5 V or less, 0 V or less, −5 V or less, −10 V or less, −15 V or less, −20 V or less, −25 V or less, −30 V or less, −35 V or less, −40 V or less, −45 V or less, −50 V or less, −55 V or less, −60 V or less, −65 V or less, or −70 V or less). The seventh DC voltage can range from any of the minimum values described above to any of the maximum values described above. For example, the seventh DC voltage can be from −75 V to 75 V (e.g., from −75 V to 0 V, from 0 V to 75 V, from −65 V to 65 V, from −55 V to 55 V, or from −45 V to 45 V).

In some examples, the droplet is translocated within the fourth or fifth arm of the confinement region to the collection region at a speed of 1 cm/s or more (e.g., 1.25 cm/s or more, 1.5 cm/s or more, 1.75 cm/s or more, 2 cm/s or more, 2.25 cm/s or more, 2.5 cm/s or more, 2.75 cm/s or more, 3 cm/s or more, 3.25 cm/s or more, 3.5 cm/s or more, 3.75 cm/s or more, 4 cm/s or more, 4.5 cm/s or more, 5 cm/s or more, 6 cm/s or more, 7 cm/s or more, 8 cm/s or more, 9 cm/s or more, 10 cm/s or more, 15 cm/s or more, 20 cm/s or more, 30 cm/s or more, 40 cm/s or more, 50 cm/s or more, 75 cm/s or more). In some examples, the droplet is translocated within the fourth or fifth arm of the confinement region to the collection region at a speed of 100 cm/s or less (e.g., 75 cm/s or less, 50 cm/s or less, 40 cm/s or less, 30 cm/s or less, 20 cm/s or less, 15 cm/s or less, 10 cm/s or less, 9 cm/s or less, 8 cm/s or less, 7 cm/s or less, 6 cm/s or less, 5 cm/s or less, 4.5 cm/s or less, 4 cm/s or less, 3.75 cm/s or less, 3.5 cm/s or less, 3.25 cm/s or less, 3 cm/s or less, 2.75 cm/s or less, 2.5 cm/s or less, 2.25 cm/s or less, 2 cm/s or less, 1.75 cm/s or less, 1.5 cm/s or less, or 1.25 cm/s or less). The speed at which the droplet is translocated within the fourth or fifth arm of the confinement region to the collection region can range from any of the minimum values described above to any of the maximum values described above. For example, the droplet can be translocated within the fourth or fifth arm of the confinement region to the collection region at a speed of from 1 cm/s to 100 cm/s (e.g., from 1 cm/s to 50 cm/s, from 50 cm/s to 100 cm/s, from 1 cm/s to 10 cm/s, from 10 cm/s to 20 cm/s, from 20 to 30 cm/s, from 30 to 40 cm/s, from 40 to 50 cm/s, from 1 cm/s to 4 cm/s, or from 1 cm/s to 20 cm/s). In some examples, the speed at which the droplet is translocated can be selected based on the strength of the seventh DC voltage applied to the fourth DC electrode or fifth DC electrode.

In some examples, the third arm of the confinement region further comprises third detection region. In some examples, the device further comprises: a sixth pair of alternating current (AC) electrodes disposed on the surface of the insulating substrate, wherein each of the AC electrodes comprising the sixth pair of AC electrodes is spaced apart on the surface of the insulating substrate such that the sixth pair of AC electrodes define a sixth arm of a channel, and wherein each of AC electrodes comprising the sixth pair of AC electrodes is electrically connected to an AC voltage source; a sixth direct current (DC) electrode disposed on the surface of the insulating substrate and interspersed within the sixth arm of the channel, wherein the sixth DC electrode is electrically connected to a DC voltage source; a seventh pair of alternating current (AC) electrodes disposed on the surface of the insulating substrate, wherein each of the AC electrodes comprising the seventh pair of AC electrodes is spaced apart on the surface of the insulating substrate such that the seventh pair of AC electrodes define a seventh arm of a channel, and wherein each of AC electrodes comprising the seventh pair of AC electrodes is electrically connected to an AC voltage source; and a seventh direct current (DC) electrode disposed on the surface of the insulating substrate and interspersed within the seventh arm of the channel, wherein the seventh DC electrode is electrically connected to a DC voltage source; wherein the third arm of the channel, the sixth arm of the channel, and the seventh arm of the channel intersect at a third junction.

In some examples, the methods can further comprise applying AC voltage to the sixth pair of AC electrodes and the seventh pair of AC electrodes, such that the confinement region further comprises a sixth arm and a seventh arm, wherein the third, sixth, and seventh arms of the confinement region intersect at a third junction. In some examples, the AC voltage applied to the sixth pair of AC electrodes and/or the seventh pair of AC electrodes can have a peak-to-peak voltage of 100 Volts (V) or more (e.g., 150 V or more, 200 V or more, 250 V or more, 300 V or more, 350 V or more, 400 V or more, 450 V or more, 500 V or more, 550 V or more, 600 V or more, 650 V or more, 700 V or more, 750 V or more, 800 V or more, 850 V or more, 900 V or more, 950 V or more, 1000 V or more, 1050 V or more, 1100 V or more, or 1150 V or more). In some examples, the AC voltage applied to the sixth pair of AC electrodes and/or the seventh pair of AC electrodes has a peak-to-peak voltage of 1200 V or less (e.g., 1150 V or less, 1100 V or less, 1050 V or less, 1000 V or less, 950 V or less, 900 V or less, 850 V or less, 800 V or less, 750 V or less, 700 V or less, 650 V or less, 600 V or less, 550 V or less, 500 V or less, 450 V or less, 400 V or less, 350 V or less, 300 V or less, 250 V or less, 200 V or less, or 150 V or less). The peak-to-peak voltage of the AC voltage applied to the sixth pair of AC electrodes and/or the seventh pair of AC electrodes can range from any of the minimum values described above to any of the maximum values described above. For example, the AC voltage applied to the sixth pair of AC electrodes and/or the seventh pair of AC electrodes can a peak-to-peak voltage of from 100 V to 1200 V (e.g., from 100 V to 600 V, from 600 V to 1200 V, from 100 V to 400 V, from 400 V to 700 V, from 700 V to 1000 V, from 1000 V to 1200 V, or from 600 V to 1000 V). In some examples, the maximum AC voltage can be selected based on the eleventh distance and/or the thirteenth distance. In some examples, the peak-to-peak voltage of the AC voltage applied to the sixth pair of AC electrodes and/or the seventh pair of AC electrodes is the same as the peak-to-peak voltage applied to the first pair of AC electrodes, the second pair of AC electrodes, the third pair of AC electrodes, the fourth pair of AC electrodes, the fifth pair of AC electrodes, or a combination thereof.

In some examples, the AC voltage applied to the sixth pair of AC electrodes and/or the seventh pair of AC electrodes has a frequency of 50 Hertz (Hz) or more (e.g., 75 Hz or more, 100 Hz or more, 125 Hz or more, 150 Hz or more, 175 Hz or more, 200 Hz or more, 225 Hz or more, 250 Hz or more, 275 Hz or more, 300 Hz or more, 325 Hz or more, 350 Hz or more, 375 Hz or more, 400 Hz or more, 450 Hz or more, 500 Hz or more, 550 Hz or more, 600 Hz or more, 700 Hz or more, 800 Hz or more, or 900 Hz or more). In some examples, the AC voltage applied to the sixth pair of AC electrodes and/or the seventh pair of AC electrodes has a frequency of 1000 Hz or less (e.g., 900 Hz or less, 800 Hz or less, 700 Hz or less, 600 Hz or less, 550 Hz or less, 500 Hz or less, 450 Hz or less, 400 Hz or less, 375 Hz or less, 350 Hz or less, 325 Hz or less, 300 Hz or less, 275 Hz or less, 250 Hz or less, 225 Hz or less, 200 Hz or less, 175 Hz or less, 150 Hz or less, 125 Hz or less, 100 Hz or less, or 75 Hz or less). The frequency of the AC voltage applied to the sixth pair of AC electrodes and/or the seventh pair of AC electrodes can range from any of the minimum values described above to any of the maximum values described above. For example, the AC voltage applied to the sixth pair of AC electrodes and/or the seventh pair of AC electrodes has a frequency of from 50 Hz to 1000 Hz (e.g., from 50 Hz to 500 Hz, from 500 Hz to 1000 Hz, from 50 Hz to 200 Hz, from 200 Hz to 400 Hz, from 400 Hz to 600 Hz, from 600 Hz to 800 Hz, or from 800 Hz to 1000 Hz). In some examples, the frequency of the AC voltage applied to the sixth pair of AC electrodes and/or the seventh pair of AC electrodes is the same as the frequency applied to the first pair of AC electrodes, the second pair of AC electrodes, the third pair of AC electrodes, the fourth pair of AC electrodes, the fifth pair of AC electrodes, or a combination thereof.

The confinement region can, for example, further comprise a sixth arm and a seventh arm, wherein the third, sixth, and seventh arms of the confinement region intersect at a third junction. In some examples, an axis traversing the sixth arm of the channel and an axis traversing the sixth arm of the confinement region are substantially parallel. In some examples, an axis traversing the seventh arm of the channel and an axis traversing the seventh arm of the confinement region are substantially parallel. For example, the third arm of the confinement region can split into the fourth and fifth arms of the confinement region at the third junction. In some examples, the third arm of the confinement region can split into a plurality of additional arms at the third junction.

In some examples, the first junction of the confinement region is fluidly connected to the third junction of the confinement region via the third arm of the confinement region, such that the third detection region is fluidly connected to the third junction of the confinement region; and the third arm of the confinement region is fluidly connected to the sixth arm of the confinement region and the seventh arm of the confinement region via the third junction of the confinement region, such that the confinement region defines a path for fluid flow from the first junction of the confinement region to the third detection region, from the third detection region to the third junction of the confinement region, and from the third junction of the confinement region along the sixth arm of the confinement region and the seventh arm of the confinement region.

In some examples, the droplet is in the third arm of the confinement region; and the method further comprises applying an eighth DC voltage to the third DC electrode to translocate the droplet to the third detection region. In some examples, the eighth DC voltage can be −75 V or more (e.g., −70 V or more, −65 V or more, −60 V or more, −55 V or more, −50 V or more, −45 V or more, −40 V or more, −35 V or more, −30 V or more, −25 V or more, −20 V or more, −15 V or more, −10 V or more, −5 V or more, 0 V or more, 5 V or more, 10 V or more, 15 V or more, 20 V or more, 25 V or more, 30 V or more, 35 V or more, 40 V or more, 45 V or more, 50 V or more, 55 V or more, 60 V or more, 65 V or more, or 70 V or more). In some examples, the eighth DC voltage can be 75 V or less (e.g., 70 V or less, 65 V or less, 60 V or less, 55 V or less, 50 V or less, 45 V or less, 40 V or less, 35 V or less, 30 V or less, 25 V or less, 20 V or less, 15 V or less, 10 V or less, 5 V or less, 0 V or less, −5 V or less, −10 V or less, −15 V or less, −20 V or less, −25 V or less, −30 V or less, −35 V or less, −40 V or less, −45 V or less, −50 V or less, −55 V or less, −60 V or less, −65 V or less, or −70 V or less). The eighth DC voltage can range from any of the minimum values described above to any of the maximum values described above. For example, the eighth DC voltage can be from −75 V to 75 V (e.g., from −75 V to 0 V, from 0 V to 75 V, from −65 V to 65 V, from −55 V to 55 V, or from −45 V to 45 V).

In some examples, the droplet is translocated within the third arm of the confinement region to the third detection region at a speed of 1 cm/s or more (e.g., 1.25 cm/s or more, 1.5 cm/s or more, 1.75 cm/s or more, 2 cm/s or more, 2.25 cm/s or more, 2.5 cm/s or more, 2.75 cm/s or more, 3 cm/s or more, 3.25 cm/s or more, 3.5 cm/s or more, 3.75 cm/s or more, 4 cm/s or more, 4.5 cm/s or more, 5 cm/s or more, 6 cm/s or more, 7 cm/s or more, 8 cm/s or more, 9 cm/s or more, 10 cm/s or more, 15 cm/s or more, 20 cm/s or more, 30 cm/s or more, 40 cm/s or more, 50 cm/s or more, 75 cm/s or more). In some examples, the droplet is translocated within the third arm of the confinement region to the third detection region at a speed of 100 cm/s or less (e.g., 75 cm/s or less, 50 cm/s or less, 40 cm/s or less, 30 cm/s or less, 20 cm/s or less, 15 cm/s or less, 10 cm/s or less, 9 cm/s or less, 8 cm/s or less, 7 cm/s or less, 6 cm/s or less, 5 cm/s or less, 4.5 cm/s or less, 4 cm/s or less, 3.75 cm/s or less, 3.5 cm/s or less, 3.25 cm/s or less, 3 cm/s or less, 2.75 cm/s or less, 2.5 cm/s or less, 2.25 cm/s or less, 2 cm/s or less, 1.75 cm/s or less, 1.5 cm/s or less, or 1.25 cm/s or less). The speed at which the droplet is translocated within the third arm of the confinement region to the third detection region can range from any of the minimum values described above to any of the maximum values described above. For example, the droplet can be translocated within the third arm of the confinement region to the third detection region at a speed of from 1 cm/s to 100 cm/s (e.g., from 1 cm/s to 50 cm/s, from 50 cm/s to 100 cm/s, from 1 cm/s to 10 cm/s, from 10 cm/s to 20 cm/s, from 20 to 30 cm/s, from 30 to 40 cm/s, from 40 to 50 cm/s, from 1 cm/s to 4 cm/s, or from 1 cm/s to 20 cm/s). In some examples, the speed at which the droplet is translocated can be selected based on the strength of the eighth DC voltage applied to the third DC electrode.

The methods can, in some examples, further comprise determining a third characteristic of the particle in the droplet at the third detection region. The third characteristic of the particle can be different than the first characteristic of the particle. Determining a third characteristic of the particle in the droplet can, for example, comprise capturing an electromagnetic signal from the particle and/or the droplet and analyzing the electromagnetic signal from the particle and/or the droplet to determine the third characteristic of the particle. The electromagnetic signal can, in some examples, comprise an optical signal, a spectroscopic signal, or a combination thereof. Examples of electromagnetic signals include, but are not limited to, color, intensity, brightness, absorbance, scattering, fluorescence, frequency, wavelength, or a combination thereof. The second characteristic of the particle can, for example, comprises the presence, absence, or intensity of absorbance; the presence, absence, or intensity of scattering; the presence, absence, or intensity of fluorescence; the size of the particle; the number of particles in the droplet; or a combination thereof.

In some examples, the droplet is present in the third detection region of the confinement region for an amount of time of 10 microseconds (μs) or more (e.g., 20 μs or more, 30 μs or more, 40 μs or more, 50 μs or more, 75 μs or more, 100 μs or more, 125 μs or more, 150 μs or more, 200 μs or more, 250 μs or more, 300 μs or more, 350 μs or more, 400 μs or more, 500 μs or more, 600 μs or more, 700 μs or more, 800 μs or more, 900 μs or more, 1 millisecond (ms) or more, 5 ms or more, 10 ms or more, 20 ms or more, 30 ms or more, 40 ms or more, 50 ms or more, 75 ms or more, 100 ms or more, 125 ms or more, 150 ms or more, 200 ms or more, 250 ms or more, 300 ms or more, 350 ms or more, 400 ms or more, 500 ms or more, 600 ms or more, 700 ms or more, 800 ms or more, 900 ms or more, 1 second or more, 2 seconds or more, 3 seconds or more, 4 seconds or more, 5 seconds or more, 6 seconds or more, 7 seconds or more, 8 seconds or more, 9 seconds or more, 10 seconds or more, 15 seconds or more, 30 seconds or more, 45 seconds or more, or 1 minute or more). In some examples, the droplet is present in the third detection region of the confinement region for an amount of time of 5 minutes or less (e.g., 1 minute or less, 45 seconds or less, 30 seconds or less, 15 seconds or less, 10 seconds or less, 9 seconds or less, 8 seconds or less, 7 seconds or less, 6 seconds or less, 5 seconds or less, 4 seconds or less, 3 seconds or less, 2 seconds or less, 1 second or less, 900 ms or less, 800 ms or less, 700 ms or less, 600 ms or less, 500 ms or less, 400 ms or less, 350 ms or less, 300 ms or less, 250 ms or less, 200 ms or less, 150 ms or less, 125 ms or less, 100 ms or less, 75 ms or less, 50 ms or less, 40 ms or less, 30 ms or less, 20 ms or less, 10 ms or less, 5 ms or less, 1 ms or less, 900 µs or less, 800 µs or less, 700 µs or less, 600 µs or less, 500 µs or less, 400 µs or less, 350 µs or less, 300 µs or less, 250 µs or less, 200 µs or less, 150 µs or less, 125 µs or less, 100 µs or less, 75 µs or less, 50 µs or less, 40 µs or less, 30 µs or less, or 20 µs or less). The amount of time the droplet is present in the third detection region of the confinement region can range from any of the minimum values described above to any of the maximum values described above. For example, the droplet can be present in the third detection region of the confinement region for an amount of time of from 10 µs to 5 minutes (e.g., from 10 µs to 100 µs, from 100 µs to 1 ms, from 1 ms to 10 ms, from 10 ms to 100 ms, from 100 ms to 1 second, from 1 second to 1 minutes, from 1 minute to 5 minutes, or from 100 ms to 10 seconds). In some examples, the time for which the droplet is present in the third detection region can be selected based on the detection method, the droplet's lifetime, and the particle's lifetime within the droplet.

The methods can further comprise, for example, applying a ninth DC voltage to the third DC electrode to translocate the droplet from the third detection region to the third junction of the confinement region. In some examples, the ninth DC voltage can be 75 V or more (e.g., −70 V or more, −65 V or more, −60 V or more, −55 V or more, −50 V or more, −45 V or more, −40 V or more, −35 V or more, −30 V or more, −25 V or more, −20 V or more, −15 V or more, −10 V or more, −5 V or more, 0 V or more, 5 V or more, 10 V or more, 15 V or more, 20 V or more, 25 V or more, 30 V or more, 35 V or more, 40 V or more, 45 V or more, 50 V or more, 55 V or more, 60 V or more, 65 V or more, or 70 V or more). In some examples, the ninth DC voltage can be 75 V or less (e.g., 70 V or less, 65 V or less, 60 V or less, 55 V or less, 50 V or less, 45 V or less, 40 V or less, 35 V or less, 30 V or less, 25 V or less, 20 V or less, 15 V or less, 10 V or less, 5 V or less, 0 V or less, −5 V or less, −10 V or less, −15 V or less, −20 V or less, −25 V or less, −30 V or less, −35 V or less, −40 V or less, −45 V or less, −50 V or less, −55 V or less, −60 V or less, −65 V or less, or −70 V or less). The ninth DC voltage can range from any of the minimum values described above to any of the maximum values described above. For example, the ninth DC voltage can be from −75 V to 75 V (e.g., from −75 V to 0 V, from 0 V to 75 V, from −65 V to 65 V, from −55 V to 55 V, or from −45 V to 45 V).

In some examples, the droplet is translocated from the third detection region to the third junction of the confinement region at a speed of 1 cm/s or more (e.g., 1.25 cm/s or more, 1.5 cm/s or more, 1.75 cm/s or more, 2 cm/s or more, 2.25 cm/s or more, 2.5 cm/s or more, 2.75 cm/s or more, 3 cm/s or more, 3.25 cm/s or more, 3.5 cm/s or more, 3.75 cm/s or more, 4 cm/s or more, 4.5 cm/s or more, 5 cm/s or more, 6 cm/s or more, 7 cm/s or more, 8 cm/s or more, 9 cm/s or more, 10 cm/s or more, 15 cm/s or more, 20 cm/s or more, 30 cm/s or more, 40 cm/s or more, 50 cm/s or more, 75 cm/s or more). In some examples, the droplet is translocated from the third detection region to the third junction of the confinement region at a speed of 100 cm/s or less (e.g., 75 cm/s or less, 50 cm/s or less, 40 cm/s or less, 30 cm/s or less, 20 cm/s or less, 15 cm/s or less, 10 cm/s or less, 9 cm/s or less, 8 cm/s or less, 7 cm/s or less, 6 cm/s or less, 5 cm/s or less, 4.5 cm/s or less, 4 cm/s or less, 3.75 cm/s or less, 3.5 cm/s or less, 3.25 cm/s or less, 3 cm/s or less, 2.75 cm/s or less, 2.5 cm/s or less, 2.25 cm/s or less, 2 cm/s or less, 1.75 cm/s or less, 1.5 cm/s or less, or 1.25 cm/s or less). The speed at which the droplet is translocated from the third detection region to the third junction of the confinement region at a speed of can range from any of the minimum values described above to any of the maximum values described above. For example, the droplet can be translocated from the third detection region to the third junction of the confinement region at a speed of from 1 cm/s to 100 cm/s (e.g., from 1 cm/s to 50 cm/s, from 50 cm/s to 100 cm/s, from 1 cm/s to 10 cm/s, from 10 cm/s to 20 cm/s, from 20 to 30 cm/s, from 30 to 40 cm/s, from 40 to 50 cm/s, from 1 cm/s to 4 cm/s, or from 1 cm/s to 20 cm/s). In some examples, the speed at which the droplet is translocated can be selected based on the strength of the ninth DC voltage applied to the third DC electrode.

In some examples, the third detection region of the confinement region and the third junction of the confinement region comprise substantially the same region of the confinement region, and in those examples no ninth DC voltage is applied.

In some examples, the methods can further comprise applying a tenth DC voltage to the third DC electrode, the sixth DC electrode, the seventh DC electrode, or a combination thereof to translocate the droplet from the third junction of the confinement region to the sixth arm of the confinement region or the seventh arm of the confinement region based on the third characteristic of the particle, thereby sorting the droplet (e.g., into the sixth or seventh arm of the confinement region) based on the third characteristic of the particle.

The tenth DC voltage can, for example, be −75 V or more (e.g., −70 V or more, −65 V or more, −60 V or more, −55 V or more, −50 V or more, −45 V or more, −40 V or more, −35 V or more, −30 V or more, −25 V or more, −20 V or more, −15 V or more, −10 V or more, −5 V or more, 0 V or more, 5 V or more, 10 V or more, 15 V or more, 20 V or more, 25 V or more, 30 V or more, 35 V or more, 40 V or more, 45 V or more, 50 V or more, 55 V or more, 60 V or more, 65 V or more, or 70 V or more). In some examples, the tenth DC voltage can be 75 V or less (e.g., 70 V or less, 65 V or less, 60 V or less, 55 V or less, 50 V or less, 45 V or less, 40 V or less, 35 V or less, 30 V or less, 25 V or less, 20 V or less, 15 V or less, 10 V or less, 5 V or less, 0 V or less, −5 V or less, −10 V or less, −15 V or less, −20 V or less, −25 V or less, −30 V or less, −35 V or less, −40 V or less, −45 V or less, −50 V or less, −55 V or less, −60 V or less, −65 V or less, or −70 V or less). The tenth DC voltage can range from any of the minimum values described above to any of the maximum values described above. For example, the tenth DC voltage can be from −75 V to 75 V (e.g., from −75 V to 0 V, from 0 V to 75 V, from −65 V to 65 V, from −55 V to 55 V, or from −45 V to 45 V).

In some examples, the droplet is translocated from the third junction of the confinement region to the sixth or seventh arm of the confinement region at a speed of 1 cm/s or more (e.g., 1.25 cm/s or more, 1.5 cm/s or more, 1.75 cm/s or more, 2 cm/s or more, 2.25 cm/s or more, 2.5 cm/s or more, 2.75 cm/s or more, 3 cm/s or more, 3.25 cm/s or more, 3.5 cm/s or more, 3.75 cm/s or more, 4 cm/s or more, 4.5 cm/s or more, 5 cm/s or more, 6 cm/s or more, 7 cm/s or more, 8 cm/s or more, 9 cm/s or more, 10 cm/s or more, 15 cm/s or more, 20 cm/s or more, 30 cm/s or more, 40 cm/s or more, 50 cm/s or more, 75 cm/s or more). In some examples, the droplet is translocated from the third junction of the confinement region to the sixth or seventh arm of the confinement region at a speed of 100 cm/s or less (e.g., 75 cm/s or less, 50 cm/s or less, 40 cm/s or less, 30 cm/s or less, 20 cm/s or less, 15 cm/s or less, 10 cm/s or less, 9 cm/s or less, 8 cm/s or less, 7 cm/s or less, 6 cm/s or less, 5 cm/s or less, 4.5 cm/s or less, 4 cm/s or less, 3.75 cm/s or less, 3.5 cm/s or less, 3.25 cm/s or less, 3 cm/s or less, 2.75 cm/s or less, 2.5 cm/s or less, 2.25 cm/s or less, 2 cm/s or less, 1.75 cm/s or less, 1.5 cm/s or less, or 1.25 cm/s or less). The speed at which the droplet is translocated from the third junction of the confinement region to the sixth or seventh arm of the confinement region can range from any of the minimum values described above to any of the maximum values described above. For example, the droplet is translocated from the third junction of the confinement region to the sixth or seventh arm of the confinement region at a speed of from 1 cm/s to 100 cm/s (e.g., from 1 cm/s to 50 cm/s, from 50 cm/s to 100 cm/s, from 1 cm/s to 10 cm/s, from 10 cm/s to 20 cm/s, from 20 to 30 cm/s, from 30 to 40 cm/s, from 40 to 50 cm/s, from 1 cm/s to 4 cm/s, or from 1 cm/s to 20 cm/s). In some examples, the speed at which the droplet is translocated can be selected based on the strength of the tenth DC voltage applied to the third DC electrode, sixth DC electrode, seventh DC electrode, or a combination thereof.

In some examples, the droplet is sorted into the sixth arm of the confinement region. In some examples, the sixth arm of the channel further comprises a collection region such that the sixth arm of the confinement region further comprises a collection region (e.g., such that the sixth arm of the confinement region extends from the third junction to the collection region). The methods can further comprise, in some examples, applying an eleventh DC voltage to the sixth DC electrode to translocate the droplet to the collection region of the sixth arm of the confinement. The methods can, for example, further comprise collecting the droplet by turning off the AC voltage to at least the sixth pair of AC electrodes, such that the droplet falls into the collection region of the sixth arm of the channel.

In some examples, the droplet is sorted into the seventh arm of the confinement region. In some examples, the seventh arm of the channel further comprises a collection region such that seventh arm of the confinement region further comprises a collection region (e.g., such that the seventh arm of the confinement region extends from the third junction to the collection region). The methods can, for example, further comprise applying an eleventh DC voltage to the seventh DC electrode to translocate the droplet to the collection region of the seventh arm of the confinement region. In some examples, the methods can further comprise collecting the droplet by turning off the AC voltage to at least the seventh pair of AC electrodes, such that the droplet falls into the collection region of the seventh arm of the channel.

In some examples, the eleventh DC voltage can be −75 V or more (e.g., −70 V or more, −65 V or more, −60 V or more, −55 V or more, −50 V or more, −45 V or more, −40 V or more, −35 V or more, −30 V or more, −25 V or more, −20 V or more, −15 V or more, −10 V or more, −5 V or more, 0 V or more, 5 V or more, 10 V or more, 15 V or more, 20 V or more, 25 V or more, 30 V or more, 35 V or more, 40 V or more, 45 V or more, 50 V or more, 55 V or more, 60 V or more, 65 V or more, or 70 V or more). In some examples, the eleventh DC voltage can be 75 V or less (e.g., 70 V or less, 65 V or less, 60 V or less, 55 V or less, 50 V or less, 45 V or less, 40 V or less, 35 V or less, 30 V or less, 25 V or less, 20 V or less, 15 V or less, 10 V or less, 5 V or less, 0 V or less, −5 V or less, −10 V or less, −15 V or less, −20 V or less, −25 V or less, −30 V or less, −35 V or less, −40 V or less, −45 V or less, −50 V or less, −55 V or less, −60 V or less, −65 V or less, or −70 V or less). The eleventh DC voltage can range from any of the minimum values described above to any of the maximum values described above. For example, the eleventh DC voltage can be from −75 V to 75 V (e.g., from −75 V to 0 V, from 0 V to 75 V, from −65 V to 65 V, from −55 V to 55 V, or from −45 V to 45 V).

In some examples, the droplet is translocated within the sixth or seventh arm of the confinement region to the collection region at a speed of 1 cm/s or more (e.g., 1.25 cm/s or more, 1.5 cm/s or more, 1.75 cm/s or more, 2 cm/s or more, 2.25 cm/s or more, 2.5 cm/s or more, 2.75 cm/s or more, 3 cm/s or more, 3.25 cm/s or more, 3.5 cm/s or more, 3.75 cm/s or more, 4 cm/s or more, 4.5 cm/s or more, 5 cm/s or more, 6 cm/s or more, 7 cm/s or more, 8 cm/s or more, 9 cm/s or more, 10 cm/s or more, 15 cm/s or more, 20 cm/s or more, 30 cm/s or more, 40 cm/s or more, 50 cm/s or more, 75 cm/s or more). In some examples, the droplet is translocated within the sixth or seventh arm of the confinement region to the collection region at a speed of 100 cm/s or less (e.g., 75 cm/s or less, 50 cm/s or less, 40 cm/s or less, 30 cm/s or less, 20 cm/s or less, 15 cm/s or less, 10 cm/s or less, 9 cm/s or less, 8 cm/s or less, 7 cm/s or less, 6 cm/s or less, 5 cm/s or less, 4.5 cm/s or less, 4 cm/s or less, 3.75 cm/s or less, 3.5 cm/s or less, 3.25 cm/s or less, 3 cm/s or less, 2.75 cm/s or less, 2.5 cm/s or less, 2.25 cm/s or less, 2 cm/s or less, 1.75 cm/s or less, 1.5 cm/s or less, or 1.25 cm/s or less). The speed at which the droplet is translocated within the sixth or seventh arm of the confinement region to the collection region can range from any of the minimum values described above to any of the maximum values described above. For example, the droplet can be translocated within the sixth or seventh arm of the confinement region to the collection region at a speed of from 1 cm/s to 100 cm/s (e.g., from 1 cm/s to 50 cm/s, from 50 cm/s to 100 cm/s, from 1 cm/s to 10 cm/s, from 10 cm/s to 20 cm/s, from 20 to 30 cm/s, from 30 to 40 cm/s, from 40 to 50 cm/s, from 1 cm/s to 4 cm/s, or from 1 cm/s to 20 cm/s). In some examples, the speed at which the droplet is translocated can be selected based on the strength of the eleventh DC voltage applied to the sixth DC electrode or seventh DC electrode.

In some examples, the method is performed at room temperature. In some examples, the method is performed at atmospheric pressure.

The methods can, in some examples, further comprise injecting a second droplet into the loading region and repeating the sorting method described above for the second droplet.

Systems

Figure 6:
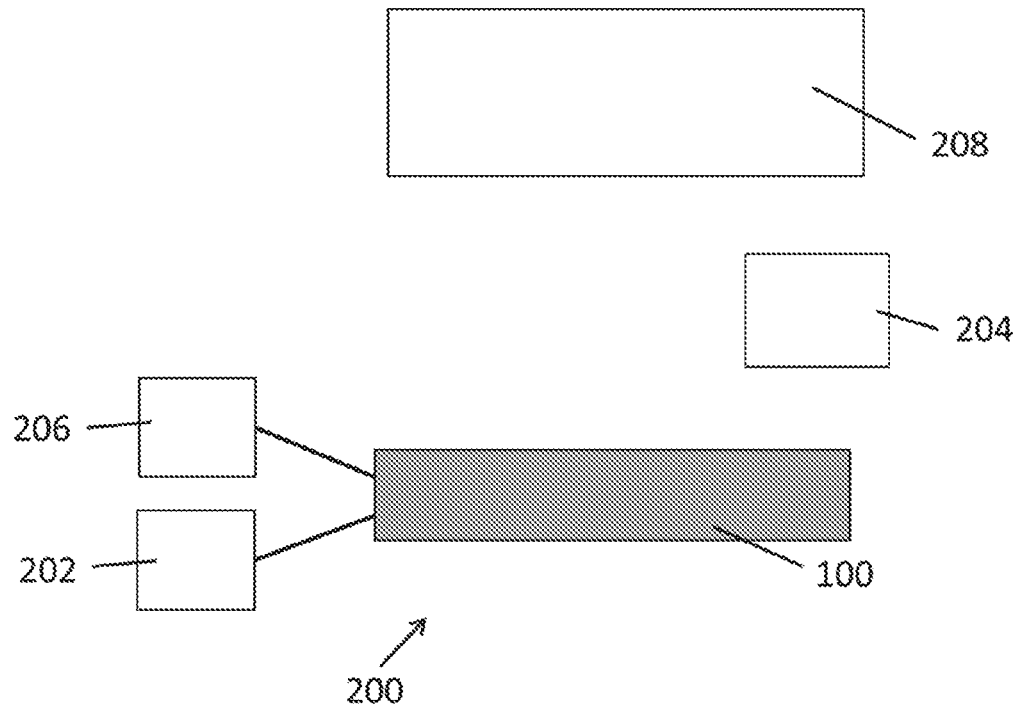
FIG. 6 is a schematic of an exemplary system as disclosed herein.

Also disclosed herein are systems comprising any of the devices described herein. Also disclosed herein are systems on which any of the methods described herein can be carried out. Referring now to FIG. 6, disclosed herein are systems 200 comprising a device 100.

The device 100 can comprise an insulating substrate 102 having a surface 104; a first pair of alternating current (AC) electrodes 106 disposed on the surface 104 of the insulating substrate 102, wherein each of the AC electrodes comprising the first pair of AC electrodes 106 is spaced apart on the surface 104 of the insulating substrate 102 such that the first pair of AC electrodes 106 define a first arm of a channel 108; a first direct current (DC) electrode 110 disposed on the surface 104 of the insulating substrate 102 and interspersed within the first arm of the channel 108; a second pair of alternating current (AC) electrodes 112 disposed on the surface 104 of the insulating substrate 102, wherein each of the AC electrodes comprising the second pair of AC electrodes 112 is spaced apart on the surface 104 of the insulating substrate 102 such that the second pair of AC electrodes 112 define a second arm of a channel 114; a second direct current (DC) electrode 116 disposed on the surface 104 of the insulating substrate 102 and interspersed within the second arm of the channel 114; a third pair of alternating current (AC) electrodes 118 disposed on the surface 104 of the insulating substrate 102, wherein each of the AC electrodes comprising the third pair of AC electrodes 118 is spaced apart on the surface 104 of the insulating substrate 102 such that the third pair of AC electrodes 118 define a third arm of a channel 120; and a third direct current (DC) electrode 122 disposed on the surface 104 of the insulating substrate 102 and interspersed within the third arm of the channel 120; wherein the first 108, second 114, and third 120 arms of the channel intersect at a junction 124.

The system 200 can further comprise an AC voltage source 202 electrically connected to the first pair of AC electrodes 106, the second pair of AC electrodes 112, and the third pair of AC electrodes 118, wherein applying an AC voltage to the first pair of AC electrodes 106, the second pair of AC electrodes 112, and the third pair of AC electrodes 118 generates an electromagnetic trapping field defining a confinement region, wherein the confinement region is proximate the channel and above the surface 104 of the insulating substrate; wherein the confinement region comprises a first arm, a second arm, and a third arm, and wherein the first, second, and third arms of the confinement region intersect at a junction; and wherein the first arm of the confinement region comprises a loading region and a detection region. The AC voltage source can comprise any suitable AC voltage source. Suitable AC voltage sources are known in the art.

The system 200 can further comprise a droplet generating device 204, wherein the electromagnetic trapping field traps a droplet having a surface charge injected into the loading region from the droplet generating device 204 in the confinement region, such that the droplet levitates above the surface 104 of the insulating substrate, wherein the droplet comprises a liquid sample comprising a particle. The droplet generating device 204 can, for example, ejects a droplet and exposes the ejected droplet to an electric bias, thereby forming the droplet having a surface charge. The electric bias can, for example, be from 300 V to 700 V. In some examples, the droplet generating device 204 comprises an ejector and a reservoir containing a volume of the liquid sample, wherein the reservoir is fluidly connected to the ejector. The droplet generating device 204 can, for example, comprises a piezoelectric droplet generating device.

The system 200 can further comprise a DC voltage source 206 electrically connected to the first DC electrode 110, the second DC electrode 116, and the third DC electrode 122, wherein applying a first DC voltage to the first DC electrode translocates the droplet from the loading region to the detection region. The DC voltage source can comprise any suitable DC voltage source. Suitable DC voltage sources are known in the art. In some examples, the DC voltage source can be a digital to analog converter (DAC) array.

The system 200 can further comprise an instrument 208 configured to determine a characteristic of the particle in the droplet at the detection region; wherein applying a second DC voltage to the first DC electrode 110 translocates the droplet from the detection region to the junction of the confinement region; and wherein applying a third DC voltage to the first DC electrode 110, the second DC electrode 116, the third DC electrode 122, of a combination thereof translocates the droplet from the junction of the confinement region to the second arm of the confinement region or the third arm of the confinement region based on the characteristic of the particle, thereby sorting the droplet based on the characteristic of the particle.

The instrument 208 can, for example, comprise a camera, an optical microscope, an electron microscope, a spectrometer, a dynamic light scattering instrument, or combinations thereof. Examples of spectrometers include, but are not limited to Raman spectrometers, UV-vis absorption spectrometers, IR absorption spectrometers, fluorescence spectrometers, and combinations thereof. In some examples, the system 200 can include any number of additional instruments.

Figure 7:
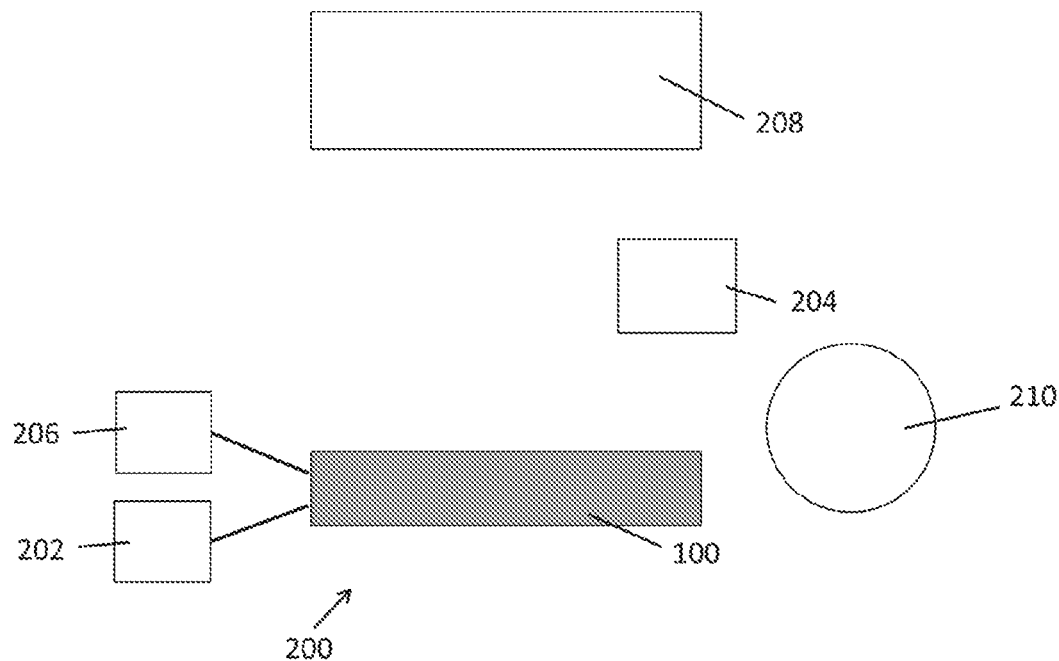
FIG. 7 is a schematic of an exemplary system as disclosed herein.

Referring now to FIG. 7, the system 200 can further comprise a light source 210 configured to illuminate the droplet in the detection region. The light source 210 can be in the same plane as the device 100 (e.g., in the same plane as the surface of the insulating substrate). In some examples, the light source 210 can be a single light source. In some examples, the light source 210 can comprise multiple light sources. The light source 210 can be any type of light source. Examples of suitable light sources include natural light sources (e.g., sunlight) and artificial light sources (e.g., incandescent light bulbs, light emitting diodes, gas discharge lamps, arc lamps, lasers, etc.). In some examples, the light source 210 is an artificial light source. In some examples, the light source 210 is a laser.

Figure 8:
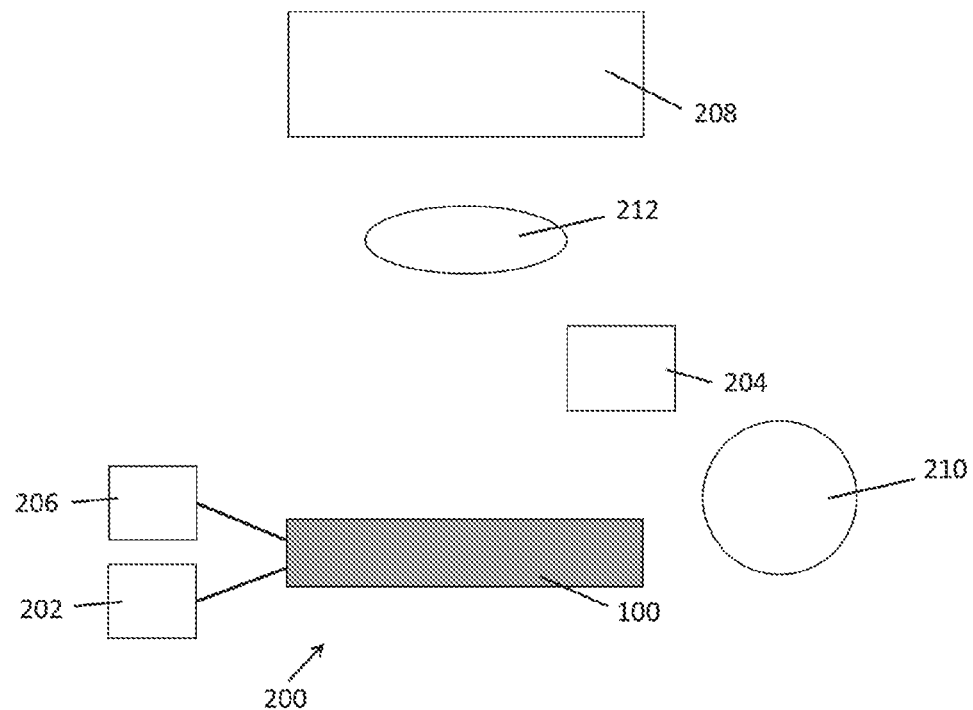
FIG. 8 is a schematic of an exemplary system as disclosed herein.
Figure 9:
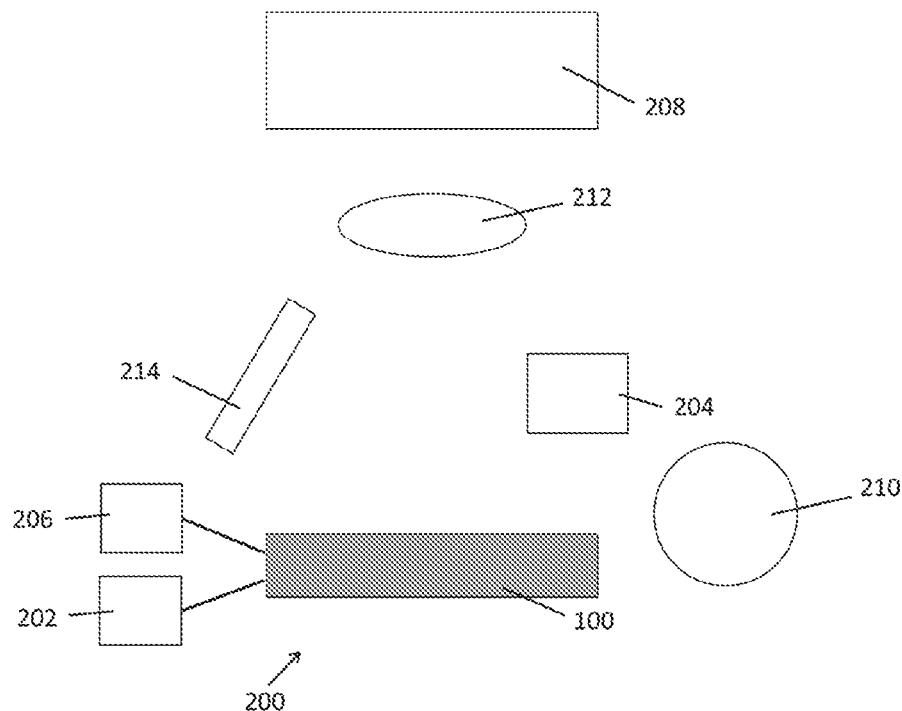
FIG. 9 is a schematic of an exemplary system as disclosed herein.

The system 200 can further comprise a first lens 212, for example as shown in FIG. 8. The system 200 can, for example, be aligned such that the light source 210 is below the first lens 212 and the instrument 208 is above the first lens 212. In some examples, the system can further include any number of additional lenses. The lenses may independently be any type of lens, such as a simple lens, a compound lens, a spherical lens, a toric lens, a biconvex lens, a plano-convex lens, a plano-concave lens, a negative meniscus lens, a positive meniscus lens, a biconcave lens, a converging lens, a diverging lens, a Fresnel lens, a lenticular lens, or a gradient index lens. Referring now to FIG. 9, the system 200 can further comprise a mirror 214. The system 200 can, for example, be aligned such that the light source 210 is configured to illuminate the mirror 214 and the mirror 214 is configured to reflect the electromagnetic radiation from the light source 210 to illuminate the droplet in the detection region.

Figure 10:
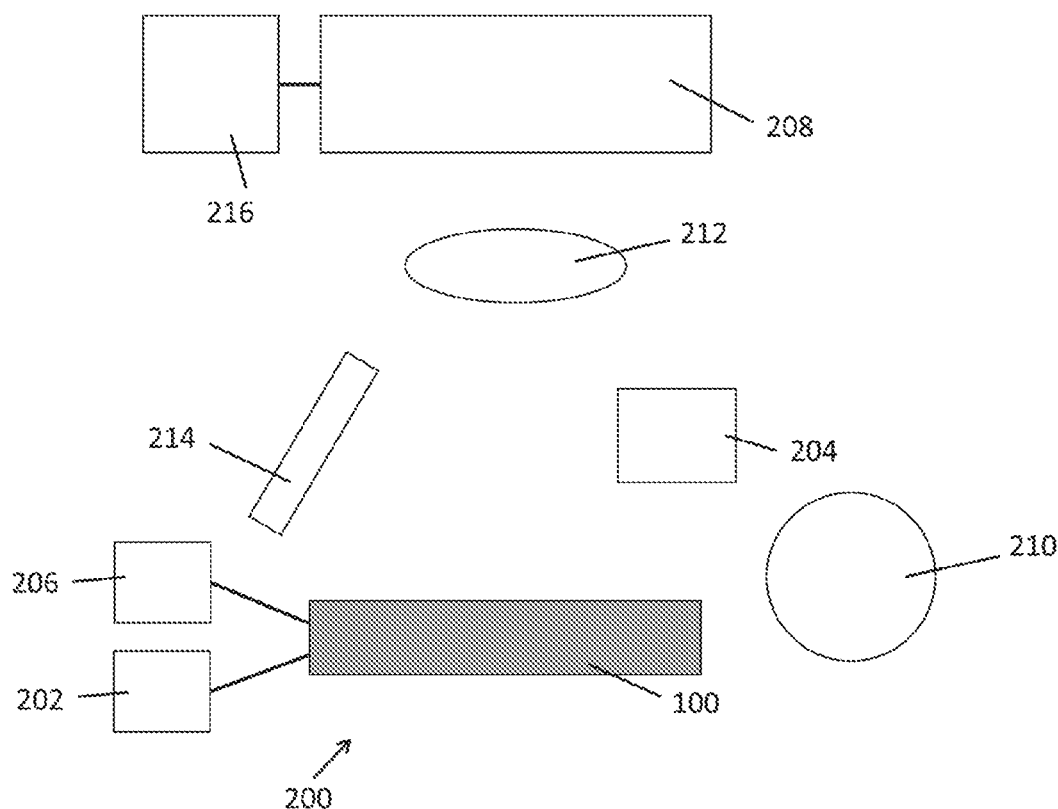
FIG. 10 is a schematic of an exemplary system as disclosed herein.

In some examples, the system 200 can further comprise a computing device 216 configured to receive and process electromagnetic signals from the instrument 208, for example as shown in FIG. 10.

Figure 11:
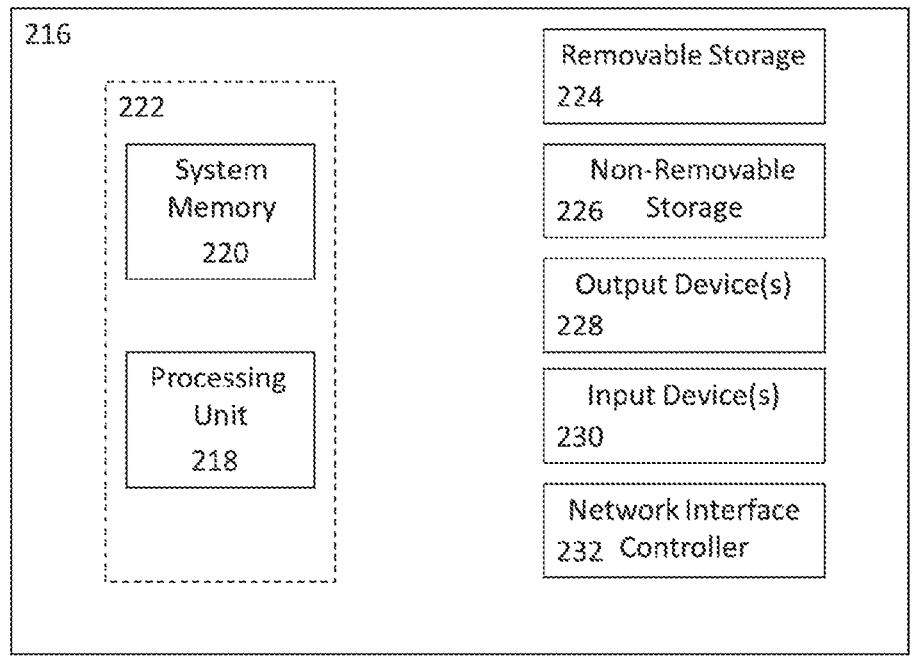
FIG. 11 is a schematic of an exemplary computing device.

FIG. 11 illustrates an example computing device 216 upon which examples disclosed herein may be implemented. The computing device 216 can include a bus or other communication mechanism for communicating information among various components of the computing device 216. In its most basic configuration, computing device 216 typically includes at least one processing unit 218 (a processor) and system memory 220. Depending on the exact configuration and type of computing device, system memory 220 may be volatile (such as random access memory (RAM)), non-volatile (such as read-only memory (ROM), flash memory, etc.), or some combination of the two. This most basic configuration is illustrated in FIG. 11 by a dashed line 222. The processing unit 218 may be a standard programmable processor that performs arithmetic and logic operations necessary for operation of the computing device 216.

The computing device 216 can have additional features/functionality. For example, computing device 216 may include additional storage such as removable storage 224 and non-removable storage 226 including, but not limited to, magnetic or optical disks or tapes. The computing device 216 can also contain network connection(s) 232 that allow the device to communicate with other devices. The computing device 216 can also have input device(s) 230 such as a keyboard, mouse, touch screen, antenna or other systems configured to communicate with the camera in the system described above, etc. Output device(s) 228 such as a display, speakers, printer, etc. may also be included. The additional devices can be connected to the bus in order to facilitate communication of data among the components of the computing device 216.

The processing unit 218 can be configured to execute program code encoded in tangible, computer-readable media. Computer-readable media refers to any media that is capable of providing data that causes the computing device 216 (i.e., a machine) to operate in a particular fashion. Various computer-readable media can be utilized to provide instructions to the processing unit 218 for execution. Common forms of computer-readable media include, for example, magnetic media, optical media, physical media, memory chips or cartridges, a carrier wave, or any other medium from which a computer can read. Example computer-readable media can include, but is not limited to, volatile media, non-volatile media and transmission media. Volatile and non-volatile media can be implemented in any method or technology for storage of information such as computer readable instructions, data structures, program modules or other data and common forms are discussed in detail below. Transmission media can include coaxial cables, copper wires and/or fiber optic cables, as well as acoustic or light waves, such as those generated during radio-wave and infra-red data communication. Example tangible, computer-readable recording media include, but are not limited to, an integrated circuit (e.g., field-programmable gate array or application-specific IC), a hard disk, an optical disk, a magneto-optical disk, a floppy disk, a magnetic tape, a holographic storage medium, a solid-state device, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices.

In an example implementation, the processing unit 218 can execute program code stored in the system memory 220. For example, the bus can carry data to the system memory 220, from which the processing unit 218 receives and executes instructions. The data received by the system memory 220 can optionally be stored on the removable storage 224 or the non-removable storage 226 before or after execution by the processing unit 218.

The computing device 216 typically includes a variety of computer-readable media. Computer-readable media can be any available media that can be accessed by device 216 and includes both volatile and non-volatile media, removable and non-removable media. Computer storage media include volatile and non-volatile, and removable and non-removable media implemented in any method or technology for storage of information such as computer readable instructions, data structures, program modules or other data. System memory 220, removable storage 224, and non-removable storage 226 are all examples of computer storage media. Computer storage media include, but are not limited to, RAM, ROM, electrically erasable program read-only memory (EEPROM), flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by computing device 216. Any such computer storage media can be part of computing device 216.

It should be understood that the various techniques described herein can be implemented in connection with hardware or software or, where appropriate, with a combination thereof. Thus, the methods, systems, and associated signal processing of the presently disclosed subject matter, or certain aspects or portions thereof, can take the form of program code (i.e., instructions) embodied in tangible media, such as floppy diskettes, CD-ROMs, hard drives, or any other machine-readable storage medium wherein, when the program code is loaded into and executed by a machine, such as a computing device, the machine becomes an apparatus for practicing the presently disclosed subject matter. In the case of program code execution on programmable computers, the computing device generally includes a processor, a storage medium readable by the processor (including volatile and non-volatile memory and/or storage elements), at least one input device, and at least one output device. One or more programs can implement or utilize the processes described in connection with the presently disclosed subject matter, e.g., through the use of an application programming interface (API), reusable controls, or the like. Such programs can be implemented in a high level procedural or object-oriented programming language to communicate with a computer system. However, the program(s) can be implemented in assembly or machine language, if desired. In any case, the language can be a compiled or interpreted language and it may be combined with hardware implementations.

In certain examples, system memory 220 comprises computer-executable instructions stored thereon that, when executed by the processor 218, cause the processor 218 to receive an electromagnetic signal from the instrument 208, process the electromagnetic signal to obtain a characteristic of the particle; and output the characteristic of the particle. The electromagnetic signal can, for example, comprise color, intensity, brightness, absorbance, scattering, fluorescence, frequency, wavelength, or a combination thereof.

The analysis of signals captured by the instrument can be carried out in whole or in part on one or more computing device. For example, the system may comprise one or more additional computing device.

In some examples, the second arm of the channel 114 further comprises a collection region 126 such that the second arm of the confinement region further comprises a collection region; wherein applying a fourth DC voltage to the second DC electrode to translocate the droplet to the collection region of the second arm of the confinement region; and wherein turning off the AC voltage to at least the second pair of AC electrodes 112 causes the droplet to fall into the collection region 126 of the second arm of the channel 114.

In some examples, the third arm of the channel 120 further comprises a collection region 128 such that third arm of the confinement region further comprises a collection region; wherein applying a fourth DC voltage to the third DC electrode 122 translocates the droplet to the collection region of the third arm of the confinement region; and wherein turning off the AC voltage to at least the third pair of AC electrodes 118 causes the droplet to fall into the collection region 128 of third arm of the channel 120.

In some examples of the systems 200, the second arm of the confinement region further comprises second detection region; and the device 100 further comprises: a fourth pair of alternating current (AC) electrodes 130 disposed on the surface 104 of the insulating substrate 102, wherein each of the AC electrodes comprising the fourth pair of AC electrodes 130 is spaced apart on the surface 104 of the insulating substrate 102 such that the fourth pair of AC electrodes 130 define a fourth arm of a channel 132, and wherein the fourth pair of AC electrodes 130 is electrically connected to the AC voltage source 202; a fourth direct current (DC) electrode disposed on the surface 104 of the insulating substrate 102 and interspersed within the fourth arm of the channel 132, wherein the fourth DC electrode is electrically connected to the DC voltage source 206; a fifth pair of alternating current (AC) electrodes 136 disposed on the surface 104 of the insulating substrate 102, wherein each of the AC electrodes comprising the fifth pair of AC electrodes 136 is spaced apart on the surface 104 of the insulating substrate 102 such that the fifth pair of AC electrodes 136 define a fifth arm of a channel 138, and wherein the fifth pair of AC electrodes 136 is electrically connected to the AC voltage source 202; and a fifth direct current (DC) electrode 140 disposed on the surface 104 of the insulating substrate 102 and interspersed within the fifth arm of the channel 138, wherein the fifth DC electrode 140 is electrically connected to the DC voltage source 206; wherein the second 114, fourth 132, and fifth 138 arms of the channel intersect at a second junction 142; such that the confinement region further comprises: a fourth arm and a fifth arm, wherein the second, fourth, and fifth arms of the confinement region intersect at a second junction.

In some examples, applying a fourth DC voltage to the second DC electrode 116 translocates the droplet to the second detection region; and the system 200 further comprises a second instrument configured to determine a second characteristic of the particle in the droplet at the second detection region; wherein applying a fifth DC voltage to the second DC electrode 116 translocates the droplet from the second detection region to the second junction of the confinement region; and wherein applying a sixth DC voltage to the second DC electrode 116, the fourth DC electrode, the fifth DC electrode 140, or a combination thereof translocates the droplet from the second junction of the confinement region to the fourth arm of the confinement region or the fifth arm of the confinement region based on the second characteristic of the particle, thereby sorting the droplet based on the second characteristic of the particle.

In some examples, the system 200 can further comprise a second light source configured to illuminate the droplet in the second detection region. The system 200 can further comprise, for example, a second lens. In some examples, the system 200 is aligned such that the second light source is below the second lens and the second instrument is above the second lens.

In some examples, the system 200 further comprises a second mirror. The system 200 can, for example, be aligned such that the second light source is configured to illuminate the second mirror and the second mirror is configured to reflect the electromagnetic radiation from the second light source to illuminate the droplet in the second detection region.

In some examples, the system 200 further comprises a second computing device comprising a processor and a memory operably coupled to the processor, the memory having further computer-executable instructions stored thereon that, when executed by the processor, cause the processor to: receive an electromagnetic signal from the second instrument; process the electromagnetic signal to obtain a second characteristic of the particle; and output the second characteristic of the particle.

In some examples, the fourth arm of the channel 132 further comprises a collection region 144 such that the fourth arm of the confinement region further comprises a collection region; and wherein applying a seventh DC voltage to the fourth DC electrode translocates the droplet to the collection region of the fourth arm of the confinement region; and wherein turning off the AC voltage to at least the fourth pair of AC electrodes 130 causes the droplet to fall into the collection region 144 of the fourth arm of the channel 132.

In some examples, the fifth arm of the channel 138 further comprises a collection region 146 such that fifth arm of the confinement region further comprises a collection region; and wherein applying a seventh DC voltage to the fifth DC electrode 140 translocates the droplet to the collection region of the fifth arm of the confinement region; and wherein turning off the AC voltage to at least the fifth pair of AC electrodes 136 causes the droplet to fall into the collection region 146 of the fifth arm of the channel 138.

In some examples, the third arm of the confinement region further comprises third detection region; and the device 100 further comprises: a sixth pair of alternating current (AC) electrodes 148 disposed on the surface 104 of the insulating substrate 102, wherein each of the AC electrodes comprising the sixth pair of AC electrodes 148 is spaced apart on the surface 104 of the insulating substrate 102 such that the sixth pair of AC electrodes 148 define a sixth arm of a channel 150, and wherein the sixth pair of AC electrodes 148 is electrically connected to the AC voltage source 202; a sixth direct current (DC) electrode disposed on the surface 104 of the insulating substrate 102 and interspersed within the sixth arm of the channel 150, wherein the sixth DC electrode is electrically connected to the DC voltage source 206; a seventh pair of alternating current (AC) electrodes 154 disposed on the surface 104 of the insulating substrate 102, wherein each of the AC electrodes comprising the seventh pair of AC electrodes 154 is spaced apart on the surface 104 of the insulating substrate 102 such that the seventh pair of AC electrodes 154 define a seventh arm of a channel 156, and wherein the seventh pair of AC electrodes 154 is electrically connected to the AC voltage source 202; and a seventh direct current (DC) electrode disposed on the surface 104 of the insulating substrate 102 and interspersed within the seventh arm of the channel 156, wherein the seventh DC electrode is electrically connected to the DC voltage source 206; wherein the third arm of the channel 120, the sixth arm of the channel 150, and the seventh arm of the channel 156 intersect at a third junction 160; such that the confinement region further comprises: a sixth arm and a seventh arm, wherein the third, sixth, and seventh arms of the confinement region intersect at a third junction.

In some examples, applying an eighth DC voltage to the third DC electrode 122 translocates the droplet to the third detection region; and the system 200 further comprises a third instrument configured to determine a third characteristic of the particle in the droplet at the third detection region; wherein applying a ninth DC voltage to the third DC electrode translocates the droplet from the third detection region to the third junction of the confinement region; and wherein applying a tenth DC voltage to the third DC electrode 122, the sixth DC electrode, the seventh DC electrode, or a combination thereof translocates the droplet from the third junction of the confinement region to the sixth arm of the confinement region or the seventh arm of the confinement region based on the third characteristic of the particle, thereby sorting the droplet based on the third characteristic of the particle.

In some examples, the system 200 further comprises a third light source configured to illuminate the droplet in the third detection region. In some examples, the system 200 further comprises a third lens. The system 200 can, for example, be aligned such that the third light source is below the third lens and the third instrument is above the third lens.

In some examples, the system 200 can further comprise a third mirror. The system 200 can, for example, be aligned such that the third light source is configured to illuminate the third mirror and the third mirror is configured to reflect the electromagnetic radiation from the third light source to illuminate the droplet in the third detection region.

In some examples, the system 200 can further comprise a third computing device comprising a processor and a memory operably coupled to the processor, the memory having further computer-executable instructions stored thereon that, when executed by the processor, cause the processor to: receive an electromagnetic signal from the third instrument; process the electromagnetic signal to obtain a second characteristic of the particle; and output the second characteristic of the particle.

In some examples, the sixth arm of the channel 150 further comprises a collection region 162 such that the sixth arm of the confinement region further comprises a collection region; and wherein applying an eleventh DC voltage to the sixth DC electrode translocates the droplet to the collection region of the sixth arm of the confinement region; and wherein turning off the AC voltage to at least the sixth pair of AC electrodes 148 causes the droplet to fall into the collection region of the sixth arm of the channel 162.

In some examples, the seventh arm of the channel 156 further comprises a collection region 164 such that seventh arm of the confinement region further comprises a collection region; and wherein applying an eleventh DC voltage to the seventh DC electrode to translocate the droplet to the collection region of the seventh arm of the confinement region; and wherein turning off the AC voltage to at least the seventh pair of AC electrodes 154 causes the droplet to fall into the collection region of the seventh arm of the channel 164.

In some examples, the system can further comprise a means for translocating one or more components of the system.

A number of embodiments of the invention have been described. Nevertheless, it will be understood that various modifications may be made without departing from the spirit and scope of the invention. Accordingly, other embodiments are within the scope of the following claims.

The examples below are intended to further illustrate certain aspects of the systems and methods described herein, and are not intended to limit the scope of the claims.

EXAMPLES

The following examples are set forth below to illustrate the methods and results according to the disclosed subject matter. These examples are not intended to be inclusive of all aspects of the subject matter disclosed herein, but rather to illustrate representative methods and results. These examples are not intended to exclude equivalents and variations of the present invention which are apparent to one skilled in the art.

Efforts have been made to ensure accuracy with respect to numbers (e.g., amounts, temperature, etc.) but some errors and deviations should be accounted for. Unless indicated otherwise, parts are parts by weight, temperature is in ° C. or is at ambient temperature, and pressure is at or near atmospheric. There are numerous variations and combinations of measurement conditions, e.g., component concentrations, temperatures, pressures and other measurement ranges and conditions that can be used to optimize the described process.

Example 1

Since its inception over forty years ago, fluorescence activated cell sorting (FACS) has been the leading technology for sorting individual cells. Cells are prepared with either internal or external fluorescent tags that indicate the presence of a molecule or function of interest. FACS relies on the use of flow cytometry, where the distance between cells in solution is large compared to their size, by suspending cells in an aqueous sheath fluid solution and forming single-cell droplets. Fluorescent labeling is observed using laser excitation with the range of detectable colors limited by the system lasers and filters. Positively stained cells, with fluorescence intensity greater than a predetermined threshold, are tagged with an electrostatic charge. Downstream, this charge directs cells towards either a collection or discard vessel. Aside from fluorescence, additional morphological information can be determined using light scattering, including relative size information and cell granularity. Sorting speeds vary based on system settings and normal sorts are in the range of 1,000-10,000 cells/second with high purity. For example, devices can sort $10^7$ samples per second but merging and resorting reduce the speed to less than $10^3$ samples per second, as further sorting requires reloading the sample into the device. Cells are sensitive to the jet pressure required to form single-cell suspensions, and the increase in pressure required to raise these sorting rates can greatly decrease cell viability. While it is the most commonly used technology, traditional FACS is not without limitations, including high cost (several hundred thousand dollars) and operational complexities that require specialized operation and maintenance. Though multiple fluorescence tags can be used to create a highly selective population, only one such population can be isolated in a given sort.

Described herein is a new tool for cell analysis, including single cell analysis, based on surface electrode ion traps. Cells are contained in charged droplets of solution and levitated above the trap surface by electromagnetic fields. Cells can be sorted by optical, chemical, and/or physical properties. In contrast to single stream devices, the surface electrode trap allows the cells to be sorted multiple times using multiple tests within the same chip. This is similar to microfluidic systems.

The surface electrode trap cell sorter offers the benefits of the microfluidic chip while overcoming some of its drawbacks. The systems and methods described herein do not suffer from surface contamination or cell aggregation, as the cells float above the surface in charged droplets trapped by oscillating electric fields. Since the cells levitate above the surface, disposable chambers are not necessary, unlike in current microfluidic devices.

The traps are defined by the application of RF electrode voltages and then DC electrode voltages can be used to transport the droplets over distances and through junctions that can be used for sorting. The speed of the cells and the position of the droplets are controlled by electric fields allowing the cell stream to be manipulated at the rate appropriate for the detection method without fear of cell aggregation seen in microfluidics. Furthermore, the technology allows controlled merging of droplets allowing the addition of chemicals and nutrients to the environment of the cells one cell at a time.

Cells can be categorized by a variety of optical methods. Rapid categorization is performed by labeling with fluorescent markers. Label-free methods are used to categorize the cells on a longer time scale, such as light scattering to determine cell size and auto-fluorescence spectroscopy to characterize cell type. The long hold times and cell separation allows for characterization of single cell spectra by absorption, fluorescence, or Raman techniques.

The surface electrode traps can be made at a range of length scales using modern lithography techniques or standard printed circuit boards. The systems and methods described herein can hold cells within charged droplets above printed circuit board surface electrode ion traps and discriminate cells based on fluorescence markers. The systems and methods described herein allow for faster sorting and on-the-fly droplet merging and splitting. These devices combine the specialization of microfluidics approaches with the speed of modern electronics, allowing for faster sorting speeds and improved cell viability relative to microfluidic devices.

Figure 12:
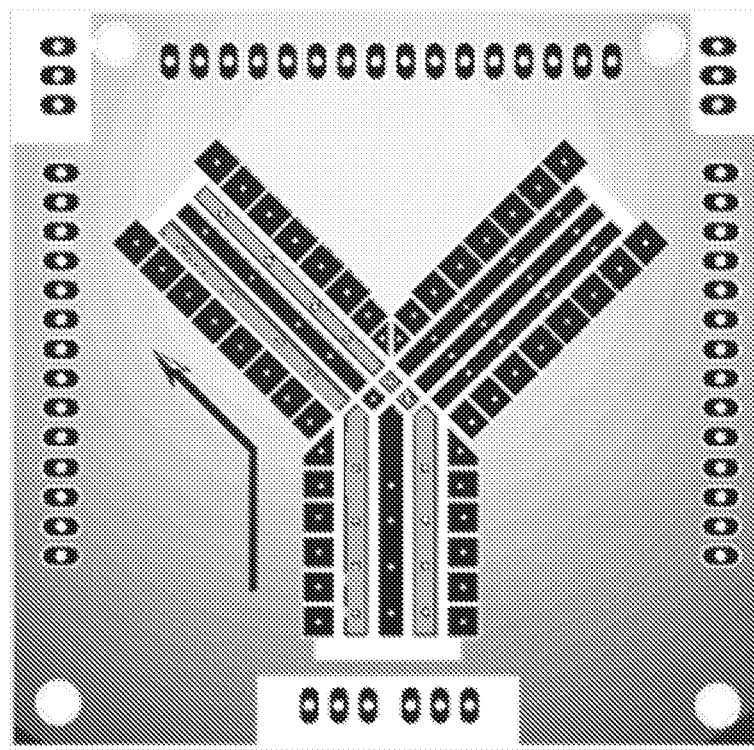
FIG. 12 shows an exemplary device with the electrodes configured to sort the cells along the left arm.
Figure 13:
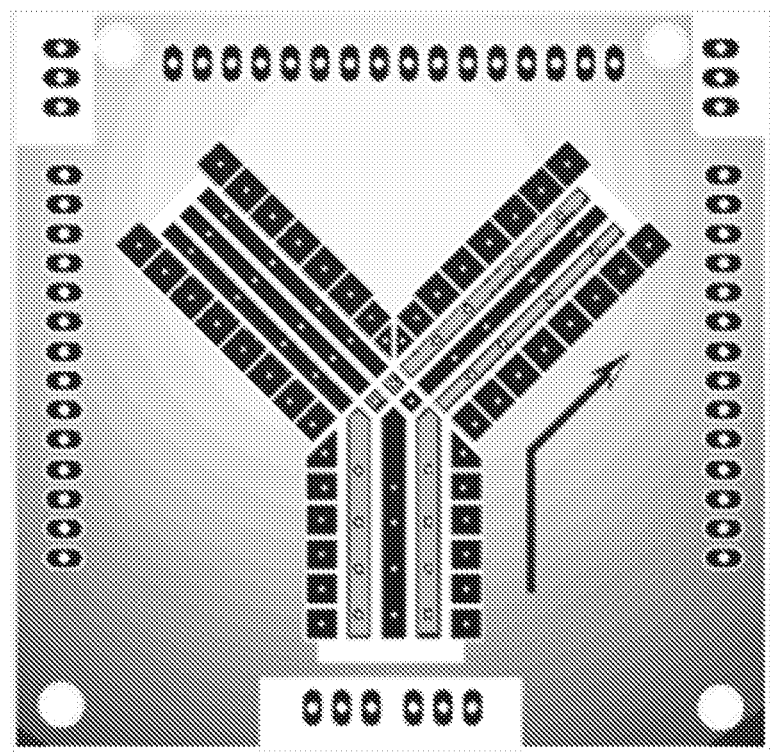
FIG. 13 shows an exemplary device with the electrodes configured to sort the cells along the right arm is shown.
Figure 14:
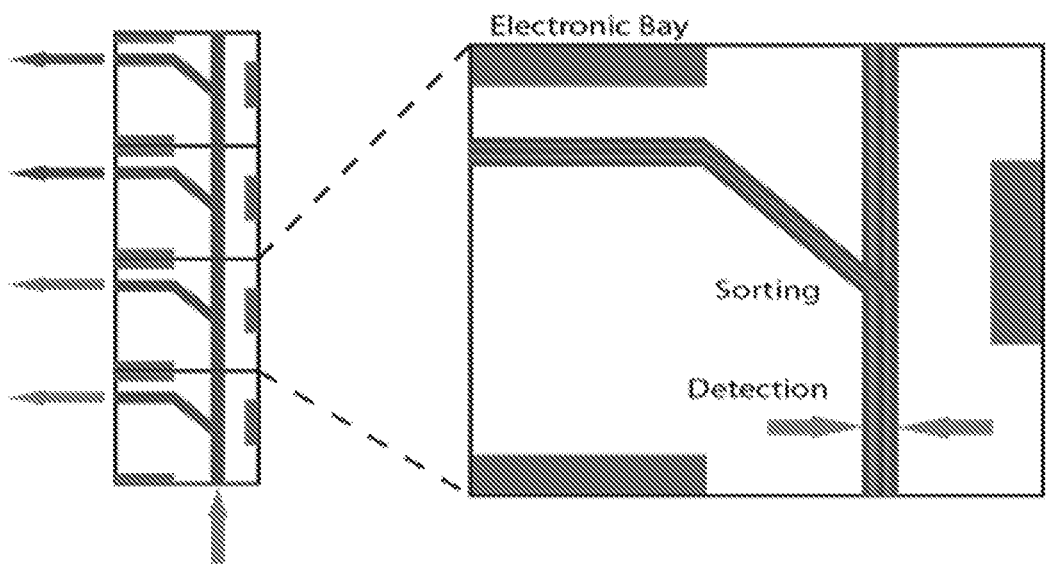
FIG. 14 shows a network of junctions that can be used for sorting cell mixtures into multiple species and phenotypes.

An exemplary device for these methods with the electrodes configured to sort the cells along the left arm is shown in FIG. 12. An exemplary device for these methods with the electrodes configured to sort the cells along the right arm is shown in FIG. 13. FIG. 14 shows a network of junctions that can be used for sorting cell mixtures into multiple species and phenotypes.

Cell sorting can be applied to a number of medical, industrial, agricultural or military applications. Cell sorters allow for the directed evolution of cells to increase the production of desired chemicals or pharmaceuticals. Cell sorters can also be used to explore microbial communities and gather more information about the relation between the microbiome and microbial populations.

Example 2

Figure 15:
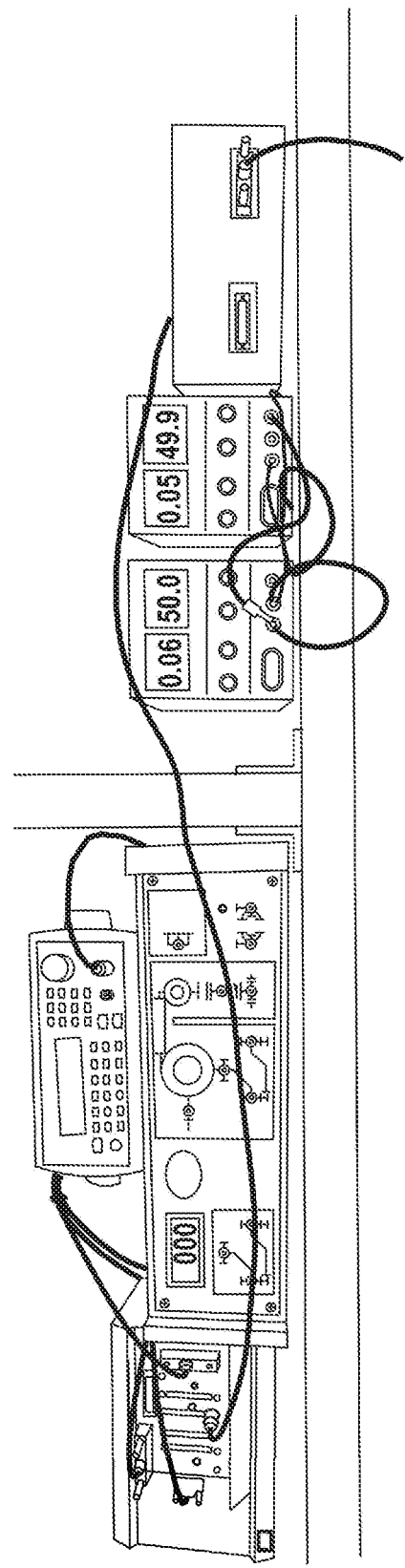
FIG. 15 shows the electronics used to drive an exemplary system.
Figure 16:
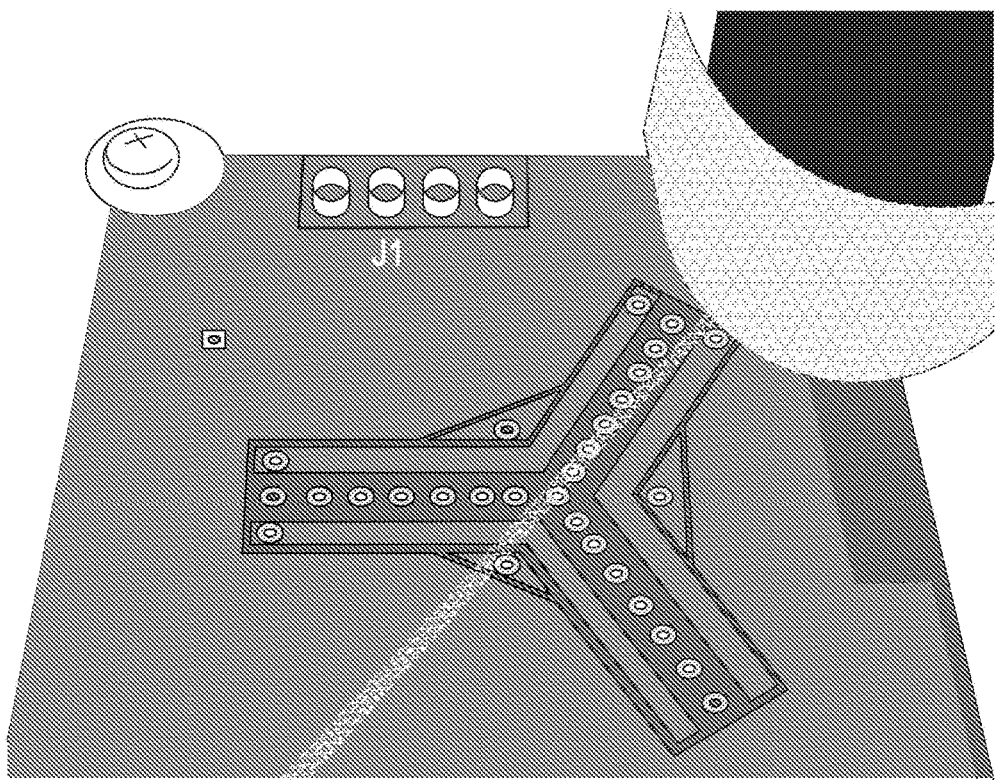
FIG. 16 shows an exemplary device and droplet generating device.
Figure 17:
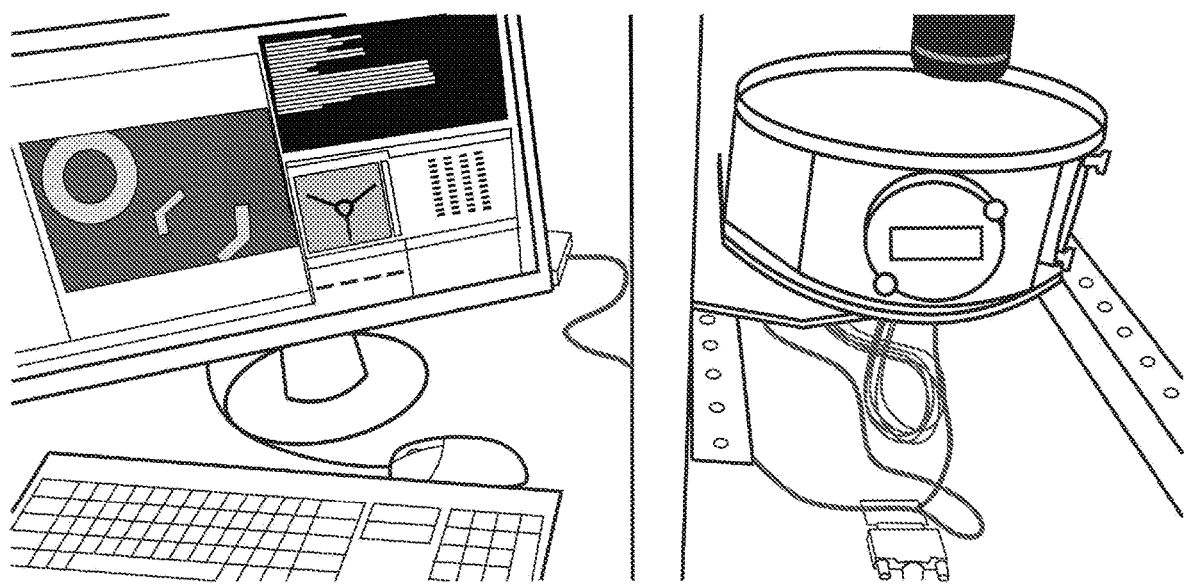
FIG. 17 shows an exemplary device and droplet generating device to the right, both of which housed in the metal chamber and controlled by the computer on the left using control software.

An exemplary system is shown in FIG. 15-17. The system is driven by off-the shelf table-top electronics (FIG. 15). The system can use standard compactly packaged electronics. The surface electrode ion trap fabricated from a printed circuit board (PCB) is shown in FIG. 16. The electrodes are coated with insulator to prevent shorting from any untrapped droplets. Droplets have been shuttled through the junction in a deterministic way. The copper mesh is a grounding shield for the droplet maker, which is a piezoelectric droplet device from Microfab. The droplet device and the waveforms for droplet motion on the trap are controlled by control software that interfaces with National Instruments DACs and Arduino controllers. The droplets are imaged by a camera and light is also collected by a photon multiplier tube (PMT) for fast analysis. FIG. 17 shows a desktop screen, which is displaying a camera image and the control software, next to the chamber housing the trap and the imaging optics. The chamber in FIG. 17 is large, but can be reduced to a few inches on a side. The chamber is held at constant humidity to reduce droplet evaporation. Droplet lifetimes have been measured to be greater than one hour.

Example 3

Figure 18:
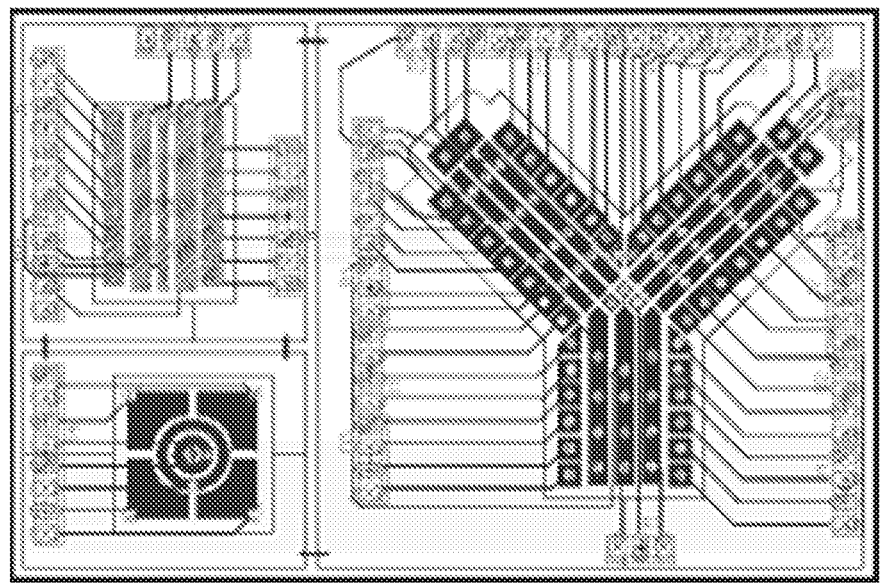
FIG. 18 shows an exemplary device.

An exemplary device is shown in FIG. 18. The device is a printed circuit board that was printed without a solder mask or a silkscreen. There are three trapping regions on this board. A ring trap region (bottom left), a linear region (upper left), and a y-trap (right).

Methods of operating the ring and linear regions will be discussed herein. The ring trap has a relatively high trap depth compared to the linear region because of its circular symmetry. The linear region does not have a trap depth as high as the circular region because of the DC electrode placement.

FIG. 18 shows the layout for the board. The board itself is connected to wires via headers soldered to the board. For the linear region, the wires on the headers go to a DB25 connector through a hole in the bottom of the chamber. Some of the wires to the connector can be cut because there were redundancies on the board. This connector holds all the DC electrodes for the linear region. The RF signal is connected via a separate wire from the connector and is directly connected inside of the chamber with an alligator clip. The ring trap region is connected to wires as well; these wires are not connected to a connected like the DB25, but instead are directly connected with alligator clips to ground or the RF signal.

The RF signal originates from a function generator and is set to a 300 Hz sine wave. The output of this signal goes to a high voltage amplifier. The amplifier is set to amplify the input signal 100×. The input and output connections are all on the back side of the amplifier. An output voltage monitor is also connected to the amplifier, the voltage of which is $\frac{1}{100}$ the voltage of the output, and is used as necessary as an output indicator.

There is a box with 48 analog output channels. This box is controlled using computer software. The computer software controls the output channels on the box. The software can, for example, be used to load a waveform file and send it to the channels on the box. Before use, the channels and the trap electrodes are aligned with a map file.

The output from the box is connected to a DB25 connector. Each μm of the connectors corresponds to an analog output channel at a maximum/minimum of ±10 volts. Pin number 7 on both cables is not connected to an output channel but instead is connected to ground on the first DB25 breakout board. The other end of the cable is connected to an aluminum amplifier box located to the right of the HV RF amplifier. This box contains a powered fan (standard wall connection) and the printed circuit board containing 25 channels input and output via DB25 connections. Each channel is amplified a more than 7 times via the board electronics.

The printed circuit board is powered by two external power supplies, which are wired so that one power supply supplied 45 V and the other power supply supplies −45 V to the printed circuit board. The 25 op amp chips on the board can draw a lot of current and thus give off heat. The board is cooled via the fan.

The amplified signals from the aluminum box amplifier are connected to another DB25 cable that runs to the table top underneath the chamber. The DB25 is connected to a filter board, which is used as short circuit protection. Each channel has a pair of diodes connected in opposite directions in series to ground. The diode chip was selected such that the short circuit protection only starts clamping the current down when it reaches about 50 V. This allows for the DC signal to get through but protects against the event of the HV RF signal somehow shorting to another electrode or to ground. The filter board is connected to a DB25 connector and thus to the trap electrode wires.

There are two lasers used for this experiment. One is a 532 μm diode laser (e.g., a green laser pointer diode), which is not temperature or current stabilized. There is a black 1" optical tube located at the trap height containing the laser diode and a small control circuit. The laser control board is connected to a small female barrel connector. There is an AC/DC adapter that plugs into the barrel connector and to the wall. The laser light that exits the 1" tube is directed to a mirror on a separate breadboard platform, but still at the same height. This mirror is used to direct the beam of light to the trap region in order to illuminate trapped particles.

The second laser is a 488 μm diode laser, which is setup on the table behind the chamber and the 80-20 aluminum supports. The light that comes out of the laser goes through a few mirrors before being fiber coupled into a single mode fiber. The output coupler is located on the same platform as the green diode, but is not aligned with the trap center.

The setup is imaged with a standard Canon Rebel DSLR camera with a custom lens set up. A commercial Canon camera lens is located closest to the trap surface and is the first of the optics to encounter the light from the trapped particle, as the camera lens minimizes aberration and distortion. The image from the particle travels through the commercial lens before reaching a commercial microscope objective. In between the microscope objective and the commercial lens is a sliding tube cover. This cover can be slid back for insertion of a filter, for example to visualize cell fluorescence. The objective gives further magnification while retaining image quality. The resulting image from the objective is then passed along the tube structure where it is redirected by a mirror to the CCD inside of the camera. Just before the CCD is a beam splitter that passes some of the collected light to a photodetector and some to the camera. The CCD is able to detect the color image of the cell fluorescence.

The camera is setup such that the CCD is focused on the trapping region of the ring trap. The surface of the trap can be seen a bright incoherent light is shone onto the surface. This minimizes the interference and allows for visualization of scattered light from the surface of the device. The camera can be translocated to image other areas of the printed circuit board. The camera can be angled relative to the vertical to image droplet loading.

The droplet generating device is an MJ-Al model Microfab droplet device with an opening diameter of 60 μm. This is a piezo-actuated droplet device; the piezo inside of the droplet generating device creates a pressure wave that ejects individual droplets. Before and during operation of the droplet generating device, the nozzle tip should be visually inspected under a microscope to determine if the nozzle is clogged.

The droplet generating device can be operated using a waveform. In some examples, the droplet generating device operating parameters are a 20 V peak, 3 μs rise time, and 20 μs dwell time. The control device for the droplet generating device can be used to continually eject droplets or to require user input to eject each droplet.

The control device for the droplet generating device is connected through designated pins to a BNC cable which goes to an external amplifier. The output from the amp goes to a BNC before being split into a separate ground and live wire. These wires are what is plugged into the connector for the piezo in the droplet device.

To use the device, the droplet generating device is backfilled with IPA. Next, the droplet generating device is backfilled with a solution. The nozzle of the droplet generating device is then visually inspected under a microscope to ensure the nozzle is not clogged. If the nozzle is not clogged, the droplet generating device is ready for use and is filled with the sample solution. If the nozzle is clogged, the droplet generating device is backfilled with a 2% Hellmanex solution. If the nozzle remains clogged, the droplet generating device is backfilled with a 2% Hellmanex solution and placed in a sonicator for 10-20 seconds.

For ejecting a charged droplet, −300 to −700 V is applied to the washer at the end of the device holder to charge the ejected droplet. For trapping preparation, the droplet generating device is inserted into the 3D printed case. The end of the droplet generating device should be visible from the opening where the washer is, but not so close to the printed circuit board that it allows a short. The case of the droplet generating device is grounded, but the washer is held at a high negative voltage. The washer is soldered to a wire that is connected to alligator clips. The clips are fed through a hole in the chamber bottom to the high voltage signal. The signal is supplied by a HV box using a HV ground and a live HV wire.

To being an experiment, turn on the necessary laser(s) and other equipment, prepare the piezo waveform, load the droplet device, place the droplet device inside the chamber, turn on the HV RF, turn on the DC electrodes (if needed) and prepare the waveform (if needed), turn on the fan (if needed), turn on the ionization HV (if needed), turn on the camera, open all software, eject a droplet, insert a filter in the light path (if needed) to visualize fluorescence (if desired), and observe the droplet using the camera.

Example 4

The devices described herein comprise three basic function blocks: AC electrodes, DC electrodes, and junction(s). High AC voltage (~1 kV, 200-400 Hz) is delivered to the AC electrodes to form the trapping field confining the charged particles in the radial dimension (X-Y plane in FIG. 19). All the RF electrodes are connected and operated at the same voltage and frequency.

Figure 19:
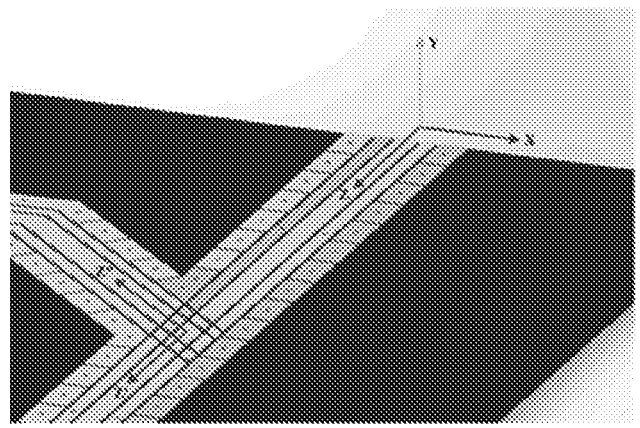
FIG. 19 shows the reference axes for a surface electrode trap.

Medium DC voltages (~45 to 45 V) are delivered to the DC electrode to confine the charged particle in the axial dimension (Z axis in FIG. 19). Different voltages are added to different DC electrodes at the different times to move the charged particles adiabatically. These time sequence of the voltages can be referred to as "waveforms."

At the junction(s), a single Z axis splits into two Z axes (Z', Z") pointing in different directions (FIG. 19). The charged particles are routed to different paths from the junction(s).

The minimal dimension of the traps are based on the minimal feature sizes of commercial printed circuit board manufacturers. In some designed, the minimal gap/wire width was selected to be >6 mil (1 mil=0.001 inch) and the minimal vertical interconnect access (VIA) size was selected to be >13 mil.

Figure 20:
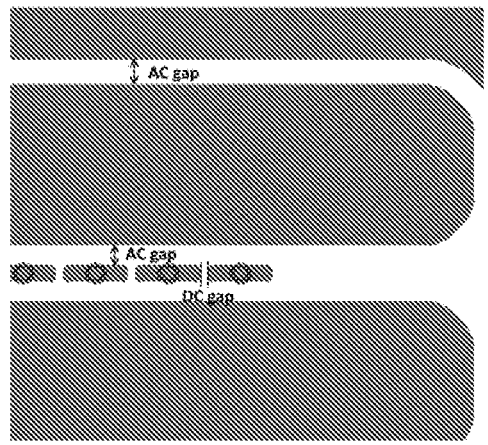
FIG. 20 shows a schematic of the AC gap and DC gap.

The AC electrode gap (FIG. 20) must be big enough to avoid breaking down in both dry and wet conditions. Under dry conditions, the minimal AC electrode gap size will stand the maximum operational voltage (~1000 V). Under wet conditions, e.g. where droplets accidently contact the trap surface, break down happens when the droplets cover the AC gaps. Therefore, under wet conditions, the AC electrode cap size should be much larger than the droplet's diameter. The droplets used in this example have a diameter of ~3 mil.

The DC electrode gap (FIG. 20) must be big enough to avoid breaking down in both dry and wet conditions. The DC electrodes have a much lower voltages than the AC electrodes, and the minimal DC electrode gap will survive both dry and wet situations.

In some designs, there was an exposed copper layer present in the device, mainly VIAs, which can cause a low breaking down voltage in the wet situation. Accordingly, some trap designs included a solder mask that covered all the copper.

Figure 21:
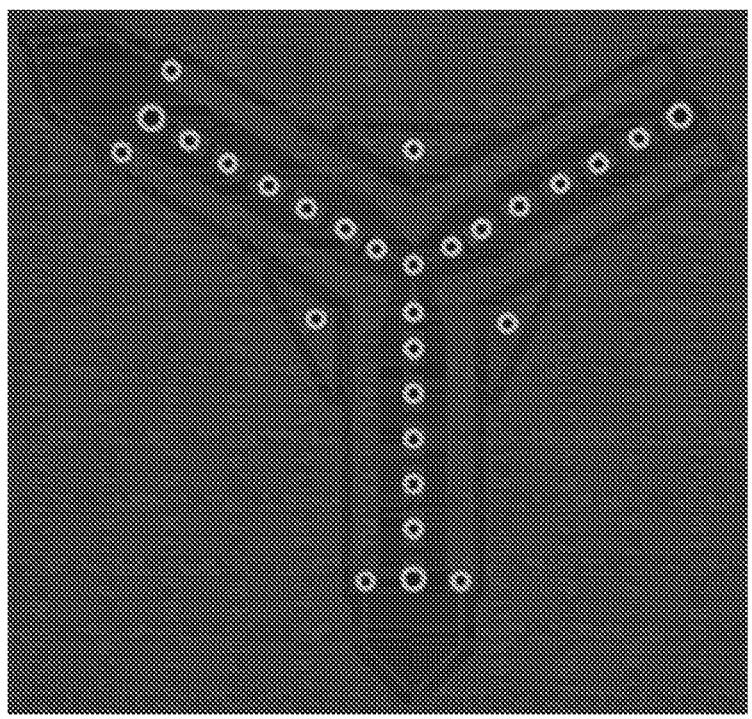
FIG. 21 shows an example trap with large AC and DC gaps, the VIA copper layer being directly exposed, and short arms with 24 DC electrodes mapped to one DB-25 connector.
Figure 22:
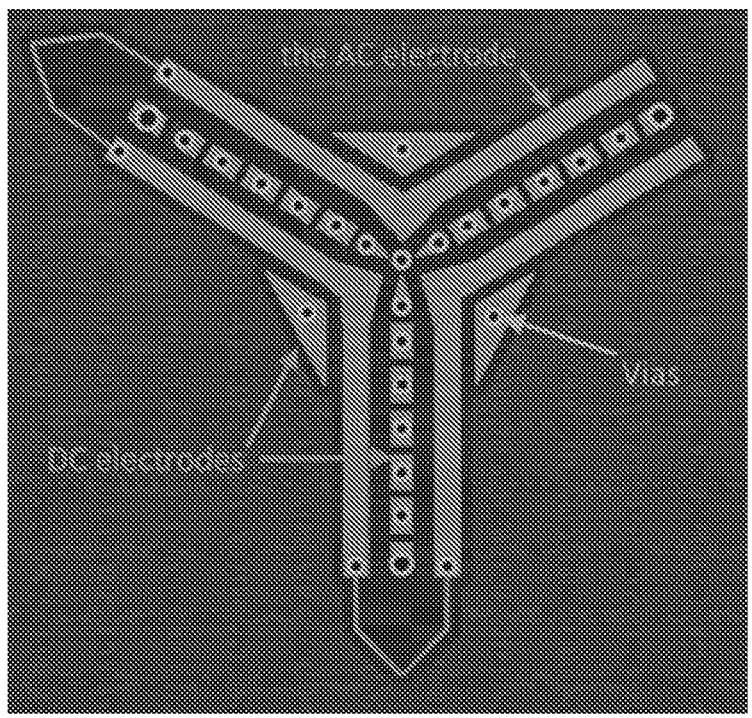
FIG. 22 shows the example trap in FIG. 21 with the various components indicated with shading.

An example trap with large AC and DC gaps (1270 µm and 508 µm, respectively), the VIA copper layer being directly exposed, and short arms with 24 DC electrodes mapped to one DB-25 connector is shown in FIG. 21 and FIG. 22. Each DC electrode in this trap had dimensions of 2.032 millimeters (mm)×1.270 mm.

Figure 23:
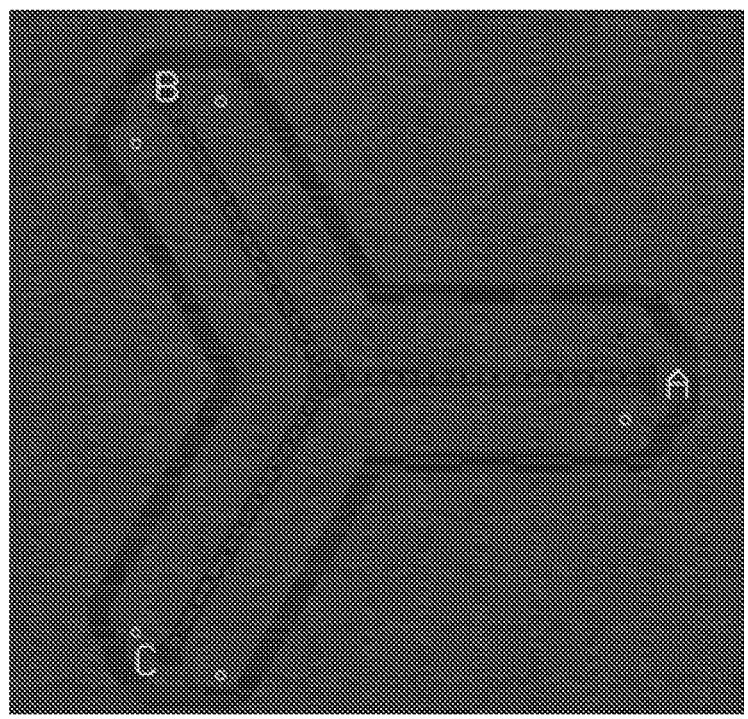
FIG. 23 shows an example trap with small AC and DC gaps (same size), no exposed copper layer, no sharp corner, larger aspect ratio for DC electrodes, and 24 DC electrodes mapped to one DB-25 connector.
Figure 24:
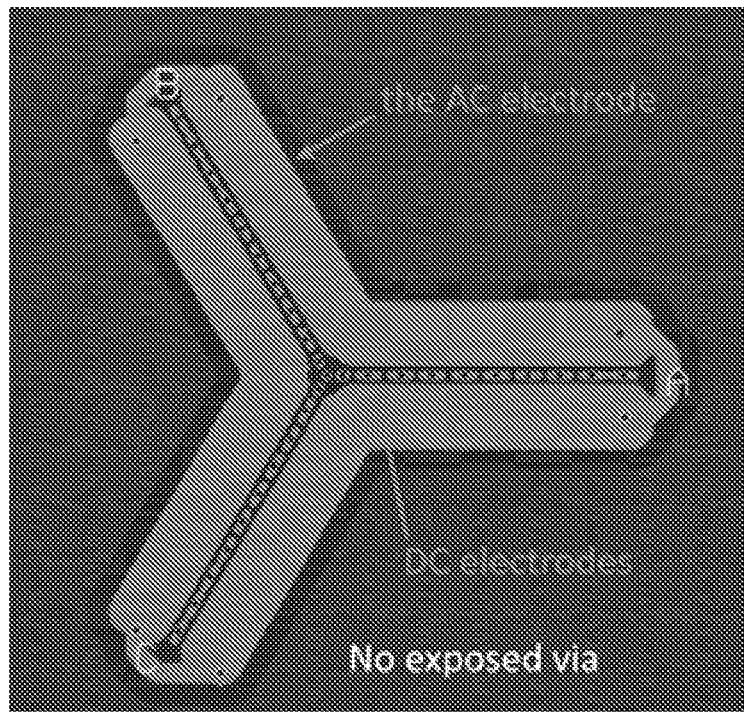
FIG. 24 shows the example trap in FIG. 23 with the various components indicated with shading.

An example trap with small AC and DC gaps (same size, both 381 µm), no exposed copper layer, no sharp corner, larger aspect ratio for DC electrodes, and 24 DC electrodes mapped to one DB-25 connector is shown in FIG. 23 and FIG. 24. Each DC electrode in this trap had dimensions of 1.524 mm×0.381 mm.

Figure 25:
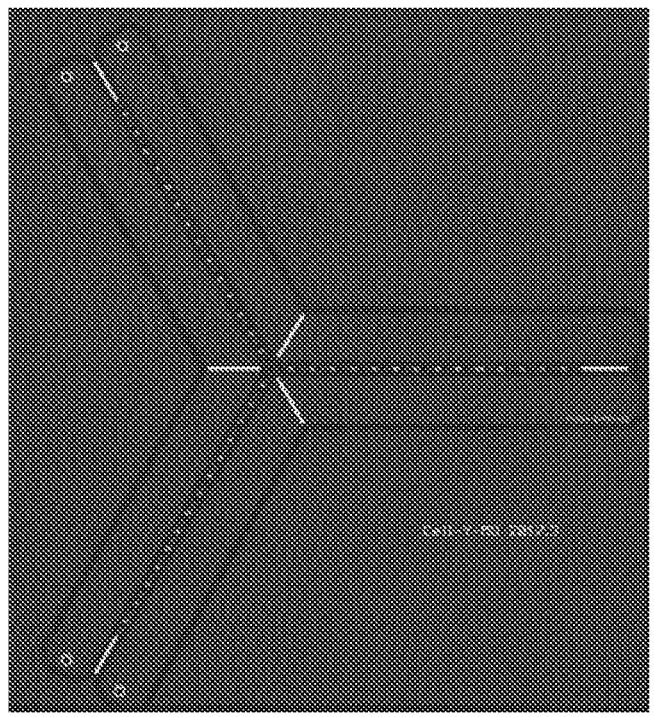
FIG. 25 shows an example trap with larger AC gaps and smaller DC gaps, no exposed copper layer, larger aspect ratio for DC electrodes, no sharp corners, 42 electrodes mapped to one DB-25 connector where DC pins are re-used to support large number of electrodes with the same connector/DAC channels, long arms for optical access, and marks on trap surface for precision alignment.
Figure 26:
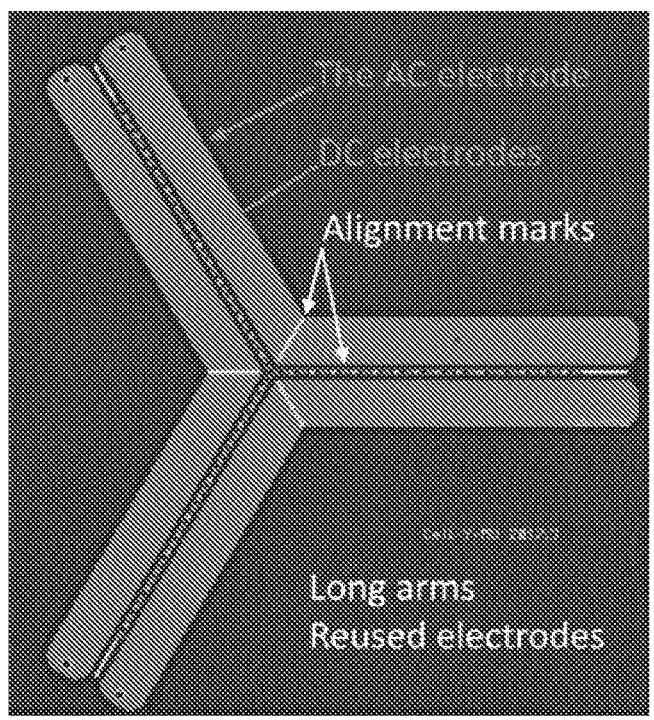
FIG. 26 shows the example trap in FIG. 25 with the various components indicated with shading.

An example trap with larger AC gaps and smaller DC gaps relative to the device in FIG. 23 and FIG. 24 (476 µm and 190 µm, respectively), no exposed copper layer, larger aspect ratio for DC electrodes, no sharp corners, 42 electrodes mapped to one DB-25 connector where DC pins are re-used to support large number of electrodes with the same connector/DAC channels, long arms for optical access, and marks on trap surface for precision alignment is shown in FIG. 25 and FIG. 26. Each DC electrode in this trap had dimensions of 1.524 mm×0.381.

Figure 27:
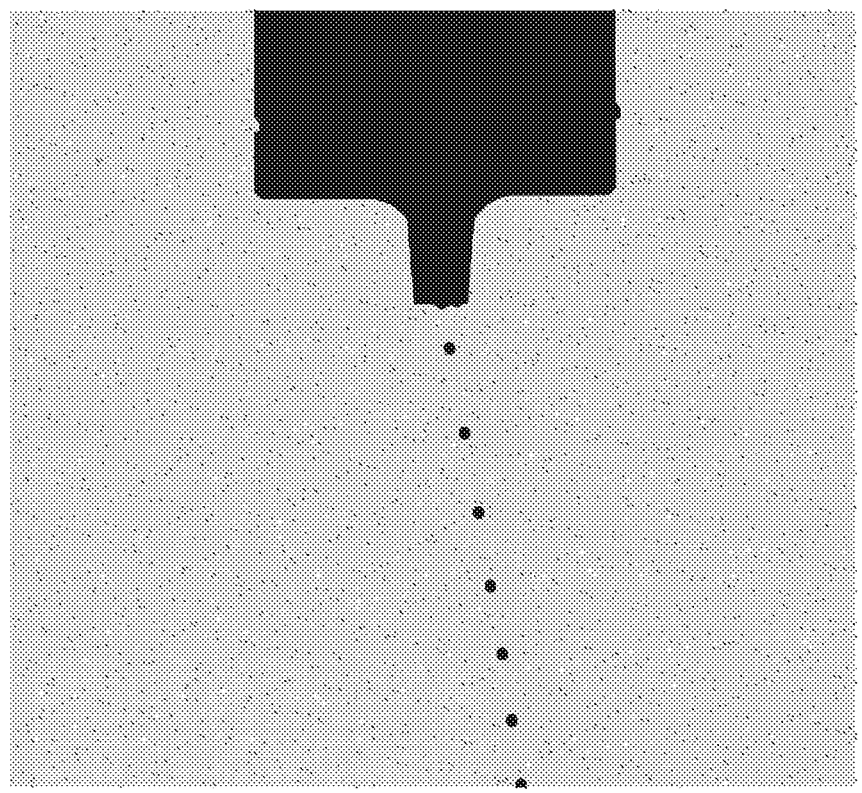
FIG. 27 shows droplets being generated and ejected from the droplet generating device.
Figure 28:
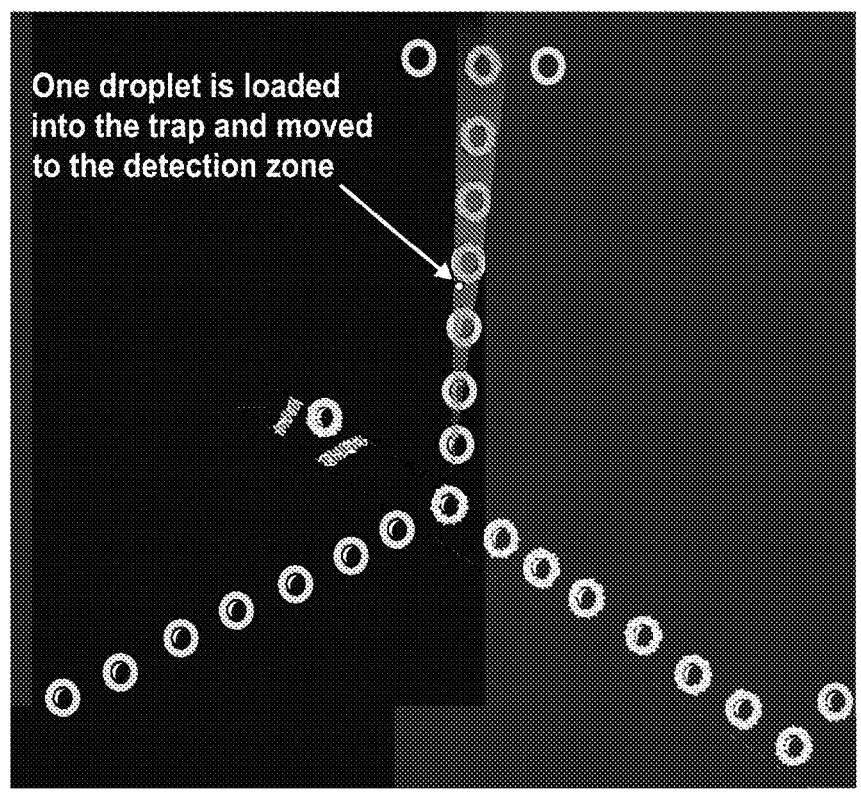
FIG. 28 shows a droplet loaded into the device that has been moved to the detection zone.
Figure 29:
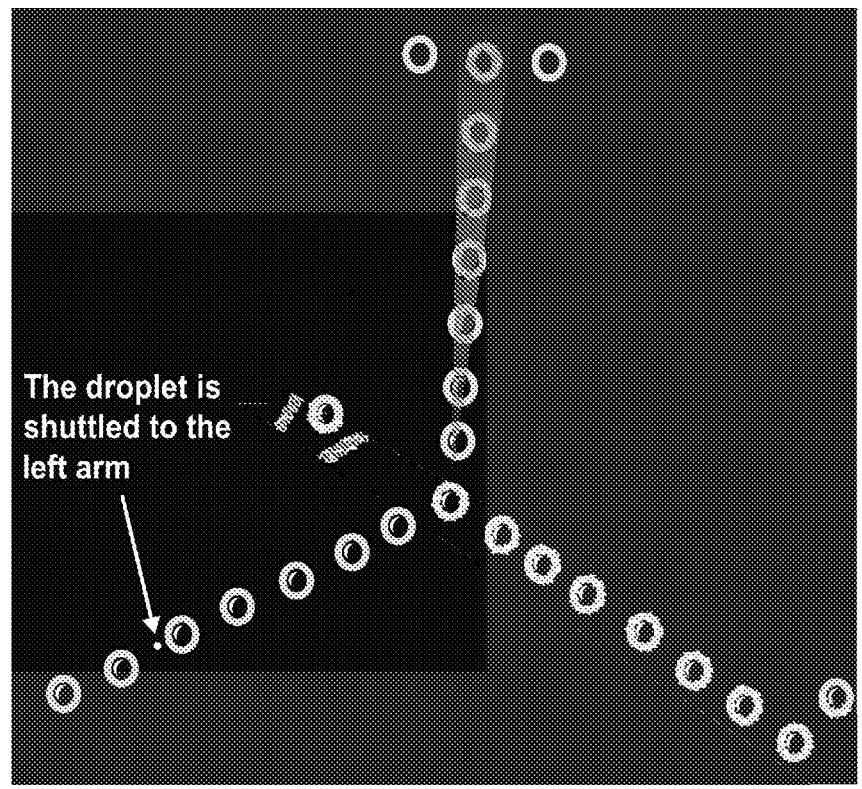
FIG. 29 shows a droplet that has been sorted into the left arm of the device.
Figure 30:
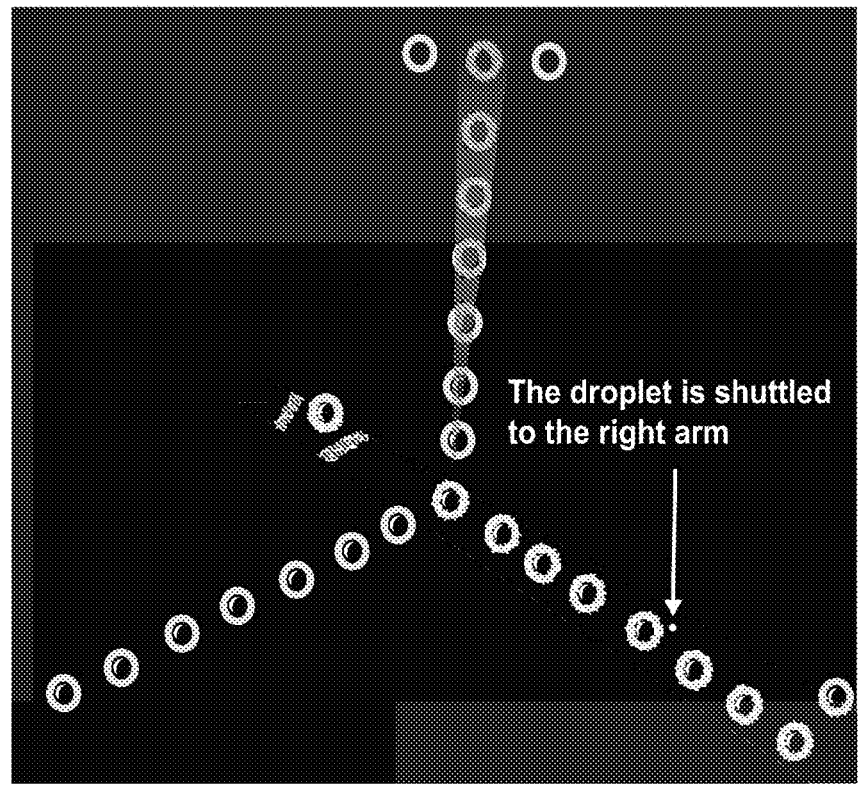
FIG. 30 shows a droplet that has been sorted into the right arm of the device.

To operate the device, droplets are generated one by one from a Micro-fab MJ-AL-00-060-DLC jetting device (FIG. 27). The droplets have a diameter of 60 µm. The droplet is charged up by a plate biased at −400 V. The droplets fall to the trap and get caught up by the AC and DC fields. The droplets float ~1 mm above the trap surface. A DC waveform moves the droplets out of the loading zone in to the detecting zone, and exposes the droplets to the laser radiation (FIG. 28). A PMT collects the scattered light from the droplet in the detection zone, and chooses one of the two waveforms according to a pre-set threshold with each waveform corresponding to one arm branching from the junction. The droplet is moved to one arm or the other corresponding to the PMT counts (FIG. 29 and FIG. 30). The AC field is turned off briefly to allow the droplet to fall to the collector. The steps can then be repeated on a second droplet.

Other advantages which are obvious and which are inherent to the invention will be evident to one skilled in the art. It will be understood that certain features and sub-combinations are of utility and may be employed without reference to other features and sub-combinations. This is contemplated by and is within the scope of the claims. Since many possible embodiments may be made of the invention without departing from the scope thereof, it is to be understood that all matter herein set forth or shown in the accompanying drawings is to be interpreted as illustrative and not in a limiting sense.

The methods of the appended claims are not limited in scope by the specific methods described herein, which are intended as illustrations of a few aspects of the claims and any methods that are functionally equivalent are intended to fall within the scope of the claims. Various modifications of the methods in addition to those shown and described herein are intended to fall within the scope of the appended claims. Further, while only certain representative method steps disclosed herein are specifically described, other combinations of the method steps also are intended to fall within the scope of the appended claims, even if not specifically recited. Thus, a combination of steps, elements, components, or constituents may be explicitly mentioned herein or less, however, other combinations of steps, elements, components, and constituents are included, even though not explicitly stated.

What is claimed is:

1. A method of sorting a particle based on a characteristic of the particle, the method comprising:
   providing a device comprising:
   an insulating substrate having a surface;
   a first pair of alternating current (AC) electrodes disposed on the surface of the insulating substrate, wherein each of the AC electrodes comprising the first pair of AC electrodes is spaced apart on the surface of the insulating substrate such that the first pair of AC electrodes define a first arm of a channel, and wherein each of AC electrodes comprising the first pair of AC electrodes is electrically connected to an AC voltage source;
   a first direct current (DC) electrode disposed on the surface of the insulating substrate and interspersed within the first arm of the channel, wherein the first DC electrode is electrically connected to a DC voltage source;
   a second pair of alternating current (AC) electrodes disposed on the surface of the insulating substrate, wherein each of the AC electrodes comprising the second pair of AC electrodes is spaced apart on the surface of the insulating substrate such that the second pair of AC electrodes define a second arm of a channel, and wherein each of AC electrodes comprising the second pair of AC electrodes is electrically connected to an AC voltage source;
   a second direct current (DC) electrode disposed on the surface of the insulating substrate and interspersed within the second arm of the channel, wherein the second DC electrode is electrically connected to a DC voltage source;
   a third pair of alternating current (AC) electrodes disposed on the surface of the insulating substrate, wherein each of the AC electrodes comprising the third pair of AC electrodes is spaced apart on the surface of the insulating substrate such that the third pair of AC electrodes define a third arm of a channel, and wherein each of AC electrodes comprising the third pair of AC electrodes is electrically connected to an AC voltage source;

a third direct current (DC) electrode disposed on the surface of the insulating substrate and interspersed within the third arm of the channel, wherein the third DC electrode is electrically connected to a DC voltage source;

wherein the first, second, and third arms of the channel intersect at a junction; and wherein the length of the first arm of the channel, the second arm of the channel, the third arm of the channel, or a combination thereof is from 10 millimeters (mm) to 100 mm;

applying AC voltage to the first pair of AC electrodes, the second pair of AC electrodes, and the third pair of AC electrodes thereby generating an electromagnetic trapping field defining a confinement region, wherein the confinement region is proximate the channel and above the surface of the insulating substrate;

wherein the confinement region comprises:
a first arm, a second arm, and a third arm, and wherein the first, second, and third arms of the confinement region intersect at a junction; and
wherein the first arm of the confinement region comprises a loading region and a detection region;

injecting a droplet having a surface charge into the loading region, wherein the electromagnetic trapping field traps the droplet in the confinement region such that the droplet levitates above the surface of the insulating substrate, wherein the droplet comprises a liquid sample comprising a particle;

applying a first DC voltage to the first DC electrode to translocate the droplet from the loading region to the detection region;

determining a characteristic of the particle in the droplet at the detection region;

applying a second DC voltage to the first DC electrode to translocate the droplet from the detection region to the junction of the confinement region; and applying a third DC voltage to the first DC electrode, the second DC electrode, the third DC electrode, or a combination thereof to translocate the droplet from the junction of the confinement region to the second arm of the confinement region or the third arm of the confinement region based on the characteristic of the particle, thereby sorting the droplet based on the characteristic of the particle.

2. The method of claim 1, wherein the AC voltage applied to the first pair of AC electrodes, the second pair of AC electrodes, the third pair of AC electrodes, or a combination thereof has a peak-to-peak voltage of from 100 V to 1200 V and a frequency of from 50 Hertz (Hz) to 1000 Hz.

3. The method of claim 1, wherein the droplet comprises from 1 to 1000 particles.

4. The method of claim 1, wherein the particle has an average particle size of from 1 nm to 10 um.

5. The method of claim 1, wherein the particle comprises a polymer particle, a metal particle, a semiconductor particle, a biological cell, or a combination thereof.

6. The method of claim 5, wherein the biological cell is not damaged during the method.

7. The method of claim 1, wherein the first DC voltage, the second DC voltage, the third DC voltage, or a combination thereof is from −75 V to 75 V.

8. The method of claim 1, wherein the characteristic of the particle comprises the presence, absence, or intensity of absorbance; the presence, absence, or intensity of scattering; the presence, absence, or intensity of fluorescence; the size of the particle; the number of particles in the droplet; or a combination thereof.

9. The method of claim 1, wherein a second droplet is injected into the loading region and the method is repeated for the second droplet.

10. The method of claim 1, the method is performed at atmospheric pressure.

11. The method of claim 1, wherein:
the droplet is in the second arm of the confinement region; and
the second arm of the channel further comprises a collection region such that the second arm of the confinement region further comprises a collection region; and
the method further comprises:
applying a fourth DC voltage to the second DC electrode to translocate the droplet to the collection region of the second arm of the confinement region; and
collecting the droplet by turning off the AC voltage to at least the second pair of AC electrodes such that the droplet falls into the collection region of the second arm of the channel.

12. The method of claim 1, wherein:
the second arm of the confinement region further comprises a second detection region; and
the device further comprises:
a fourth pair of alternating current (AC) electrodes disposed on the surface of the insulating substrate, wherein each of the AC electrodes comprising the fourth pair of AC electrodes is spaced apart on the surface of the insulating substrate such that the fourth pair of AC electrodes define a fourth arm of a channel, and wherein each of AC electrodes comprising the fourth pair of AC electrodes is electrically connected to an AC voltage source;
a fourth direct current (DC) electrode disposed on the surface of the insulating substrate and interspersed within the fourth arm of the channel, wherein the fourth DC electrode is electrically connected to a DC voltage source;
a fifth pair of alternating current (AC) electrodes disposed on the surface of the insulating substrate, wherein each of the AC electrodes comprising the fifth pair of AC electrodes is spaced apart on the surface of the insulating substrate such that the fifth pair of AC electrodes define a fifth arm of a channel, and wherein each of AC electrodes comprising the fifth pair of AC electrodes is electrically connected to an AC voltage source;
a fifth direct current (DC) electrode disposed on the surface of the insulating substrate and interspersed within the fifth arm of the channel, wherein the fifth DC electrode is electrically connected to a DC voltage source;
wherein the second arm of the channel, the fourth arm of the channel, and the fifth arm of the channel intersect at a second junction; and
applying AC voltage to the fourth pair of AC electrodes and the fifth pair of AC electrodes, and the third pair of AC electrodes, such that the confinement region further comprises a fourth arm and a fifth arm, wherein the second, fourth, and fifth arms of the confinement region intersect at a second junction.

13. The method of claim 12, wherein:
the droplet is in the second arm of the confinement region; and
the method further comprises:
   applying a fourth DC voltage to the second DC electrode to translocate the droplet to the second detection region;
   determining a second characteristic of the particle in the droplet at the second detection region;
   applying a fifth DC voltage to the second DC electrode to translocate the droplet from the second detection region to the second junction of the confinement region; and
   applying a sixth DC voltage to the second DC electrode, the fourth DC electrode, the fifth DC electrode, or a combination thereof to translocate the droplet from the second junction of the confinement region to the fourth arm of the confinement region or the fifth arm of the confinement region based on the second characteristic of the particle, thereby sorting the droplet based on the second characteristic of the particle.

14. The method of claim 13, wherein:
the droplet is in the fourth arm of the confinement region;
the fourth arm of the channel further comprises a collection region such that the fourth arm of the confinement region further comprises a collection region; and
the method further comprises:
   applying a seventh DC voltage to the fourth DC electrode to translocate the droplet to the collection region of the fourth arm of the confinement region; and
   collecting the droplet by turning off the AC voltage to at least the fourth pair of AC electrodes, such that the droplet falls into the collection region of the fourth arm of the channel.

15. The method of claim 13, wherein the second characteristic of the particle comprises the presence, absence, or intensity of absorbance; the presence, absence, or intensity of scattering; the presence, absence, or intensity of fluorescence; the size of the particle; the number of particles in the droplet; or a combination thereof.

16. The method of claim 12, wherein:
the third arm of the confinement region further comprises third detection region; and
the device further comprises:
   a sixth pair of alternating current (AC) electrodes disposed on the surface of the insulating substrate, wherein each of the AC electrodes comprising the sixth pair of AC electrodes is spaced apart on the surface of the insulating substrate such that the sixth pair of AC electrodes define a sixth arm of a channel, and wherein each of AC electrodes comprising the sixth pair of AC electrodes is electrically connected to an AC voltage source;
   a sixth direct current (DC) electrode disposed on the surface of the insulating substrate and interspersed within the sixth arm of the channel, wherein the sixth DC electrode is electrically connected to a DC voltage source;
   a seventh pair of alternating current (AC) electrodes disposed on the surface of the insulating substrate, wherein each of the AC electrodes comprising the seventh pair of AC electrodes is spaced apart on the surface of the insulating substrate such that the seventh pair of AC electrodes define a seventh arm of a channel, and wherein each of AC electrodes comprising the seventh pair of AC electrodes is electrically connected to an AC voltage source;
   a seventh direct current (DC) electrode disposed on the surface of the insulating substrate and interspersed within the seventh arm of the channel, wherein the seventh DC electrode is electrically connected to a DC voltage source;
   wherein the third arm of the channel, the sixth arm of the channel, and the seventh arm of the channel intersect at a third junction; and
applying AC voltage to the sixth pair of AC electrodes and the seventh pair of AC electrodes, such that the confinement region further comprises a sixth arm and a seventh arm, wherein the third, sixth, and seventh arms of the confinement region intersect at a third junction.

17. The method of claim 16, wherein:
the droplet is in the third arm of the confinement region; and
the method further comprises:
   applying an eighth DC voltage to the third DC electrode to translocate the droplet to the third detection region;
   determining a third characteristic of the particle in the droplet at the third detection region;
   applying a ninth DC voltage to the third DC electrode to translocate the droplet from the third detection region to the third junction of the confinement region; and
   applying a tenth DC voltage to the third DC electrode, the sixth DC electrode, the seventh DC electrode, or a combination thereof to translocate the droplet from the third junction of the confinement region to the sixth arm of the confinement region or the seventh arm of the confinement region based on the third characteristic of the particle, thereby sorting the droplet based on the third characteristic of the particle.

18. The method of claim 17, wherein:
the droplet is in the sixth arm of the confinement region; and
the sixth arm of the channel further comprises a collection region such that the sixth arm of the confinement region further comprises a collection region; and
the method further comprises:
   applying an eleventh DC voltage to the sixth DC electrode to translocate the droplet to the collection region of the sixth arm of the confinement;
   collecting the droplet by turning off the AC voltage to at least the sixth pair of AC electrodes, such that the droplet falls into the collection region of the sixth arm of the channel.

19. The method of claim 17, wherein the third characteristic of the particle comprises the presence, absence, or intensity of absorbance; the presence, absence, or intensity of scattering; the presence, absence, or intensity of fluorescence; the size of the particle; the number of particles in the droplet; or a combination thereof.

20. A system comprising:
a device comprising:
   an insulating substrate having a surface;
   a first pair of alternating current (AC) electrodes disposed on the surface of the insulating substrate, wherein each of the AC electrodes comprising the first pair of AC electrodes is spaced apart on the surface of the insulating substrate such that the first pair of AC electrodes define a first arm of a channel;

a first direct current (DC) electrodes disposed on the surface of the insulating substrate and interspersed within the first arm of the channel;

a second pair of alternating current (AC) electrodes disposed on the surface of the insulating substrate, wherein each of the AC electrodes comprising the second pair of AC electrodes is spaced apart on the surface of the insulating substrate such that the second pair of AC electrodes define a second arm of a channel;

a second direct current (DC) electrodes disposed on the surface of the insulating substrate and interspersed within the second arm of the channel;

a third pair of alternating current (AC) electrodes disposed on the surface of the insulating substrate, wherein each of the AC electrodes comprising the third pair of AC electrodes is spaced apart on the surface of the insulating substrate such that the third pair of AC electrodes define a third arm of a channel;

a third direct current (DC) electrodes disposed on the surface of the insulating substrate and interspersed within the third arm of the channel;

wherein the first, second, and third arms of the channel intersect at a junction; and wherein the length of the first arm of the channel, the second arm of the channel, the third arm of the channel, or a combination thereof is from 10 millimeters (mm) to 100 mm;

an AC voltage source electrically connected to the first pair of AC electrodes, the second pair of AC electrodes, and the third pair of AC electrodes, wherein applying an AC voltage to the first pair of AC electrodes, the second pair of AC electrodes, and the third pair of AC electrodes generates an electromagnetic trapping field defining a confinement region, wherein the confinement region is proximate the channel and above the surface of the insulating substrate;

wherein the confinement region comprises:
    a first arm, a second arm, and a third arm, and wherein the first, second, and third arms of the confinement region intersect at a junction; and
    wherein the first arm of the confinement region comprises a loading region and a detection region;

a droplet generating device, wherein the electromagnetic trapping field traps a droplet having a surface charge injected into the loading region from the droplet generating device in the confinement region, such that the droplet levitates above the surface of the insulating substrate, wherein the droplet comprises a liquid sample comprising a particle a DC voltage source electrically connected to the first DC electrode, the second DC electrode, and the third DC electrode, wherein applying a first DC voltage to the first DC electrode translocates the droplet from the loading region to the detection region; and an instrument configured to determine a characteristic of the particle in the droplet at the detection region;

wherein applying a second DC voltage to the first DC electrode translocates the droplet from the detection region to the junction of the confinement region; and wherein applying a third DC voltage to the first DC electrode, the second DC electrode, the third DC electrode, of a combination thereof translocates the droplet from the junction of the confinement region to the second arm of the confinement region or the third arm of the confinement region based on the characteristic of the particle, thereby sorting the droplet based on the characteristic of the particle.

* * * * *